(12) United States Patent
Huang et al.

(10) Patent No.: US 11,278,561 B2
(45) Date of Patent: Mar. 22, 2022

(54) COMBINATION TREATMENT FOR HEMATOLOGICAL CANCERS

(71) Applicant: Geron Corporation, Menlo Park, CA (US)

(72) Inventors: Fei Huang, Spring House, PA (US); Joshua J. Rusbuldt, Spring House, PA (US); Aleksandra Rizo, Raritan, NJ (US)

(73) Assignee: Geron Corporation, Foster City, CA (US)

( * ) Notice: Subject to any disclaimer, the term of this patent is extended or adjusted under 35 U.S.C. 154(b) by 847 days.

(21) Appl. No.: 15/662,706

(22) Filed: Jul. 28, 2017

(65) Prior Publication Data

US 2018/0036336 A1  Feb. 8, 2018

Related U.S. Application Data

(60) Provisional application No. 62/370,018, filed on Aug. 2, 2016, provisional application No. 62/422,738, filed on Nov. 16, 2016.

(30) Foreign Application Priority Data

Nov. 4, 2016 (EP) ..................... 16197293

(51) Int. Cl.
*A61K 31/7125* (2006.01)
*A61K 31/496* (2006.01)
(Continued)

(52) U.S. Cl.
CPC ........ *A61K 31/7125* (2013.01); *A61K 31/496* (2013.01); *A61K 31/635* (2013.01); *A61K 45/06* (2013.01)

(58) Field of Classification Search
CPC ... A61K 31/7125; A61K 31/496; A61K 45/06
(Continued)

(56) References Cited

U.S. PATENT DOCUMENTS 5,583,016 A   12/1996   Villeponteau et al.
5,776,679 A   7/1998    Villeponteau et al.
(Continued)

FOREIGN PATENT DOCUMENTS

CN   104936602   9/2015
CN   104994858   10/2015
(Continued)

OTHER PUBLICATIONS

Cantilena et al., Blood 2015, vol. 126 (23), p. 1267. (Year: 2015).*
(Continued)

*Primary Examiner* — Craig D Ricci
*Assistant Examiner* — Janet L Coppins
(74) *Attorney, Agent, or Firm* — Bozicevic, Field & Francis LLP; Rudy J. Ng

(57) ABSTRACT

The present invention relates to a combination treatment for hematological cancers. More specifically; a combination of a telomerase inhibitor and a Bcl-2 inhibitor are useful in treating hematological cancers, including AML. In certain embodiments, the telomerase inhibitor is imetelstat or imetelstat sodium and the Bcl-2 inhibitor is ABT-199.

5 Claims, 31 Drawing Sheets

Specification includes a Sequence Listing.

(51) Int. Cl.
  *A61K 31/635* (2006.01)
  *A61K 45/06* (2006.01)
(58) Field of Classification Search
  USPC ........................................................ 514/603
  See application file for complete search history.

(56) References Cited

U.S. PATENT DOCUMENTS

| | | |
|---|---|---|
| 5,837,857 A | 11/1998 | Villeponteau et al. |
| 5,958,680 A | 9/1999 | Villeponteau et al. |
| 6,548,298 B2 | 4/2003 | Villeponteau et al. |
| 6,608,036 B1 | 8/2003 | Gryaznov et al. |
| 6,835,826 B2 | 12/2004 | Gryaznov et al. |
| 7,138,383 B2 | 11/2006 | Gryaznov et al. |
| 7,494,982 B2 | 2/2009 | Gryaznov et al. |
| 7,989,428 B2 | 8/2011 | Go et al. |
| 7,998,938 B2 | 8/2011 | Moore et al. |
| 8,785,409 B2 | 7/2014 | Gryaznov et al. |
| 8,877,723 B2 | 11/2014 | Harley et al. |
| 9,155,753 B2 | 10/2015 | Tressler et al. |
| 9,200,327 B2 | 12/2015 | Bassett et al. |
| 9,375,485 B2 | 6/2016 | Stuart et al. |
| 9,388,415 B2 | 7/2016 | Gryaznov |
| 9,388,416 B2 | 7/2016 | Gryaznov |
| 9,404,112 B2 | 8/2016 | Gryaznov |
| 9,617,583 B2 | 4/2017 | Harley et al. |
| 9,657,296 B2 | 5/2017 | Gryaznov et al. |
| 9,732,114 B2 | 8/2017 | Gryaznov et al. |
| 9,951,389 B2 | 4/2018 | Bassett et al. |
| 10,196,641 B2 | 2/2019 | Gryaznov et al. |
| 10,196,677 B2 | 2/2019 | Harley et al. |
| 2016/0028762 A1 | 10/2016 | Tefferi |
| 2016/0287625 A1 | 10/2016 | Tefferi |
| 2019/0030064 A1 | 1/2019 | Rizo et al. |

FOREIGN PATENT DOCUMENTS

| | | |
|---|---|---|
| CN | 105164117 | 12/2015 |
| WO | 01/18015 | 3/2001 |
| WO | 2005/023994 | 3/2005 |
| WO | 2006/113426 | 10/2006 |
| WO | 2006/113470 | 10/2006 |
| WO | 2006/124904 | 11/2006 |
| WO | 2008/054711 | 5/2008 |
| WO | 2008/094640 | 8/2008 |
| WO | 2008/112129 | 9/2008 |
| WO | 2010/045245 | 4/2010 |
| WO | 2011017096 A2 | 2/2011 |
| WO | 2014/085632 | 6/2014 |
| WO | 2014088785 A1 | 6/2014 |
| WO | 2014160071 A1 | 10/2014 |
| WO | 2015/069758 | 5/2015 |
| WO | WO2015191568 | 12/2015 |
| WO | WO2016046346 | 3/2016 |

OTHER PUBLICATIONS

Pubchem—Imetelstat sodium compound summary, created Mar. 2, 2014, pp. 1-19. (Year: 2014).*
Kuo and Bhatia, Cell Stem Cell 2014, vol. 15 (6), pp. 673-675. (Year: 2014).*
Pan et al, Cancer Discovery 2014, vol. 4 (3), pp. 362-375. (Year: 2014).*
European Search Report issued in European Application No. EP16197293.0 dated Apr. 5, 2017.
Ebrahim, A.S. et al., "Hematologic malignancies: new strategies to counter the BCL-2 protein", J. Cancer Res. Clin. Oncol., vol. 142, pp. 2013-2022, Apr. 4, 2014.
Fischer, U. et al., "Genomics and drug profiling of fatal TCF3-HLF-positive acute lymphoblastic leukemia identifies recurrent mutation patterns and therapeutic options", Nature Genetics, vol. 47, No. 9, pp. 1020-1029, Jul. 27, 2015.
Romero, D., Haematological Cancer—Promising Results of BCL2 Inhibition, Nature Reviews Clinical Oncology, vol. 12, No. 9, pp. 504, Aug. 11, 2015.
Ropio, J., "Telomerase Activation in Hematological Malignancies", Genes, vol. 7, No. 9, p. 61, Sep. 7, 2016.
Shammas, M.A. et al., Telomerase inhibitor GRN163L inhibits myeloma cell growth in vitro and in vivo, Leukemia, vol. 22, pp. 1410-1418, May 1, 2008.
Asal et al., (2003) "A Novel Telomerase Template Antagonist (GRN163) as a Potential Anticancer Agent", Cancer Res., (63)3931-9.
Baerlocher et al., (2012) "Imetelstat rapidly Induces and Maintains Substantial Hematologic and Molecular Responses in Patients with Essential Thrombocythemia (ET) who are Refractory or Intolerant to Prior Therapy: Preliminary Phase II Results", Blood (ASH Meeting Abstracts), 120(21):Abstract 179.
Baerlocher et al., (2012) "Imetelstat: A Novel Approach with Robust Hematologic and Molecular Responses in a Phase 2 study in Patients with Essential Thrombocythemia (ET) who are Refractory or Intolerant to Prior Therapy", Hematologica, 98(s1) Abstract S112.
Bruedigam et al., (2014) "Telomerase Inhibition Effectively Targets Mouse and Human AML Stem Cells and Delays Relapse following Chemotherapy", Cell Stem Cell, 15:775-790.
Brunold et al., (2011) "Imetelstat, A Potent Telomerase Inhibitor, Inhibits the Spontaneous Growth of CFU-Meg In Vitro From Essential Thrombocythemia Patients but Not From Healthy Individuals", Blood (ASH Annual Meeting Abstr.) 118(21):3843.
Chou et al., (1984) "Quantitative analysis of dose-effect relationships: the combined effects of multiple drugs or enzyme inhibitors", Adv Enzyme Regul, 22:27-55.
El-Daly et al., (2005) "Selective Cytotoxicity and telomere damage in leukemia cells using the telomerase inhibitor BIBR1532", Blood vol. 105, 4:1742-1749.
Gryaznov et al., (1993) "Modulation of oligonucleotide duplex and triplex stability via hydrophobic interactions", Nucl. Acids Res., 21:5909-15.
Gryaznov, (2012) "Oligonucleotide N3' →P5' Phosphoramidates and thio-phosphoramidates as Potential Therapeutic Agents", Chemistry and Bidiversity, 61-77.
Gryaznov et al., (1996) "Oligonucleotide N3'→P5' phosphoramidates as antisense agents", Nucl. Acids Res., 24(8):1508-14.
Gryaznov et al., (1999) "Oligonucleotide N3'→P5' phosphoramidates as potential therapeutic agents", Biochim. Biophys. Acta, 1489(1):131-40.
Gryaznov et al., (2003) "Oligonucleotide N3'→P5' thiophosphoramidate telomerase template antagonists as potential anticancer agents", Nucleosides, Nucleotides & Nucl. Acids, 22(5-8):577-581.
Gryaznov, (2010) "Oligonucleotide N3'-P' Phosphoramidates and Thio-Phosphoramidates as Potential Therapeutic Agents", Chemistry & Biodiversity, 7:477-493.
Gryaznov et al., (2001) "Telomerase inhibitors—oligonucleotide phosphoramidates as potential therapeutic agents", Nucleosides, Nucleotides & Nucl. Acids 20(4-7):401-410.
Herbert et al., (2005) "Lipid Modification of GRN163, an N3'→P5' thio-Phosphoramidate Oligonucleotide, Enhances the Potency of Telomerase Inhibition", Oncogene, 24(33):5262-5268.
Herbert et al., (2006) "Nonradioactive detection of telomerase activity using the telomeric repeat amplification protocol", Nat Protoc 1, 1583-1590.
Hou et al., (2001) "Real-time quantitative telomeric repeat amplification protocol assay for the detection of telomerase activity", Clin. Chem. 47:519-524.
Keller et al., (2009) "Telomeres and telomerase in chronic myeloid leukemiai impact for pathogenesis disease progression and targeted therapy", Hematological Oncology, 27(3):123-129.
Maritz et al., (2010) "Targeting telomerase in Hematologic malignancy", Future Oncology, 6(5):769-789.
Roth et al., (2010) "Imetelstat (GRN163L)—telomerase-based cancer therapy", Recent Results in Cancer Research, 184:221-234.
Roth et al., (2003) "Telomerase is limiting the growth of acute myeloid leukemia cells", Leukemia, 17(12):2410-2417.

(56) References Cited

OTHER PUBLICATIONS

Sumi et al., (2004) "A G-quadruplex interactive agent, telomestatin (SOT-095) induces telomere shortening with apoptosis and enhances chemosensitivity in acute myeloid leukemia", International Journal of Oncology, 24(6):1481-1487.

Tang et al., (2015) "What is synergy? The Saariselka agreement revisited", Frontiers in Pharmacology 6(181):1-5.

Wang et al., (2004) "Telomerase inhibition with an oligonucleotide telomerase template antagonist: in vitro and in vivo studies in multiple myeloma and lymphoma", Blood, 103(1):258-266.

Ward et al., (2005) "Pharmacological telomerase inhibition can sensitize drug-resistant and drug-sensitive cells to chemotherapeutic treatment", Mol. Pharmacol., 68:779-786.

Baerlocher, et al., (2015) "Telomerase inhibitor Imetelstat in Patients with Essential Thrombocythemia", The New England Journal of Medicine, vol. 373, No. 10, pp. 920-928.

BELLOT and WANG, (2013) "Extra-Telomeric Effects of Telomerase (hTERT) in Cell Death", Apoptosis, Chapter 5, pp. 95-112.

Li and Tergaonkar, (2014) "Noncanonical Functions of Telomerase: Implications in Telomerase-Targeted Cancer Therapies", Cancer Research, vol. 76, No. 6, pp. 1639-1644.

Tefferi, et al., (2015) "A Pilot Study of the Telomerase Inhibitor Imetelstat for Myelofirosis", The New England Journal of Medicine, vol. 373, No. 10, pp. 908-919.

Tefferi, et al., (2016) "Imetelstat Therapy in Refractory Anemia With Ring Sideroblasts With or Without Thrombocytosis", Blood Cancer Journal, vol. 6, e405, 2 pages.

Xiaofang, Guo, (2001) "Expression and Research Progress on Telomerase of Hematological Malignancies", Foreign Medical Sciences (Section of Clinical Biochemistry and Laboratory Medicine), 22(3):132-136.

Lehmann et al. (2016) "Superior anti-tumor activity of the MDM2 antagonist idasanutlin and the Bcl-2 inhibitor venetoclax in p53 wild-type acute myeloid leukemia models", Journal of Hematology & Oncology, vol. 9, 13 pages.

Zhao Jingping et al., (2015) "Expression and Significances of c-Cbl and Bcl-2 Proteins in Classical Myeloproliferative Neoplasms", Chinese Remedies & Clinics, 15(10):1412-1416.

Kuo, Ya-Huei and Bhatia, Ravi, (2014) "Pushing the Limits: Defeating Leukemia Stem Cells by Depleting Telomerase", Cell Stem Cell, 15(6):673-675.

Rongqing, Pari et al., (2014) "Selective BCL-2 Inhibition by ABT-199 Causes On-Target Cell Death in Acute Myeloid Leukemia", Cancer Discovery, 4(3):362-375.

\* cited by examiner

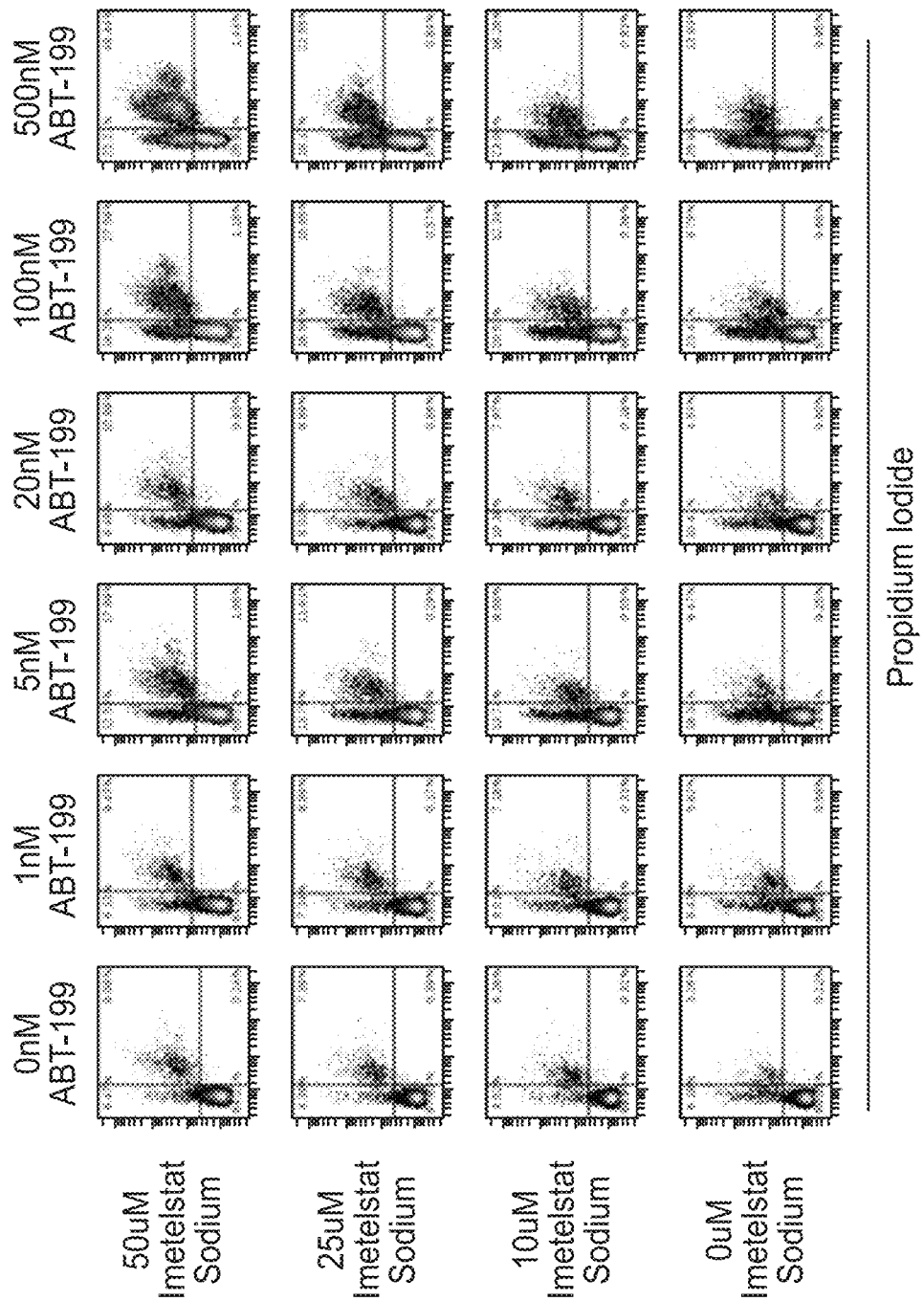

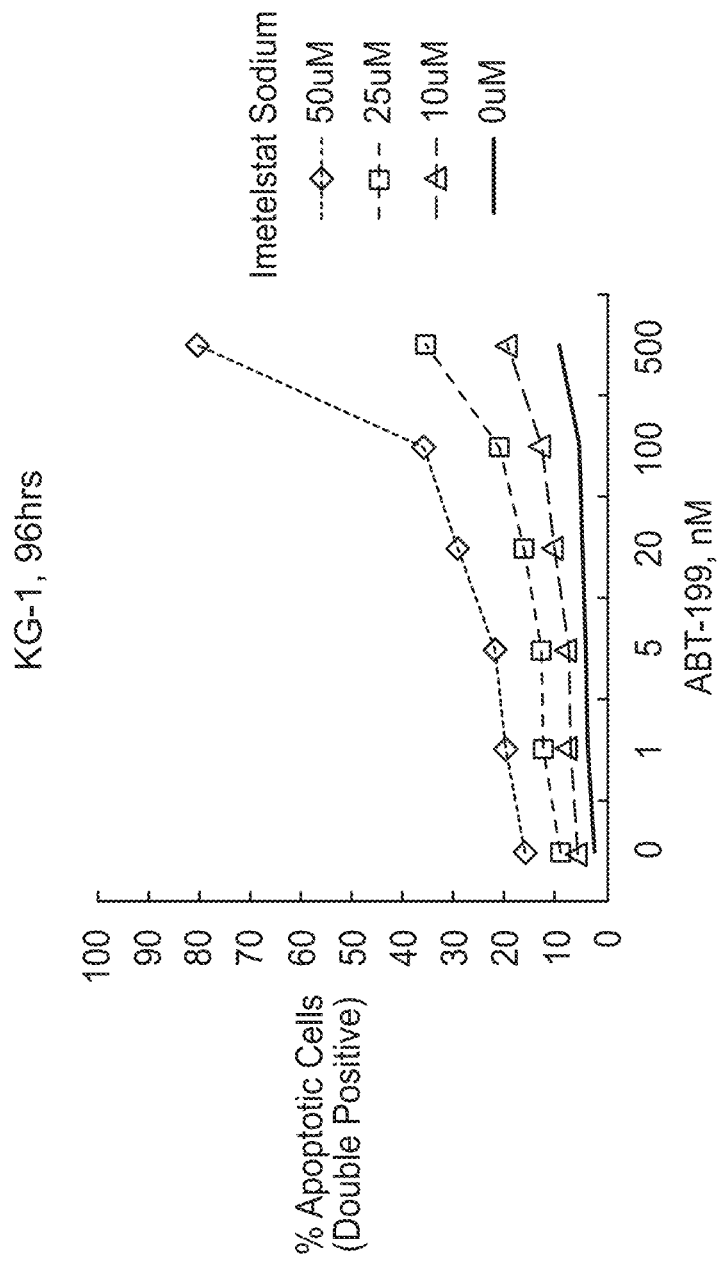

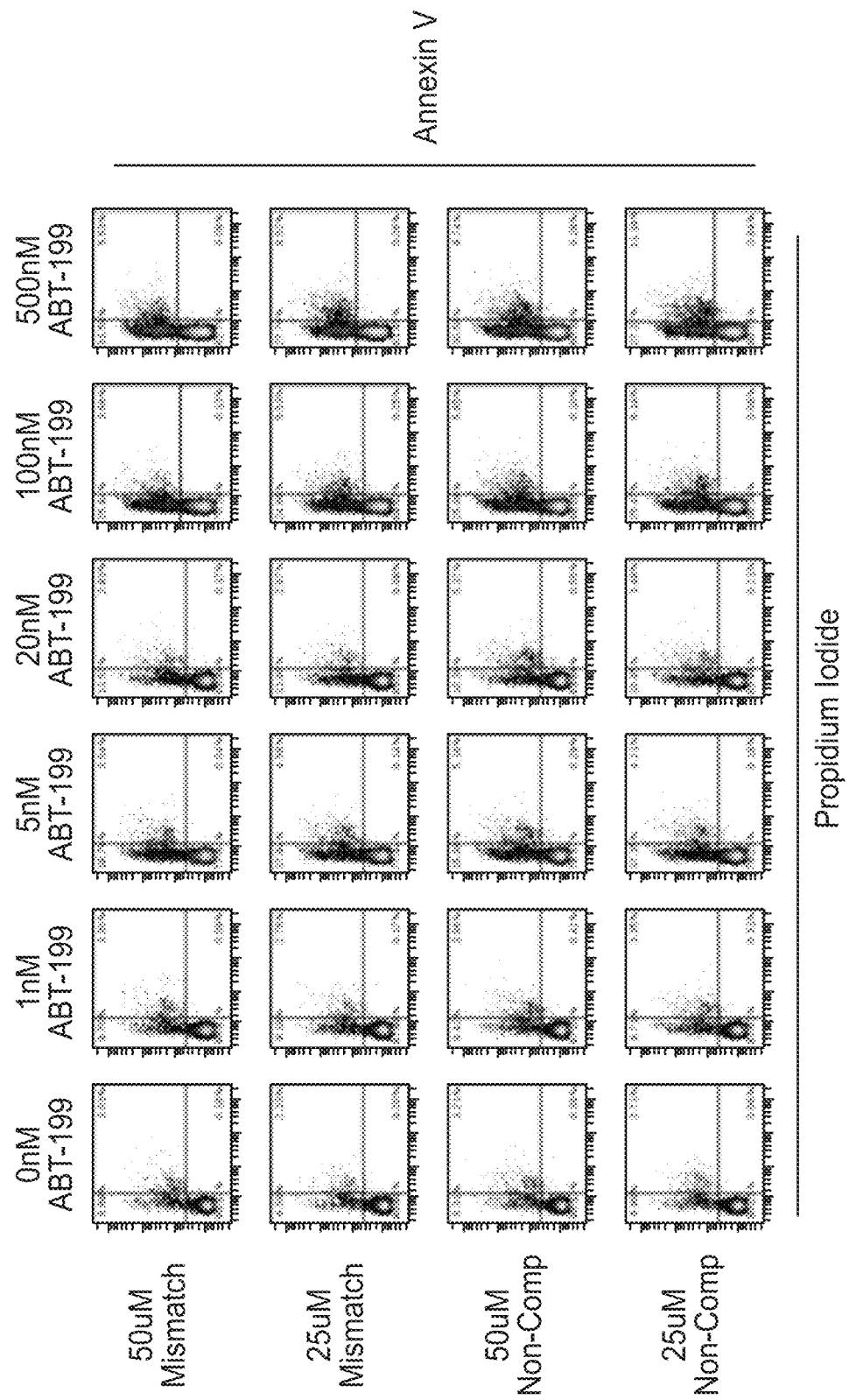

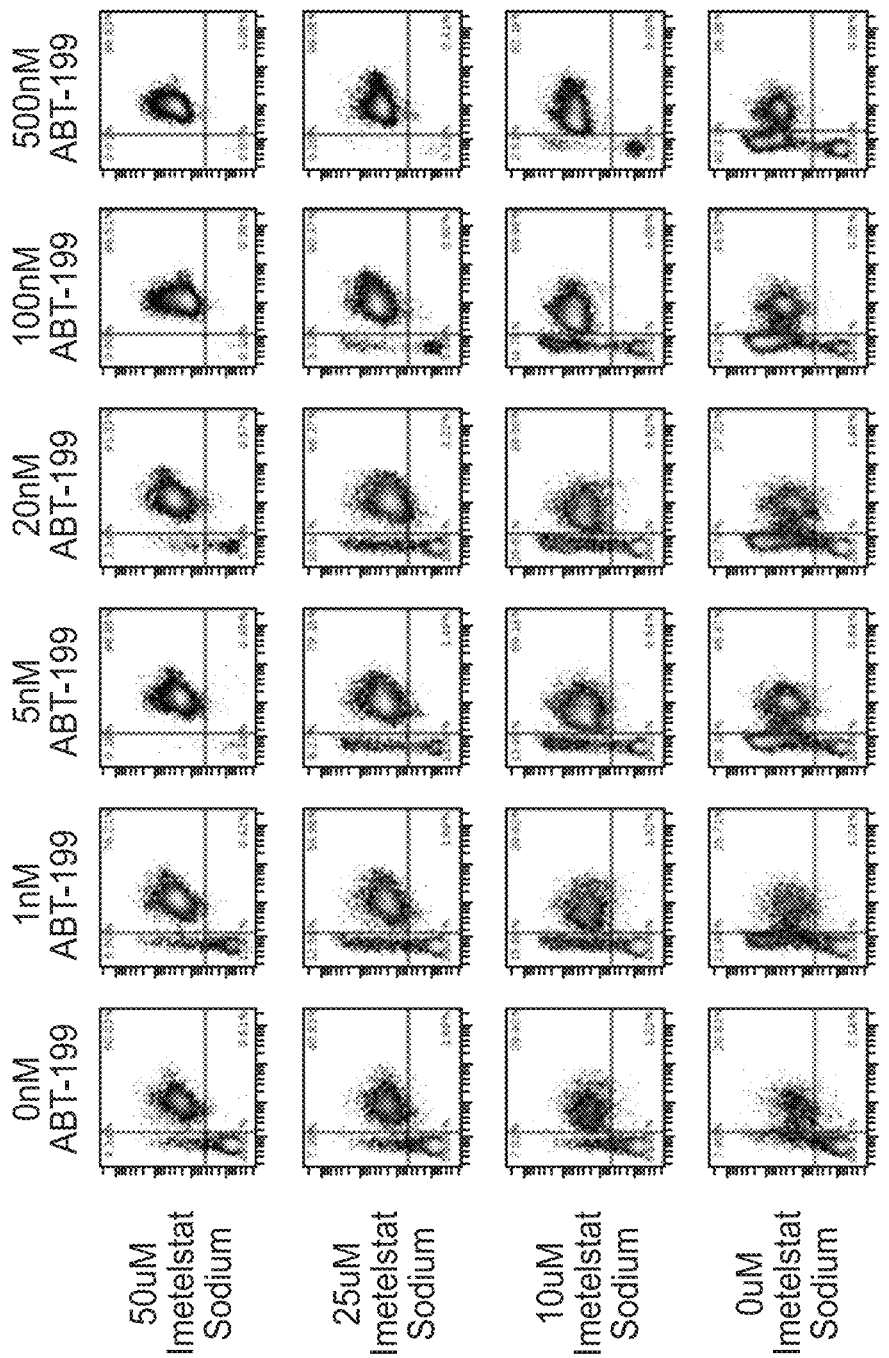

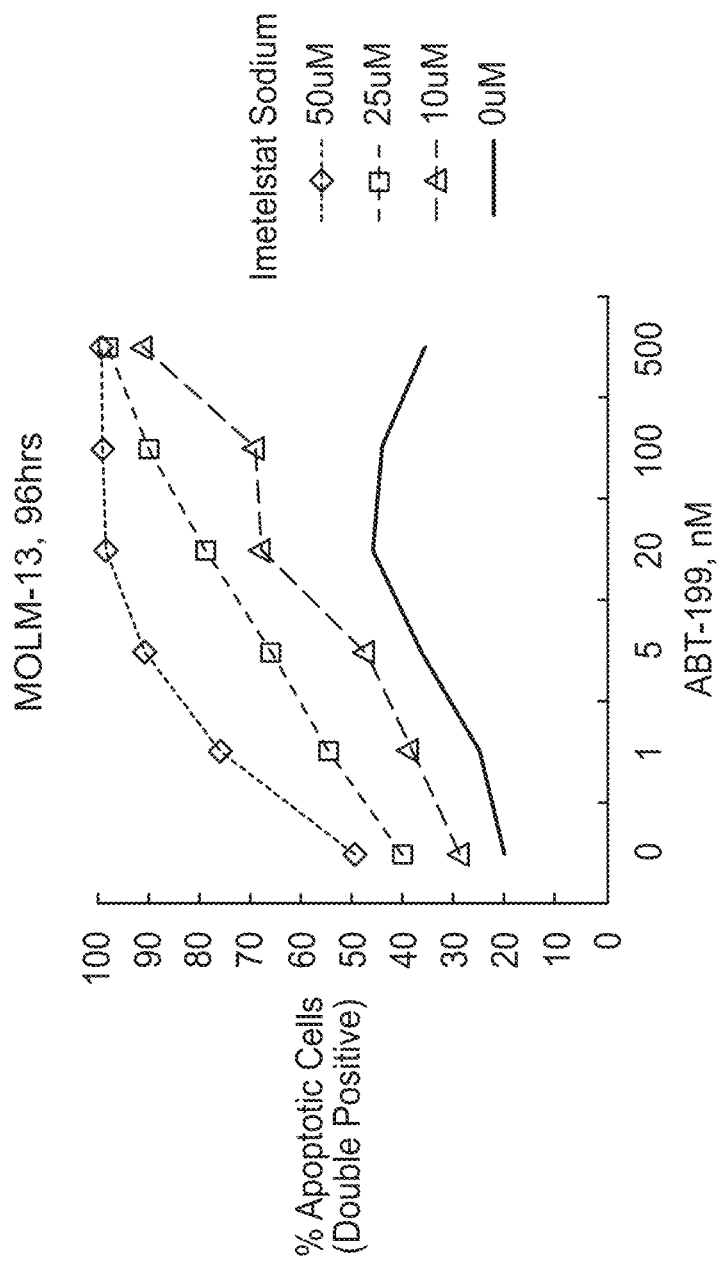

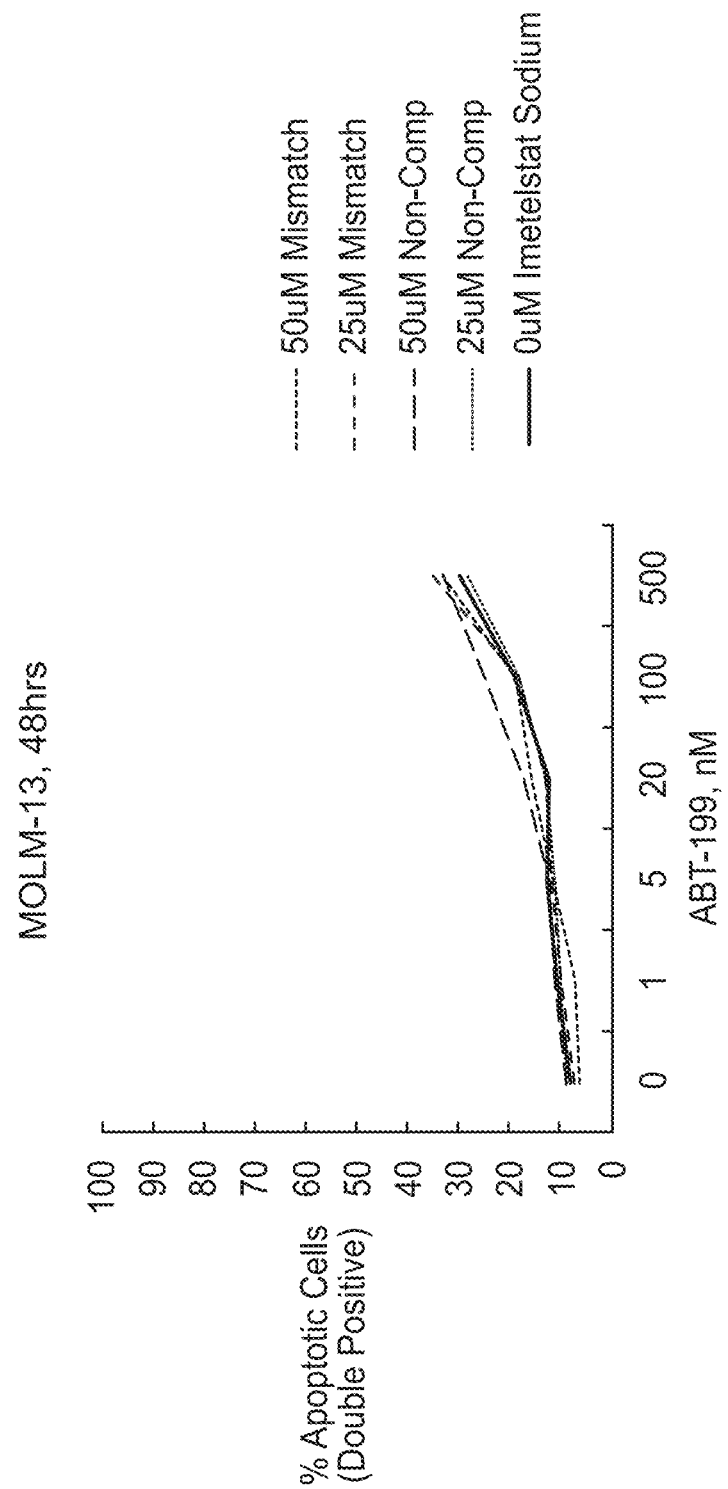

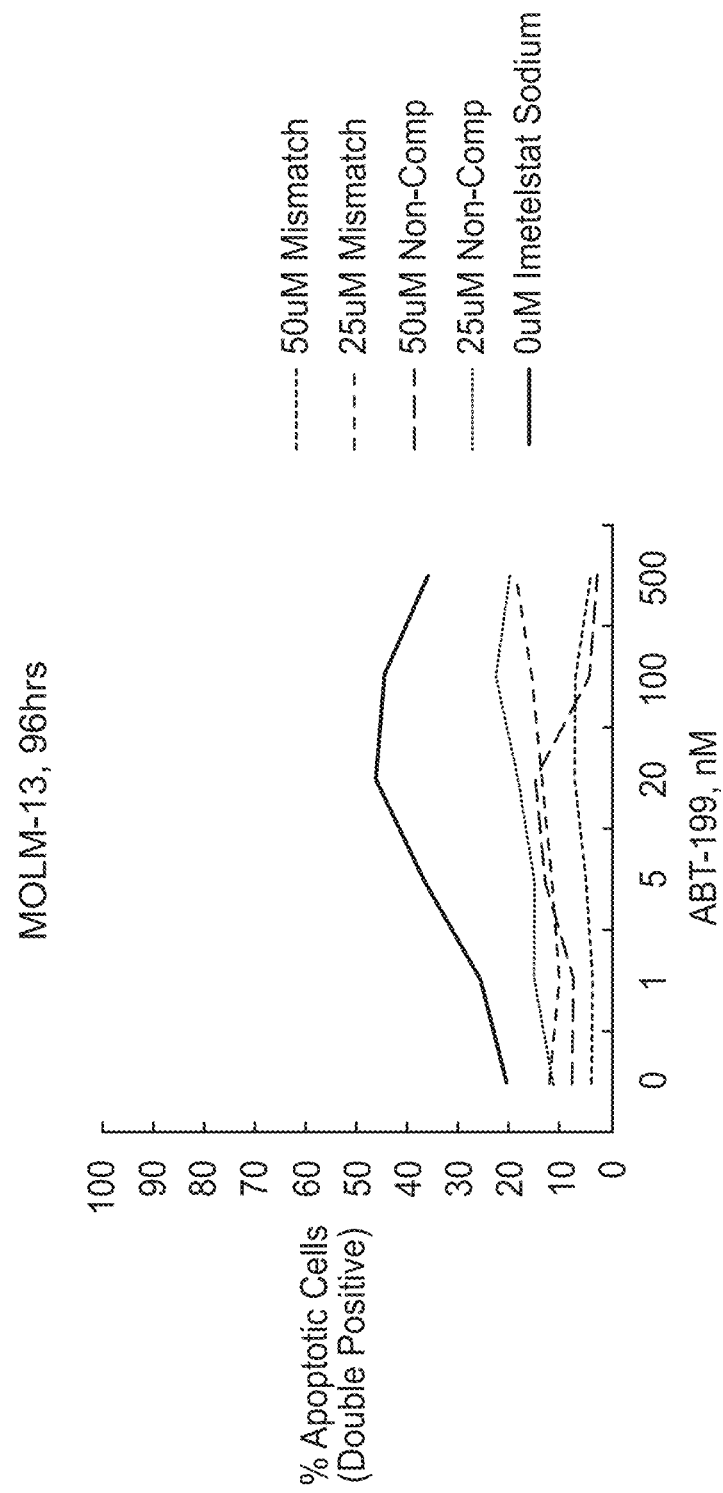

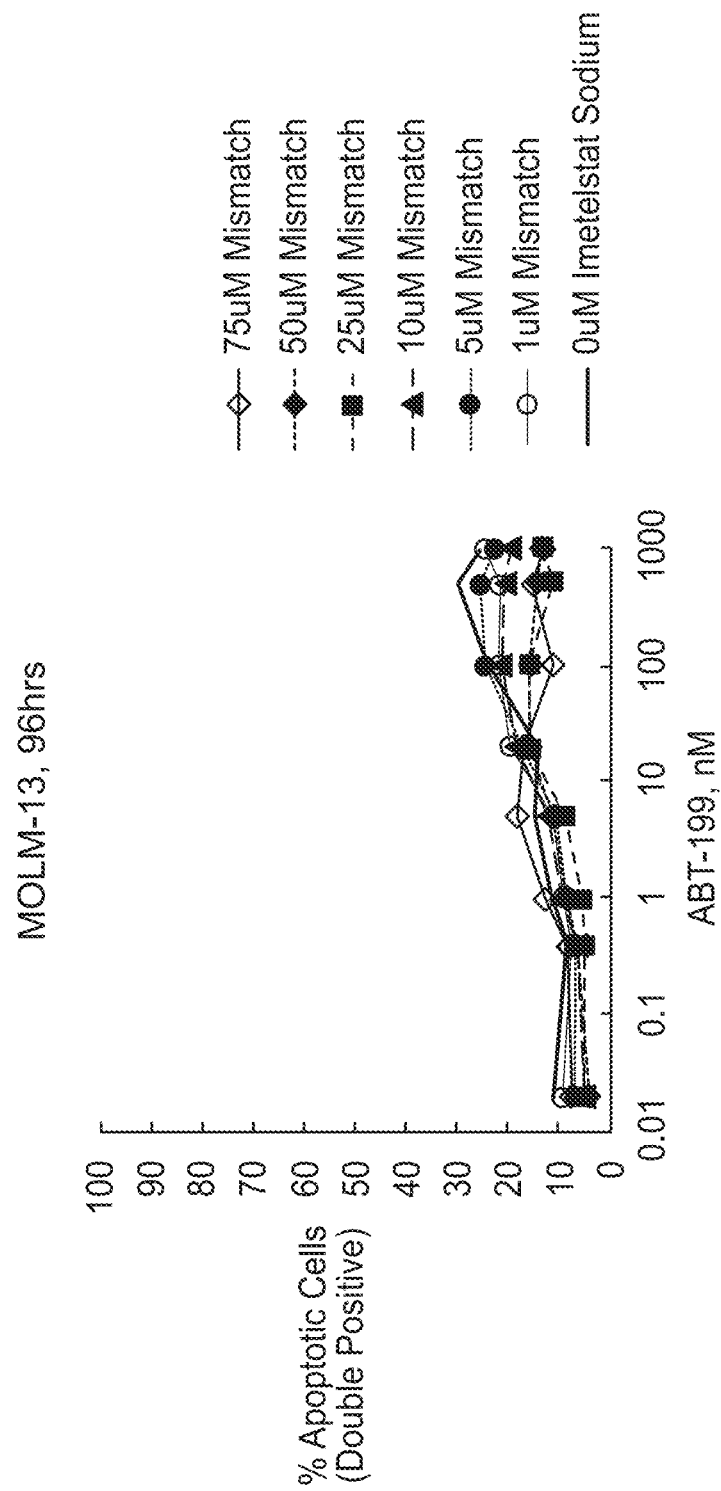

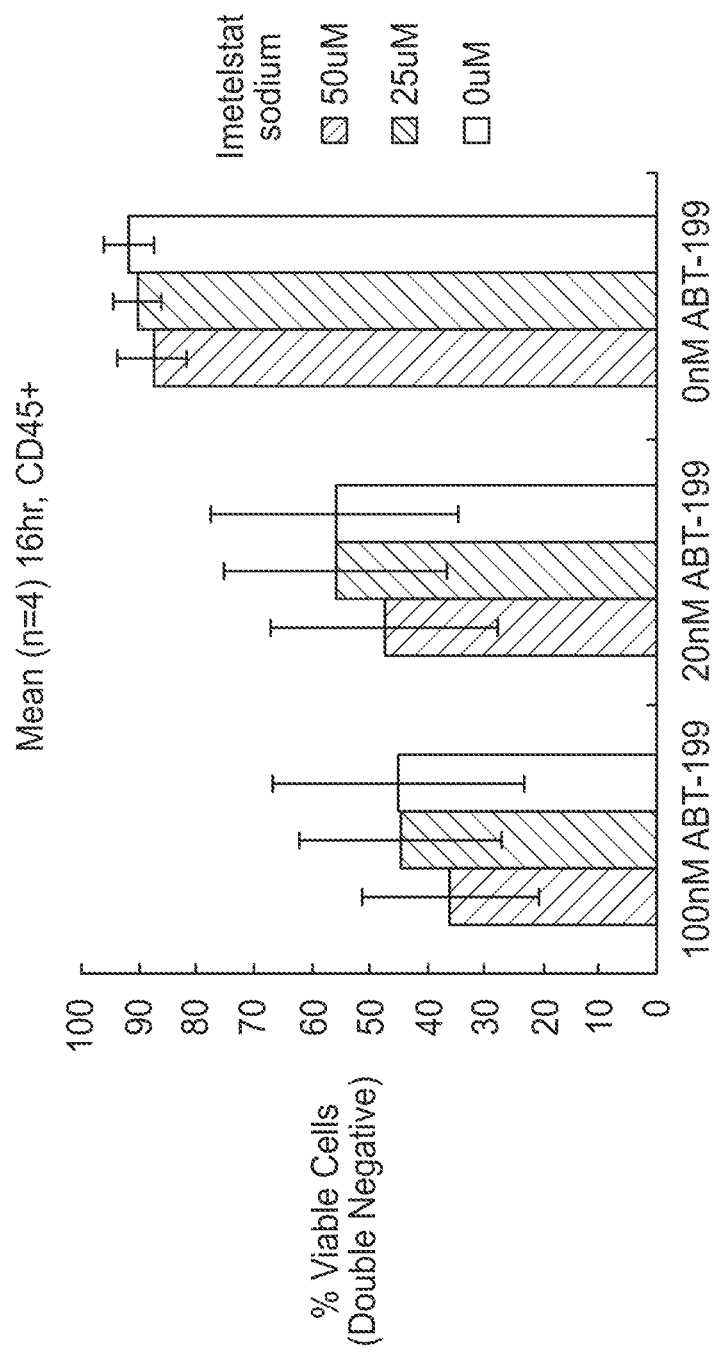

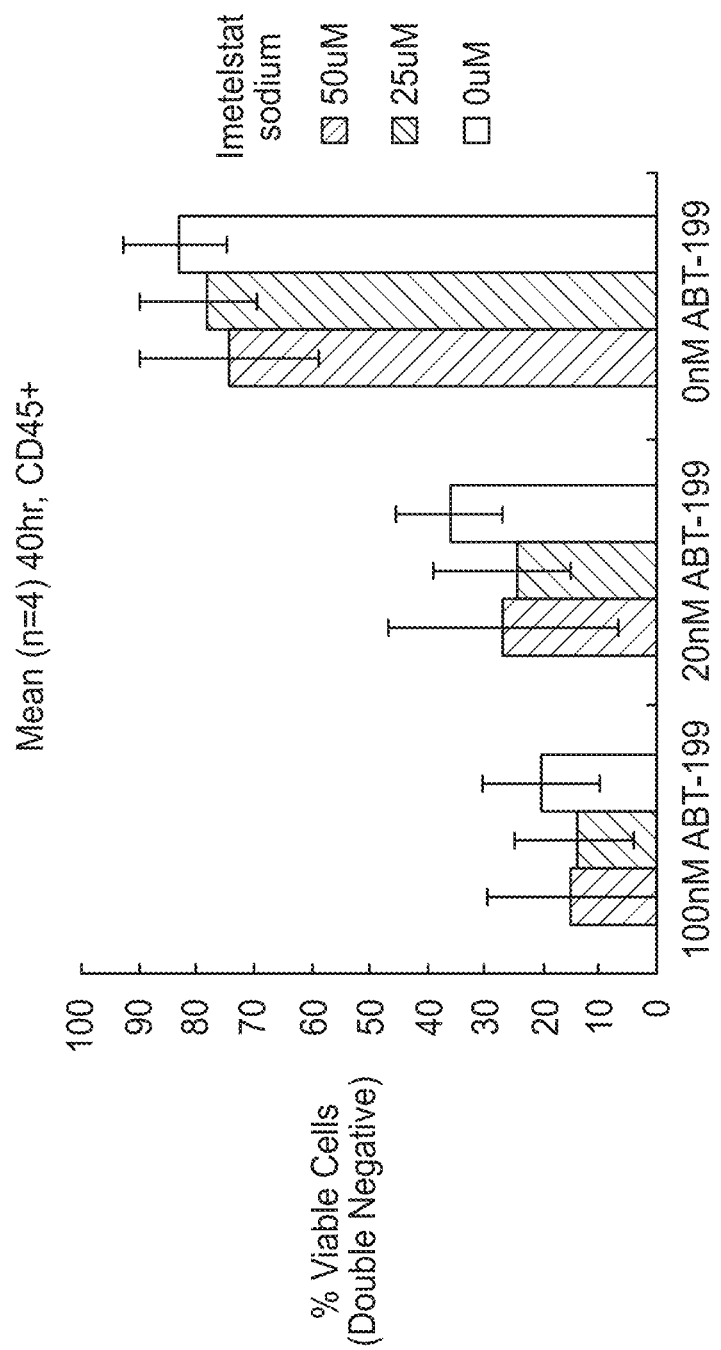

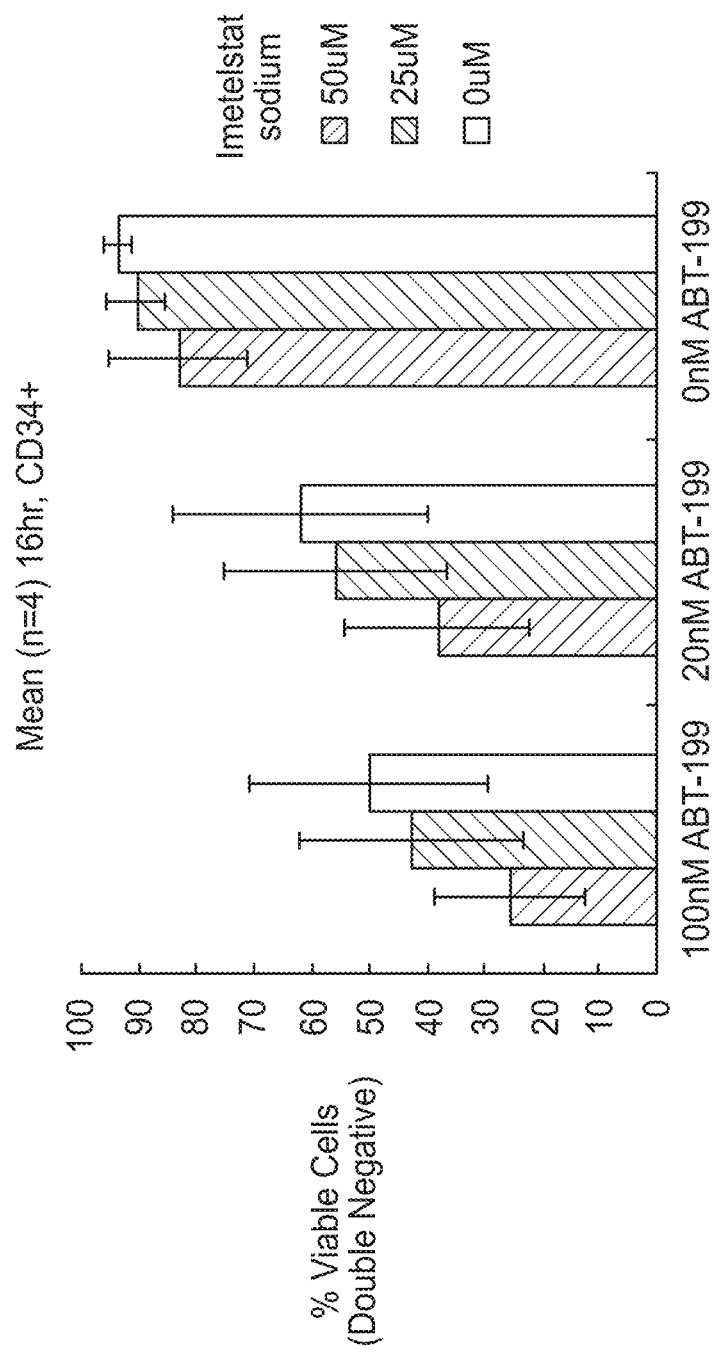

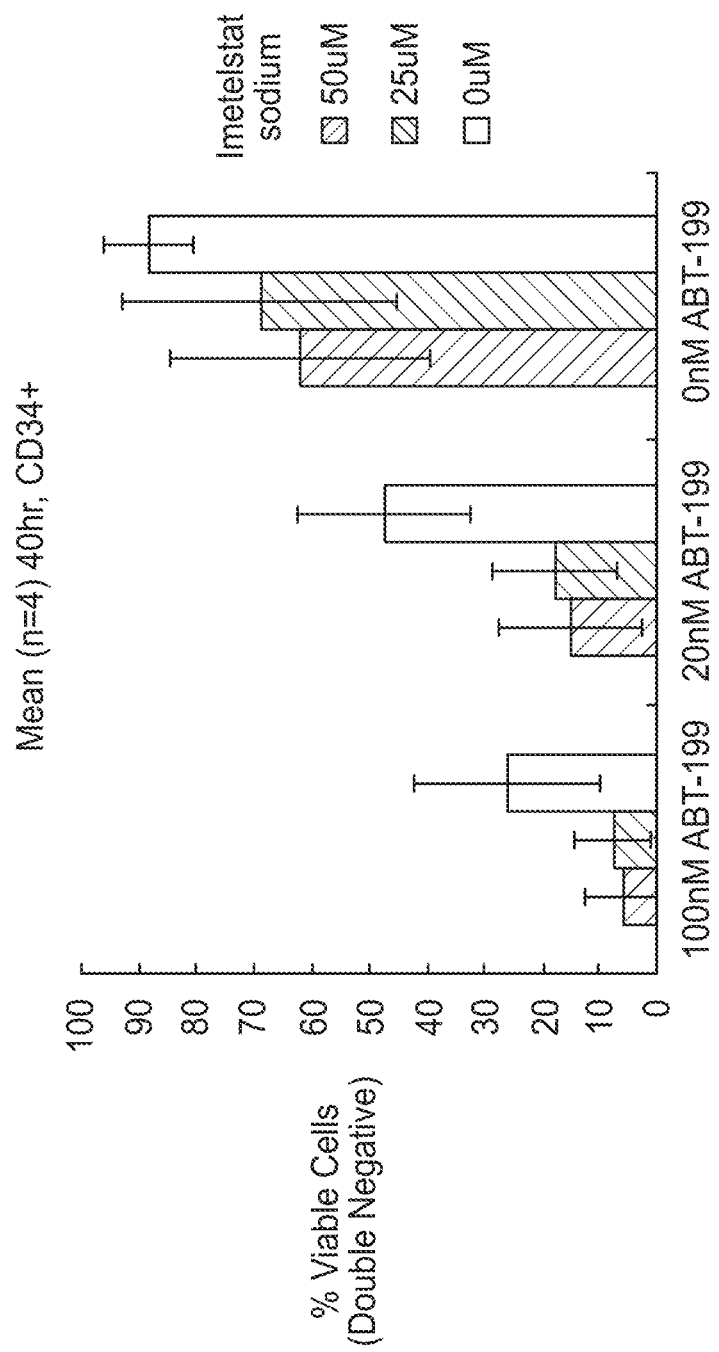

COMBINATION TREATMENT FOR HEMATOLOGICAL CANCERS

CROSS-REFERENCE TO RELATED APPLICATIONS

This application claims priority to U.S. Provisional Application No. 62/370,018 (filed Aug. 2, 2016), European Patent Application No. 16197293.0 (filed Nov. 4, 2016) and U.S. Provisional Application No. 62/422,738 (Nov. 16, 2016), the entire contents of each is incorporated by reference herein.

SEQUENCE LISTING

The instant application contains a Sequence Listing which has been filed electronically in ASCII format and is hereby incorporated by reference in its entirety. Said ASCII copy, created on Jul. 14, 2017, is named PRD3424USNP_SL.txt and is 2,158 bytes in size.

FIELD OF THE INVENTION

The disclosure provided herein relates to treatment of hematological cancers using the combination of a telomerase inhibitor and a Bcl-2 inhibitor.

BACKGROUND OF THE INVENTION

Patients of acute myeloid leukemia (AML) have limited treatment options at diagnosis; treatment typically takes the form of chemotherapy to quickly reduce the leukemic cell burden. Invasive leukapheresis procedures to remove large numbers of leukocytes (normal and diseased) may be applied in parallel to chemotherapy to temporarily lower tumor cell burden. Induction phase chemotherapy can be successful but, most healthy cells residing in patient bone marrow are also killed, causing illness and requiring additional palliative therapy to ward off infection and raise leukocyte counts. Additional rounds of chemotherapy can be used in an attempt to keep patients in remission; but relapse is common.

Telomerase is present in over 90% of tumors across all cancer types; and is lacking in normal, healthy tissues. Imetelstat sodium is a novel, first-in-class telomerase inhibitor that is a covalently-lipidated 13-mer oligonucleotide (shown below) complimentary to the human telomerase RNA (hTR) template region. Imetelstat sodium does not function through an anti-sense mechanism and therefore lacks the side effects commonly observed with such therapies. Imetelstat sodium is the sodium salt of imetelstat (shown below):

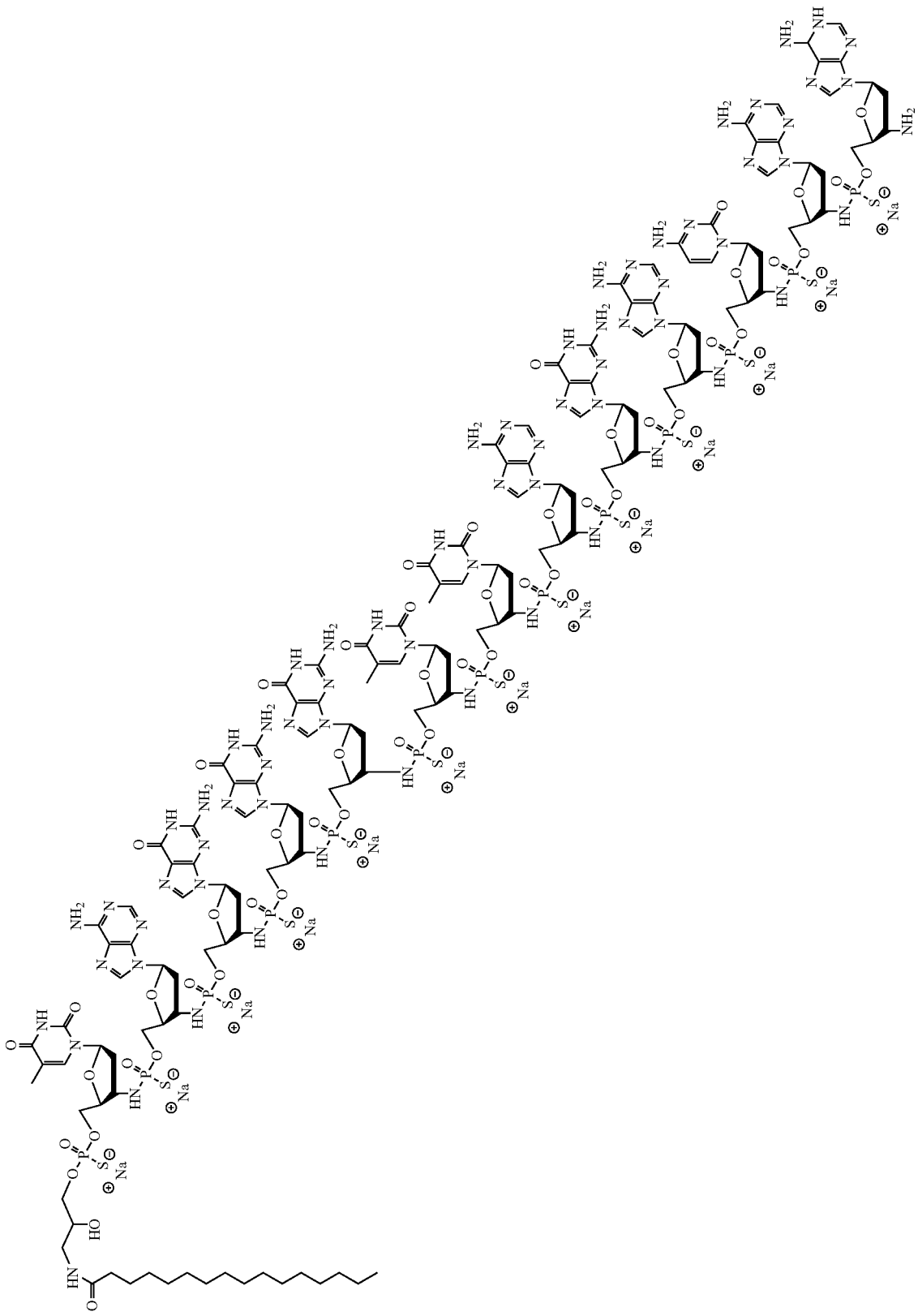

Unless otherwise indicated or clear from the context, references below to imetelstat also include salts thereof. As mentioned above, imetelstat sodium in particular is the sodium salt of imetelstat.

ABT-199/venetoclax (trade name Venclexta) is an FDA approved Bcl-2 inhibitor for use in chronic lymphocytic leukemia (CLL) patients with del17p who are relapsed/refractory. ABT-199 is also known as ABT 199, GDC0199, GDC-0199 or RG7601. The chemical name for ABT-199 is 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo [2,3-b]pyridin-5-yloxy)benzamide (Cas No. 1257044-40-8). Unless otherwise indicated or clear from the context, references below to ABT-199 also include pharmaceutically acceptable salts thereof. Specifically in the Examples however, ABT-199 was used in the free base form.

ABT-199, shown below in the free base form, is highly specific to Bcl-2, unlike other first generation inhibitors which show affinity for related Bcl family members and induce greater side effects. Inhibition of Bcl-2 blocks the pro-apoptotic signals caused by damage to or abnormalities within cellular DNA and ultimately leads to programmed cell death in treated cells via the caspase cascade and apoptosis through the intrinsic pathway.

(b) intravenous administration of about 7-10 mg/kg imetelstat once weekly for four weeks; (c) intravenous administration of about 2.5-10 mg/kg imetelstat once every three weeks; or (d) intravenous administration of about 0.5-9.4 mg/kg imetelstat once every four weeks.

The method of treatment may be used to treat a hematological cancer selected from: acute myeloid leukemia; essential thrombocythemia; polycythemia vera; primary myelofibrosis; systemic mastocytosis; chronic myeloid leukemia; chronic neutrophilic leukemia; chronic eosinophilic leukemia; refractory anemia with ringed sideroblasts; refractory cytopenia with multilineage dysplasia; refractory anemia with excess blasts; type 1; refractory anemia with excess blasts; type 2; myelodysplastic syndrome (MDS) with isolated del (5q); MDS unclassifiable; chronic myelomonocytic leukemia (CML); atypical chronic myeloid leukemia; juvenile myelomonocytic leukemia; myeloproliferative/myelodysplastic syndromes—unclassifiable; B lymphoblastic leukemia/lymphoma; T lymphoblastic leukemia/lymphoma; diffuse large B-cell lymphoma; primary central nervous system lymphoma; primary mediastinal B-cell lymphoma; Burkitt lymphoma/leukemia; follicular lymphoma; chronic lymphocytic leukemia (CLL)/small lymphocytic lymphoma; B-cell prolymphocytic leukemia; lymphoplasmacytic lymphoma/Waldenström macroglobulinemia; Mantle

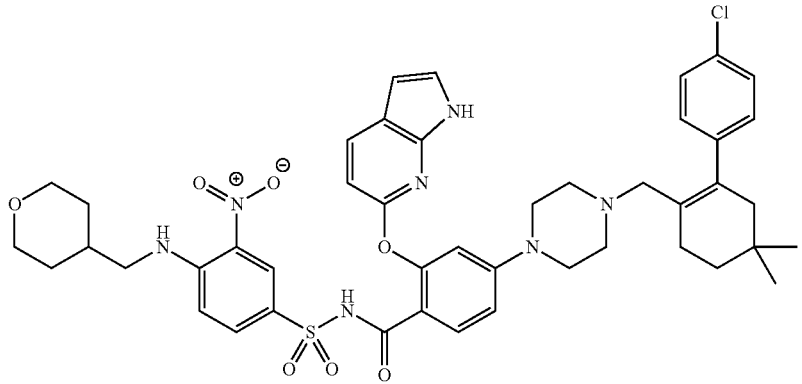

ABT-199 (shown in the free base form)

BRIEF SUMMARY OF THE INVENTION

The combined dosing of imetelstat sodium and ABT-199 in AML cells provides a novel treatment for hematologic cancers and specifically AML. Imetelstat sodium is currently being investigated clinically in myeloid fibrosis (MF) and myelodysplastic syndrome (MDS). ABT-199 is FDA approved in CLL and is also being investigated in AML.

When administered in combination, these two agents can promote apoptosis in cancer cells. When administered in combination these two agents can treat cancer in a subject in need thereof.

Accordingly, one embodiment of the invention is a method of treating a hematological cancer comprising administering a telomerase inhibitor and a Bcl-2 inhibitor in combination to a subject in need thereof.

In an embodiment of the method, the telomerase inhibitor is imetelstat. In another embodiment, the imetelstat is imetelstat sodium. The imetelstat or imetelstat sodium may be administered for 1, 2, 3, 4, 5, 6, 7, 8 or more than 8 dosage cycles, each cycle comprising: (a) intravenous administration of about 7-10 mg/kg imetelstat once every four weeks;

cell lymphoma; marginal zone lymphomas; post-transplant lymphoproliferative disorders; HIV-associated lymphomas; primary effusion lymphoma; intravascular large B-cell lymphoma; primary cutaneous primary cutaneous B-cell lymphoma; hairy cell leukemia; monoclonal gammopathy of unknown significance; smoldering multiple myeloma; and solitary plasmacytomas (solitary bone and extramedullary). In one embodiment, the hematological cancer is acute myeloid leukemia. Accordingly, one embodiment of the invention is a method of treating acute myeloid leukemia comprising administering imetelstat and ABT-199 to a subject having acute myeloid leukemia.

Another embodiment of the invention is a method of inducing apoptosis in a hematologic cancer cell comprising contacting the cell with a therapeutically effective amount of a telomerase inhibitor and contacting the cell with a therapeutically effective amount of a Bcl-2 inhibitor. In certain embodiments, the telomerase inhibitor is imetelstat or imetelstat sodium. In certain embodiments, particularly where imetelstat is used, the Bcl-2 inhibitor is ABT-199. In certain embodiments, the hematological cancer cell is selected from the following types of hematological cancer:

acute myeloid leukemia; essential thrombocythemia; polycythemia vera; primary myelofibrosis; systemic mastocytosis; chronic myeloid leukemia; chronic neutrophilic leukemia; chronic eosinophilic leukemia; refractory anemia with ringed sideroblasts; refractory cytopenia with multilineage dysplasia; refractory anemia with excess blasts; type 1; refractory anemia with excess blasts; type 2; myelodysplastic syndrome (MDS) with isolated del (5q); MDS unclassifiable; chronic myelomonocytic leukemia (CML); atypical chronic myeloid leukemia; juvenile myelomonocytic leukemia; myeloproliferative/myelodysplastic syndromes—unclassifiable; B lymphoblastic leukemia/lymphoma; T lymphoblastic leukemia/lymphoma; diffuse large B-cell lymphoma; primary central nervous system lymphoma; primary mediastinal B-cell lymphoma; Burkitt lymphoma/leukemia; follicular lymphoma; chronic lymphocytic leukemia (CLL)/small lymphocytic lymphoma; B-cell prolymphocytic leukemia; lymphoplasmacytic lymphoma/Waldenstrim macroglobulinemia; Mantle cell lymphoma; marginal zone lymphomas; post-transplant lymphoproliferative disorders; HIV-associated lymphomas; primary effusion lymphoma; intravascular large B-cell lymphoma; primary cutaneous primary cutaneous B-cell lymphoma; hairy cell leukemia; monoclonal gammopathy of unknown significance; smoldering multiple myeloma; and solitary plasmacytomas (solitary bone and extramedullary). In one embodiment, the hematological cancer cell is an acute myeloid leukemia (AML) cell.

The method of inducing apoptosis may be carried out in vivo or in vitro. Accordingly, one embodiment of the invention is an in vitro method of inducing apoptosis in an acute myeloid leukemia (AML) cell comprising: contacting the cell with a therapeutically effective amount of imetelstat sodium; and contacting the cell with a therapeutically effective amount of ABT-199. In another embodiment, the method comprises administering the therapeutically effective amounts of the telomerase inhibitor and the Bcl-2 inhibitors to a subject having a hematological cancer.

Another embodiment of the invention is a kit comprising: a dose of a telomerase inhibitor (e.g. imetelstat), in an amount effective, when administered, to induce apoptosis in a hematologic cancer cell; and a dose of a Bcl-2 inhibitor (e.g. ABT-199), in an amount effective, when administered, to induce apoptosis in a hematologic cancer cell. In yet another embodiment, the invention is directed to a pharmaceutical composition comprising imetelstat or imetelstat sodium and ABT-199. The composition may be formulated for treatment of acute myeloid leukemia.

The invention also encompasses using imetelstat or imetelstat sodium for treating a hematological cancer in a patient undergoing BCL inhibition therapy. In another embodiment, the invention is directed to using ABT-199 for treating a hematological cancer in a patient undergoing telomerase inhibition therapy.

Alternate embodiments of the invention are directed to: (1) a telomerase inhibitor (e.g. imetelstat or imetelstat sodium) for use in a method of treating hematological cancer, the method comprising administering the telomerase inhibitor and a Bcl-2 inhibitor (e.g. ABT-199) in combination to a subject in need thereof; or (2) a combination comprising a telomerase inhibitor (e.g. imetelstat or imetelstat sodium) and a Bcl-2 inhibitor (e.g. Bcl-2) for use in a method of treating hematological cancer, the method comprising administering the combination to a subject in need thereof. In these embodiments, the hematological cancer may be acute myeloid leukemia. Alternatively, the hematological cancer is selected from: acute myeloid leukemia (AML); essential thrombocythemia; polycythemia vera; primary myelofibrosis; systemic mastocytosis; chronic myeloid leukemia; chronic neutrophilic leukemia; chronic eosinophilic leukemia; refractory anemia with ringed sideroblasts; refractory cytopenia with multilineage dysplasia; refractory anemia with excess blasts; type 1; refractory anemia with excess blasts; type 2; myelodysplastic syndrome (MDS) with isolated del (5q); MDS unclassifiable; chronic myelomonocytic leukemia (CML); atypical chronic myeloid leukemia; juvenile myelomonocytic leukemia; myeloproliferative/myelodysplastic syndromes—unclassifiable; B lymphoblastic leukemia/lymphoma; T lymphoblastic leukemia/lymphoma; diffuse large B-cell lymphoma; primary central nervous system lymphoma; primary mediastinal B-cell lymphoma; Burkitt lymphoma/leukemia; follicular lymphoma; chronic lymphocytic leukemia (CLL)/small lymphocytic lymphoma; B-cell prolymphocytic leukemia; lymphoplasmacytic lymphoma/Waldenstrim macroglobulinemia; Mantle cell lymphoma; marginal zone lymphomas; post-transplant lymphoproliferative disorders; HIV-associated lymphomas; primary effusion lymphoma; intravascular large B-cell lymphoma; primary cutaneous primary cutaneous B-cell lymphoma; hairy cell leukemia; monoclonal gammopathy of unknown significance; smoldering multiple myeloma, and solitary plasmacytomas (solitary bone and extramedullary). In these embodiments, the combination of telomerase inhibitor and Bcl-2 inhibitor induces apoptosis of hematologic cancer cells.

Additional embodiments of the invention are directed to: (1) imetelstat sodium for use in a method of treating acute myeloid leukemia (AML), the method comprising administering imetelstat sodium and ABT-199 in combination to a subject in need thereof; (2) ABT-199 for use in a method of treating acute myeloid leukemia (AML), the method comprising administering ABT-199 and imetelstat sodium in combination to a subject in need thereof; or (3) a combination comprising imetelstat sodium and ABT-199 for use in a method of treating acute myeloid leukemia (AML), the method comprising administering the combination to a subject in need thereof. In these embodiments, the imetelstat sodium is for administration for 1, 2, 3, 4, 5, 6, 7, 8 or more than 8 dosage cycles, each cycle comprising: (a) intravenous administration of about 7-10 mg/kg imetelstat sodium once every four weeks; (b) intravenous administration of about 7-10 mg/kg imetelstat sodium once weekly for four weeks; (c) intravenous administration of about 2.5-7 mg/kg imetelstat sodium once every three weeks; or (d) intravenous administration of about 0.5-9.4 mg/kg imetelstat sodium once every four weeks. Additionally in these embodiments, the ABT-199 is for administration at a dose of: (a) about 50-400 mg ABT-199 daily; (b) about 2 mg ABT-199 on day 1 with daily escalation to a final dose of about 800 mg on day 6 and daily thereafter; or (c) about 25 mg ABT-199 on day 1 with daily escalation to a final dose of about 400 mg on day 5 and daily thereafter. Also in these embodiments, the administration of ABT-199 may be one day before, one day after, or the same day as, the administration of imetelstat sodium.

BRIEF DESCRIPTION OF THE DRAWINGS

FIGS. 1A and 1B show the effects of treating KG-1 cells with imetelstat sodium and/or ABT-199 for 48 hours. FIG. 1A shows dot plots of KG-1 cells after 48 hour treatment with various concentrations of ABT-199 and/or imetelstat sodium and staining with Annexin V and Propidium iodide. FIG. 1B shows a graph of % apoptotic cells as a concentration of compound for 48 hour treatment of KG-1 cells with various concentrations of ABT-199 and/or imetelstat sodium. Apoptotic cells are double labeled with Annexin V and Propidium iodide.

FIGS. 2A and 2B show the effects of treating KG-1 cells with imetelstat sodium and/or ABT-199 for 96 hours. FIG. 2A shows dot plots of KG-1 cells after 96 hour treatment with various concentrations of ABT-199 and/or imetelstat sodium and staining with Annexin V and Propidium iodide. FIG. 2B shows a graph of % apoptotic cells as a concentration of compound for 96 hour treatment of KG-1 cells with various concentrations of ABT-199 and/or imetelstat sodium. Apoptotic cells are double labeled with Annexin V and Propidium iodide.

FIGS. 3A and 3B show the effects of treating KG-1 cells with mismatch or non-complimentary oligonucleotides and ABT-199 for 48 hours FIG. 3A shows dot plots of KG-1 cells after 48 hour treatment with various concentrations of ABT-199 and/or control oligonucleotides and staining with Annexin V and Propidium iodide. FIG. 3B shows a graph of % apoptotic cells as a concentration of compound for 48 hour treatment of KG-1 cells with various concentrations of ABT-199 and/or Control oligonucleotides. Non-Comp refers to the non-complimentary control oligonucleotide. Apoptotic cells are double labeled with Annexin V and Propidium iodide.

FIG. 4A shows dot plots of KG-1 cells after 96 hour treatment with various concentrations of ABT-199 and/or control oligonucleotides and staining with Annexin V and Propidium iodide. FIG. 4B shows a graph of % apoptotic cells as a concentration of compound for 48 hour treatment of KG-1 cells with various concentrations of ABT-199 and/or Control oligonucleotides. Non-Comp refers to the non-complimentary control oligonucleotide. Apoptotic cells are double labeled with Annexin V and Propidium iodide.

FIG. 5A shows dot plots of MOLM-13 cells after 48 hour treatment with various concentrations of ABT-199 and/or imetelstat sodium and staining with Annexin V and Propidium iodide. FIG. 5B shows a graph of % apoptotic cells as a concentration of compound for 48 hour treatment of MOLM-13 cells with various concentrations of ABT-199 and/or imetelstat sodium. Apoptotic cells are double labeled with Annexin V and Propidium iodide.

FIGS. 6A and 6B show the effects of treating MOLM-13 cells with imetelstat sodium and/or ABT-199 for 48 hours. FIG. 6A shows dot plots of MOLM-13 cells after 96 hour treatment with various concentrations of ABT-199 and/or imetelstat sodium and staining with Annexin V and Propidium iodide. FIG. 6B shows a graph of % apoptotic cells as a concentration of compound for 96 hour treatment of MOLM-13 cells with various concentrations of ABT-199 and/or imetelstat sodium. Apoptotic cells are double labeled with Annexin V and Propidium iodide.

FIGS. 7A and 7B show the effects of treating MOLM-13 cells with various concentrations of ABT-199 and/or control oligonucleotide for 48 hours. FIG. 7A shows dot plots of MOLM-13 cells after 48 hour treatment with various concentrations of ABT-199 and/or control oligonucleotides and staining with Annexin V and Propidium iodide. FIG. 7B shows a graph of % apoptotic cells as a concentration of compound for 48 hour treatment of MOLM-13 cells with various concentrations of ABT-199 and/or Control oligonucleotides. Non-Comp refers to the non-complimentary control oligonucleotide. Apoptotic cells are double labeled with Annexin V and Propidium iodide.

FIGS. 8A and 8B show the effects of treating MOLM-13 cells with various concentrations of ABT-199 and/or control oligonucleotides for 96 hours. FIG. 8A shows dot plots of MOLM-13 cells after 96 hour treatment with various concentrations of ABT-199 and/or control oligonucleotides and staining with Annexin V and Propidium iodide. FIG. 8B shows a graph of % apoptotic cells as a concentration of compound for 96 hour treatment of MOLM-13 cells with various concentrations of ABT-199 and/or Control oligonucleotides. Non-Comp refers to the non-complimentary control oligonucleotide. Apoptotic cells are double labeled with Annexin V and Propidium iodide.

FIG. 12A shows a graph of % apoptotic cells as a concentration of compound for 48 hour treatment of MOLM-13 cells with various concentrations of ABT-199 and/or control Mismatch oligonucleotide "Mismatch". FIG. 12B shows a graph of % apoptotic cells as a concentration of compound for 48 hour treatment of MOLM-13 cells with various concentrations of ABT-199 and/or control Non-complimentary oligonucleotide "Non-comp". Apoptotic cells are double labeled with Annexin V and Propidium iodide.

FIGS. 14A and 14B show the % apoptotic cells as a concentration of compound for 48 hour treatment of MOLM-13 cells with various concentrations of ABT-199, control Mismatch oligonucleotide and Non-complimentary oligonucleotide. FIG. 14A shows a graph of % apoptotic cells as a concentration of compound for 96 hour treatment of MOLM-13 cells with various concentrations of ABT-199 and/or control Mismatch oligonucleotide "Mismatch". FIG. 14B shows a graph of % apoptotic cells as a concentration of compound for 96 hour treatment of MOLM-13 cells with various concentrations of ABT-199 and/or control Non-complimentary oligonucleotide "Non-comp". Apoptotic cells are double labeled with Annexin V and Propidium iodide.

FIGS. 15A-15D show mean responses of four PBMC (peripheral blood mononuclear cell) samples purified from whole blood of AML patients and exposed ex vivo to treatment of ABT-199 and/or imetelstat sodium at various concentrations for 16- and 40-hours, and analyzed for cell viability by flow cytometry assay staining with Annexin V and Propidium Iodide. FIG. 15A and FIG. 15B show graphs of % viable cells as a concentration of compound for 16 hours of treatment of AML patient whole blood Ficoll purified PBMCs with various concentrations of ABT-199 and/or imetelstat sodium. FIG. 15A shows the results for $CD45^+$ leukocytes. FIG. 15B shows the results for $CD45^+$/$CD34^+$ leukemic stem cells. FIG. 15C and FIG. 15D show graphs of % viable cells as a concentration of compound for 40 hours of treatment of AML patient whole blood Ficoll purified PBMCs with various concentrations of ABT-199 and/or imetelstat sodium. FIG. 15C shows the results for $CD45^+$ leukocytes. FIG. 15D shows the results for $CD45^+$/$CD34^+$ leukemic stem cells. In FIGS. 15A-15D, error bars represent standard deviations. Viable cells remaining after treatment are unlabeled with either Annexin V or Propidium Iodide.

FIG. 16 shows the percent survival of mice as a function of days post-tumor cell implantation. The mice were treated for 31 days with: (i) Vehicles (MM+PEG400/Phosal50/ETOH); (ii) imetelstat sodium (30 mg/kg), (iii) ABT-199 (100 mg/kg), (iv) MM (mismatched oligo) (30 mg/kg) and ABT-199 (100 mg/kg); and (v) imetelstat sodium (30 mg/kg) and ABT-199 (100 mg/kg).

FIG. 17A shows the apoptotic population (double label) at 96 hours after single dose of treatment with imetelstat sodium for MOLM-13. FIG. 17B shows the apoptotic population (double label) at 96 hours after single dose of treatment with imetelstat sodium for AML cell line HL-60.

DETAILED DESCRIPTION OF THE INVENTION

Figure 1B:
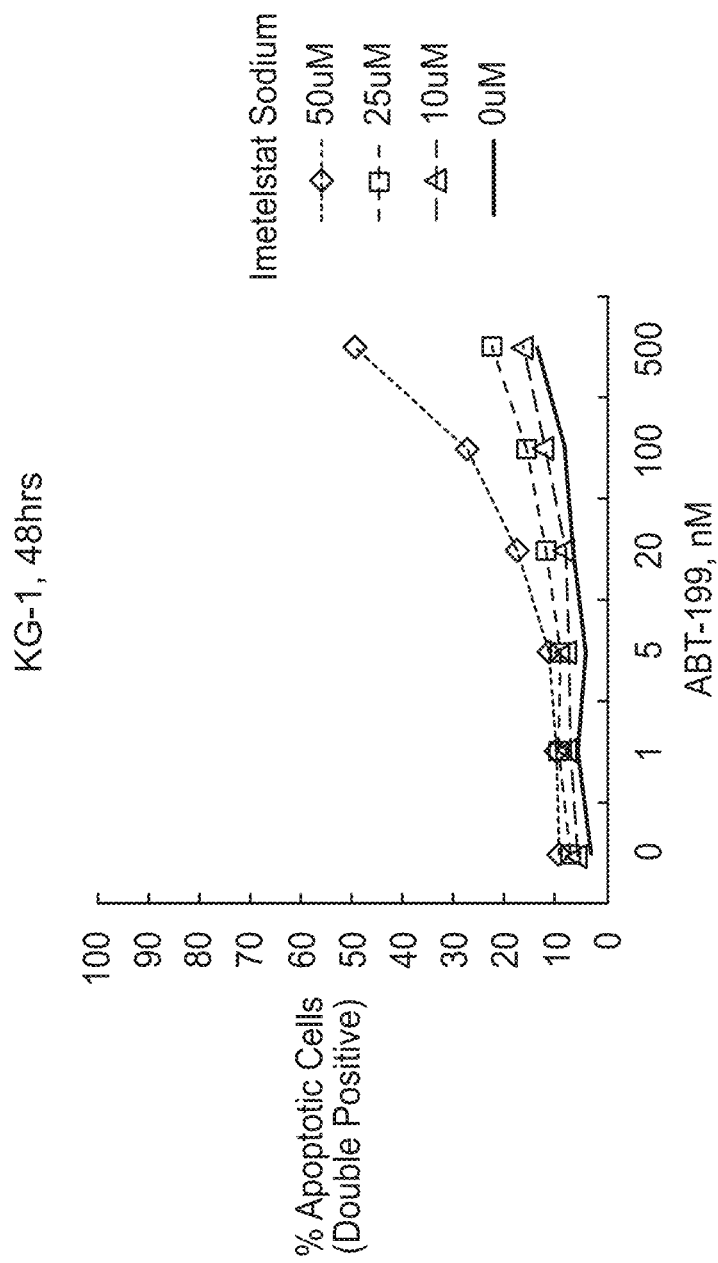

The following detailed description of the invention will be better understood when read in conjunction with the appended figures. Figures are provided for illustrating certain embodiments of the invention. However, the invention is not limited to the precise arrangements, examples, and instrumentalities shown. For clarity of disclosure, and not by way of limitation, the detailed description of the invention is divided into subsections that describe or illustrate certain features, embodiments or applications of the present invention.

The invention provides methods of treating hematological cancers with a combination of a telomerase inhibitor and a Bcl-2 inhibitor. Drug resistant cell populations can lead to incomplete response to treatment or relapse of disease. The present invention provides the combination of a telomerase inhibitor and a Bcl-2 inhibitor which work synergistically to induce greater levels of apoptosis in AML cells than either drug can induce independently. The invention provides a method of inducing apoptosis in a hematologic cancer cell comprising contacting the cell with a therapeutically effective amount of a telomerase inhibitor and a therapeutically effective amount of a Bcl-2 inhibitor. In some embodiments, the telomerase inhibitor is imetelstat. In some embodiments, the Bcl-2 inhibitor is ABT-199. In some embodiments, the hematological cancer is AML.

In certain instances, the combination provides an enhanced inhibiting effect relative to either component alone; in some cases, the combination provides a supraadditive or synergistic effect relative to the combined or additive effects of the components.

In some embodiments, the method is a method of inducing apoptosis in a hematologic cancer cell. The subject method can include contacting the cell with a therapeutically effective amount of a telomerase inhibitor, and contacting the cell with a therapeutically effective amount of a Bcl-2 inhibitor. In certain embodiments, the telomerase inhibitor is imetelstat. In some embodiments, the telomerase inhibitor is imetelstat sodium. In some embodiments, the Bcl-2 inhibitor is ABT-199. The contacting of the cell with the telomerase inhibitor can be performed before, during and/or after the contacting of the cell with the Bcl-2 inhibitor. The contacting of the cell with the telomerase inhibitor and the Bcl-2 inhibitor can be performed simultaneous or sequentially.

In an embodiment, the telomerase inhibitor is an oligonucleotide with telomerase inhibiting activity, in particular an oligonucleotide as defined in WO 2005/023994 and/or WO 2014/088785, both of which are herein incorporated by reference.

In general, various combinations of the telomerase inhibitor and the Bcl-2 inhibitor may be employed, used either sequentially or simultaneously. For multiple dosages, the two agents may directly alternate, or two or more doses of one agent may be alternated with a single dose of the other agent, for example. Simultaneous administration of both agents may also be alternated or otherwise interspersed with dosages of the individual agents. In some cases, the time between dosages may be for a period from about 1-6 hours, to about 6-12 hours, to about 12-24 hours, to about 1-2 days, to about 1-2 week or longer following the initiation of treatment. During a course of treatment, the need to complete the planned dosings may be re-evaluated.

The term "apoptosis" refers to the process of programmed cell death, with its accompanying cellular morphological changes and loss of cell viability. In one embodiment, the method of inducing apoptosis provides a method for treating a neoplastic disorder in a vertebrate organism.

In the context of this method, the term "inducing" means a direct or indirect causal relationship. Thus, the presence and/or maintenance of a particular condition causes or leads to the induced result.

As used herein, the term "about" when referring to a measurable value such as an amount, a temporal duration, and the like, is meant to encompass variations of between ±20% and ±0.1%, preferably ±20% or ±10%, more preferably ±5%, even more preferably ±1%, and still more preferably ±0.1% from the specified value, as such variations are appropriate to perform the disclosed methods.

As used throughout "AML" refers to acute myeloid leukemia.

A. Treatment

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The present disclosure provides a treatment (for hematological cancers such as acute myeloid leukemia) comprising combining the administration of the telomerase inhibitor imetelstat sodium with the administration of the Bcl-2 inhibitor ABT-199. The subject method of treatment can be more efficacious and produce a greater response to treatment in patients with AML than is observed using either drug alone. In one embodiment, the method of treatment comprises administering a telomerase inhibitor and a Bcl-2 inhibitor in combination to a subject in need of treatment for hematological cancer. In another embodiment, the hematological cancer is AML. In another embodiment, the telomerase inhibitor is imetelstat. In certain embodiments, the telomerase inhibitor is imetelstat sodium. In another embodiment, the Bcl-2 inhibitor is ABT-199.

In some embodiments, the dose of telomerase inhibitor administered to the subject is an amount sufficient to treat the disease when the telomerase inhibitor thereof is used alone. In certain embodiments, the dose of telomerase inhibitor administered to the subject is less than the amount sufficient to treat the disease when the telomerase inhibitor is used alone. In one embodiment, the dose of telomerase inhibitor is reduced when used in combination with ABT-199 in treatment of a subject who has been diagnosed with AML. In some embodiments the telomerase inhibitor is imetelstat. In some embodiments the telomerase inhibitor is imetelstat sodium. In some embodiments, the dose of Bcl-2 inhibitor administered to the subject is an amount sufficient to treat the disease when the Bcl-2 inhibitor is used alone. In certain embodiments, the dose of Bcl-2 inhibitor administered to the subject is less than the amount sufficient to treat the disease when the Bcl-2 inhibitor is used alone. In some embodiments the Bcl-2 inhibitor is ABT-199. In another embodiment, the dose of Bcl-2 inhibitor is reduced when used in combination with imetelstat in treatment of a subject who has been diagnosed with AML. In still another embodiment, the doses of imetelstat thereof and ABT-199 are both reduced when used in combination in treatment of a subject who has been diagnosed with AML In another embodiment, the length of treatment with a telomerase inhibitor is reduced when used in combination with a Bcl-2 inhibitor in treatment of a subject who has a hematological cancer. In another embodiment, the length of treatment with imetelstat is reduced when used in combination with ABT-199 in treatment of a subject with a hematological cancer. In another embodiment, the length of treatment with ABT-199 is reduced when used in combination with imetelstat in treatment of a subject who has been diagnosed with a hematological cancer. In another embodiment, the length of treatment with both imetelstat and ABT-199 is reduced when used in combination in treatment of a subject who has been diagnosed with a hematological cancer. In some embodiments the hematological cancer is AML.

The combinations of drugs described herein may be administered to the subject as a composition containing both drugs, or separately. The combinations of drugs described herein may be administered in a combined-drug composition, e.g., by IV administration, or separately.

B. Hematological Cancers

The methods of the present invention can be used for treatment of any convenient hematological malignancy. Hematologic malignancies are forms of cancer that begin in the cells of blood-forming tissue, such as the bone marrow, or in the cells of the immune system. Examples of hematologic cancers are acute and chronic leukemias, lymphomas, multiple myeloma and myelodysplastic syndromes. In some instances, the hematological malignancy is referred to as a hematological cancer. Myeloproliferative neoplasms, or MPNs, are hematologic neoplasms that arise from neoplastic hematopoietic myeloid progenitor cells in the bone marrow, such as the precursor cells of red cells, platelets and granulocytes. Proliferation of neoplastic progenitor cells leads to an overproduction of any combination of white cells, red cells and/or platelets, depending on the disease. These overproduced cells may also be abnormal, leading to additional clinical complications. There are various types of chronic myeloproliferative disorders. Included in the myeloproliferative neoplasms is essential thrombocythemia, polycythemia vera, chronic myelogenous leukemia, myelofibrosis, chronic neutrophilic leukemia, chronic eosinophilic leukemia and acute myelogenous leukemia. A myelodysplastic syndrome (MDS) is a group of symptoms that includes cancer of the blood and bone marrow. MDS includes, but limited to, refractory anemia, refractory anemia with excess blasts, refractory cytopenia with multilineage dysplasia, and chronic myelomonocytic leukemia (CML).

Hematological cancers of interest include, but not limited to, AML, essential thrombocythemia, polycythemia vera, primary myelofibrosis, systemic mastocytosis, chronic myeloid leukemia, chronic neutrophilic leukemia, chronic eosinophilic leukemia, refractory anemia with ringed sideroblasts, refractory cytopenia with multilineage dysplasia, refractory anemia with excess blasts, type 1, refractory anemia with excess blasts, type 2, myelodysplastic syndrome (MDS) with isolated del (5q), MDS unclassifiable, chronic myelomonocytic leukemia (CML), atypical chronic myeloid leukemia, juvenile myelomonocytic leukemia, myeloproliferative/myelodysplastic syndromes—unclassifiable, B lymphoblastic leukemia/lymphoma, T lymphoblastic leukemia/lymphoma, diffuse large B-cell lymphoma, primary central nervous system lymphoma, primary mediastinal B-cell lymphoma, Burkitt lymphoma/leukemia, follicular lymphoma, chronic lymphocytic leukemia (CLL)/small lymphocytic lymphoma, B-cell prolymphocytic leukemia, lymphoplasmacytic lymphoma/Waldenstrim macroglobulinemia, Mantle cell lymphoma, marginal zone lymphomas, post-transplant lymphoproliferative disorders, HIV-associated lymphomas, primary effusion lymphoma, intravascular large B-cell lymphoma, primary cutaneous B-cell lymphoma, hairy cell leukemia, monoclonal gammopathy of unknown significance, smoldering multiple myeloma, and solitary plasmacytomas (solitary bone and extramedullary).

Certain treatment regimens of the invention are particularly suited for treatment of AML. In certain embodiments of the invention the subject to whom treatment is administered has AML. Among AMLs, chemotherapy-refractory AMLs, such as AMLs refractory to treatment with cytarabine in combination with daunorubicin or idarubicin can be treated using the methods disclosed herein, e.g., by administration of imetelstat in combination with ABT-199. Response of AML to treatment is known in the art. An example of AML Response Assessment is shown in Table 1.

TABLE 1

AML Response Assessments
AML Response Assessments

| Category | Definition |
| --- | --- |
| Complete response (CR)[1] | Bone marrow blasts <5%; absence of blasts with Auer rods; absence of extramedullary disease; absolute neutrophil count >1.0 × $10^9$/L (1000/μL); platelet count >100 × $10^9$/L (100 000/μL); independence of red cell transfusions |
| CR with incomplete recovery (CRi)[2] | All CR criteria except for residual neutropenia (<1.0 × $10^9$/L [1000/μL]) or thrombocytopenia (<100 × $10^9$/L [100 000/μL]) |
| Morphologic leukemia-free state[3] | Bone marrow blasts <5%; absence of blasts with Auer rods; absence of extramedullary disease; no hematologic recovery required |
| Partial response (PR) | Relevant in the setting of Phase 1 and 2 clinical trials only; all hematologic criteria of CR; decrease of bone marrow blast percentage to 5% to 25%; and decrease of pretreatment bone marrow blast percentage by at least 50% |
| Cytogenetic CR (CRc)[4] | Reversion to a normal karyotype at the time of morphologic CR (or CRi) in cases with an abnormal karyotype at the time of diagnosis; based on the evaluation of 20 metaphase cells from bone marrow |
| Molecular CR (CRm)[5] | No standard definition; depends on molecular target |
| Relapse[6] | Bone marrow blasts ≥5%; or reappearance of blasts in the blood; or development of extramedullary disease |
| Treatment failure[7] | >25% absolute increase in the bone marrow blast count from baseline to the present assessment (e.g., from 20% to 46%) on bone marrow aspirate (or biopsy in case of dry tap) |
| Stable disease[8] | Does not qualify for a complete or partial response and has no evidence of treatment failure. |

Definitions of response criteria are based primarily on those given by Cheson 1990.
[1]All criteria need to be fulfilled; marrow evaluation should be based on a count of 200 nucleated cells in an aspirate with spicules; if ambiguous, consider repeat exam after 5 to 7 days; flow cytometric evaluation may help to distinguish between persistent leukemia and regenerating normal marrow; a marrow biopsy should be performed in cases of dry tap, or if no spicules are obtained; no minimum duration of response required.
[2]The criterion of CRi is of value in protocols using intensified induction or double induction strategies, in which hematologic recovery is not awaited, but intensive therapy will be continued. In such protocols, CR may even not be achieved in the cycle of the entire treatment plan. In these instances, the overall response rate should include CR and CRi patients. Some patients may not achieve complete hematologic recovery upon longer observation times.
[3]This category may be useful in the clinical development of novel agents within phase 1 clinical trials, in which a transient morphologic leukemia-free state may be achieved at the time of early response assessment.
[4]Four studies showed that failure to convert to a normal karyotype at the time of CR predicts inferior outcome.
[5]As an example, in CBF AML low-level PCR-positivity can be detected in patients even in long-term response. Normalizing to 104 copies of ABL1 in accordance with standardized criteria, transcript levels below 12 to 10 copies appear to be predictive for long-term response.
[6]In cases with low blast percentages (5-10%), a repeat marrow should be performed to confirm relapse. Appearance of new dysplastic changes should be closely monitored for emerging relapse. In a patient who has been recently treated, dysplasia or a transient increase in blasts may reflect a chemotherapy effect and recovery of hematopoiesis. Cytogenetics should be tested to distinguish true relapse from therapy-related MDS/AML.

The combinations of drugs described herein are suitable for use in the treatment of any one of the diseases or disorders mentioned herein, including hematological cancer (or subtypes thereof). The drugs could be administered simultaneously or sequentially.

The combinations of drugs described herein are suitable for use in inducing apoptosis in a hematologic cancer cell. The drugs could be administered simultaneously or sequentially.

It will also be clear that the compositions described herein are suitable for use in the treatment of any one of the diseases or disorders mentioned herein, including hematological cancer (or subtypes thereof).

C. Subject

A subject is a mammal in need of treatment for cancer. Generally, the subject is a human patient. In some embodiments of the invention, the subject can be a non-human mammal such as a non-human primate, an animal model (e.g., animals such as mice and rats used in screening, characterization and evaluation of medicaments) and other mammals. As used herein, the terms patient, subject and individual are used interchangeably.

D. Anti-Cancer Agents

The following section describes drugs used in various embodiments of the invention. As these drugs are well known, only brief discussions are provided. Publications cited in this section are intended to illustrate aspects of the drug for the benefit of the practitioner; however, citation to a particular publication in this section or elsewhere in this disclosure is not intended to limit the present invention in any respect, including as to doses, combinations, and indications.

1. Telomerase Inhibitors

Examples of telomerase inhibitors include, without limitation, imetelstat, specifically imetelstat sodium. In some cases, one or more than one telomerase inhibitor (e.g., two or three telomerase inhibitors) can be administered to a mammal to treat a hematological malignancy.

Imetelstat sodium is the sodium salt of imetelstat, which is a synthetic lipid-conjugated, 13-mer oligonucleotide N3→*P5'-thio-phosphoramidate. The chemical name for imetelstat sodium is: DNA, d(3'-amino-3'-deoxy-P-thio) (T-A-G-G-G-T-T-A-G-A-C-A-A), 5'-[O-[2-hydroxy-3-(hexadecanoylamino)propyl] phosphorothioate], sodium salt (1:13) (SEQ ID NO: 1). Imetelstat and imetelstat sodium can be produced, formulated, or obtained as described elsewhere (Asai et al., Cancer Res., 63(14):3931-3939 (2003), Herbert et al., Oncogene, 24:5262-5268 (2005), and Gryaznov, Chem. Biodivers., 7:477-493 (2010)).

Imetelstat and imetelstat sodium targets the RNA template of telomerase and has been shown to inhibit telomerase activity and cell proliferation in various cancer cell lines and tumor xenografts in mice. Phase 1 studies involving patients with breast cancer, non-small-cell lung cancer and other solid tumors, multiple myeloma, or chronic lymphocytic leukemia have provided information on drug pharmacokinetics and pharmacodynamics and helped establish 9.4 mg per kilogram of body weight (given as a 2-hour intravenous infusion). A subsequent phase 2 study involving patients with essential thrombocythemia showed platelet-lowering activity accompanied by a significant reduction in JAK2 V617F and CALR mutant allele burdens. Imetelstat sodium is routinely administered intravenously; it is contemplated that in the practice of the present invention other administration routes also can be used, such as intrathecal administration, intratumoral injection, oral administration and others. Imetelstat sodium can be administered at doses comparable to those routinely utilized clinically. In preferred embodiments, imetelstat sodium is administered as described elsewhere herein.

A particular embodiment is according to any one of the other embodiments, wherein imetelstat is limited to imetelstat sodium.

2. Bcl-2 Inhibitor ABT-199

ABT-199 (venetoclax) represents the first-in-class, selective, oral BCL-2 inhibitor sparing platelets (FIG. 1B). It showed sub-nanomolar affinity to BCL-2 (K i<0.010 nM) with antitumor activity against non-Hodgkin's lymphoma (NHL) and CLL in vitro. In vivo mouse xenograft studies showed activity against aggressive (Myc+) lymphomas as well as acute leukemia. A phase Ia trial of ABT-199 in R/R NHL used continuous daily dosing of 200-900 mg. A single dose was administered on day 7 followed by a lead-in period with stepwise upward titration over 2-3 weeks. The single-agent ABT-199 was also studied in a phase 2, open-label, multicenter trial in patients with high-risk R/R AML and in untreated patients who were unfit for intensive chemotherapy. The study allowed intra-patient dose escalation when a patient received 20 mg ABT-199 on week (Wk) 1 day 1. Daily escalation was implemented to target a final dose of 800 mg on day 6 and daily thereafter. Those patients without a Complete Response (CR) or CR with incomplete hematological recovery (CRi) at the first scheduled assessment (end of Wk 4) were able to escalate to 1200 mg. The recommended Phase 2 dose of ABT-199 in combination with rituximab is 400 mg daily.

E. Pharmaceutical Compositions

The present invention also concerns pharmaceutical compositions comprising a telomerase inhibitor (e.g., imetelstat, in particular imetelstat sodium) and a Bcl-2 inhibitor (e.g., ABT-199). In one embodiment, the pharmaceutical composition comprises imetelstat, in particular imetelstat sodium, and ABT-199. In one embodiment, the pharmaceutical composition comprises imetelstat, in particular, imetelstat-sodium and ABT-199. The combinations of drugs described herein may be administered to the subject as a composition containing both drugs.

The carrier or diluent must be "acceptable" in the sense of being compatible with the other ingredients of the composition and not deleterious to the recipients thereof.

For ease of administration, the combinations of drugs described herein may be formulated into various pharmaceutical forms for administration purposes. The combinations of drugs described herein may be formulated into various pharmaceutical forms for administration purposes. As appropriate compositions there may be cited all compositions usually employed for systemically administering drugs.

To prepare the pharmaceutical compositions of this invention, an effective amount of a combination of drugs described herein are combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. In some cases, administration can be via intravenous injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing combination of drugs described herein may be formulated in oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredients calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the drugs in the combinations described herein in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also cosolvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the drugs in the combinations described herein, and from 1 to 99.95% by weight, more preferably from 30 to 99.9% by weight, even more preferably from 50 to 99.9% by weight of a pharmaceutically acceptable carrier, all percentages being based on the total weight of the composition.

The frequency of administration can be any frequency that reduces the severity of a symptom of a hematological malignancy (e.g., reduces or reverses bone marrow fibrosis) without producing significant toxicity to the mammal. For example, the frequency of administration can be from about once every two months to about once a week, or from about once a month to about twice a month, or from about once every six weeks to about twice a month. The frequency of administration can remain constant or can be variable during the duration of treatment. A course of treatment with a composition containing one or more telomerase inhibitors can include rest periods. For example, a composition containing a telomerase inhibitor and a Bcl-2 inhibitor can be administered weekly over a three week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the hematological malignancy may require an increase or decrease in administration frequency.

An effective duration for administering a composition containing a telomerase inhibitor (e.g., imetelstat or imetelstat sodium) and a Bcl-2 inhibitor (e.g., ABT-199) can be any duration that reduces the severity of a symptom of a hematological malignancy (e.g., reduces or reverses bone marrow fibrosis) without producing significant toxicity to the mammal. Thus, the effective duration can vary from one month to several months or years (e.g., one month to two years, one month to one year, three months to two years, three months to ten months, or three months to 18 months). In general, the effective duration for the treatment of a hematological malignancy can range in duration from two months to twenty months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the hematological malignancy.

In certain instances, a course of treatment and the severity of one or more symptoms related to a hematological malignancy can be monitored. Any method can be used to determine whether or not the severity of a symptom of a hematological malignancy is reduced. For example, the severity of a symptom of a hematological malignancy (e.g., bone marrow fibrosis) can be assessed using biopsy techniques.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, and the like; and when the molecule contains a basic functionality, salts of organic or inorganic acids, such as hydrochloride, and the like. Pharmaceutically acceptable salts of interest include, but are not limited to, aluminum, ammonium, arginine, barium, benzathine, calcium, cholinate, ethylenediamine, lysine, lithium, magnesium, meglumine, procaine, potassium, sodium, tromethamine, N-methylglucamine, N,N'-dibenzylethylene-diamine, chloroprocaine, diethanolamine, ethanolamine, piperazine, zinc, diisopropylamine, diisopropylethylamine, triethylamine and triethanolamine salts.

The term "salt(s) thereof" means a compound formed when a proton of an acid is replaced by a cation, such as a metal cation or an organic cation and the like. Preferably, the salt is a pharmaceutically acceptable salt. By way of example, salts of the present compounds include those wherein the compound is protonated by an inorganic or organic acid to form a cation, with the conjugate base of the inorganic or organic acid as the anionic component of the salt. Salts of interest include, but are not limited to, aluminum, ammonium, arginine, barium, benzathine, calcium, cesium, cholinate, ethylenediamine, lithium, magnesium, meglumine, procaine, N-methylglucamine, piperazine, potassium, sodium, tromethamine, zinc, N,N'-dibenzylethylene-diamine, chloroprocaine, diethanolamine, ethanolamine, piperazine, diisopropylamine, diisopropylethylamine, triethylamine and triethanolamine salts. It is understood that for any of the oligonucleotide structures depicted herein that include a backbone of internucleoside linkages, such oligonucleotides may also include any convenient salt forms. In some embodiments, acidic forms of the internucleoside linkages are depicted for simplicity. In some instances, the salt of the subject compound is a monovalent cation salt. In certain instances, the salt of the subject compound is a divalent cation salt. In some instances, the salt of the subject compound is a trivalent cation salt. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include for example cis-trans isomers, E and Z isomers, enantiomers, and diastereomers. As to any of the groups disclosed herein which contain one or more substituents, it is understood, of course, that such groups do not contain any substitution or substitution patterns which are sterically impractical and/or synthetically non-feasible. All stereoisomers are intended to be included within the scope of the present disclosure.

A person of ordinary skill in the art would recognize that other tautomeric arrangements of the groups described herein are possible. It is understood that all tautomeric forms of a subject compound are encompassed by a structure where one possible tautomeric arrangement of the groups of the compound is described, even if not specifically indicated.

It is intended to include a solvate of a pharmaceutically acceptable salt of a tautomer of a stereoisomer of a subject compound. These are intended to be included within the scope of the present disclosure.

F. Administration and Administration Regimens

For treatment of hematological cancers, telomerase inhibitors (e.g., imetelstat or imetelstat sodium) and Bcl-2 inhibitors (e.g., ABT-199, ABT-263, and ABT-737) can be administered in combination to a subject in need of treatment. An example of a cancer that can be treated by this method is acute myeloid leukemia (AML), also called acute myelocytic leukemia, acute myelogenous leukemia, acute granulocytic leukemia or acute non-lymphocytic leukemia. In acute leukemia, the leukemia cells are immature blood cells (called blasts) which are fast growing and divide quickly. Without treatment, most patients with acute leukemia would live only a few months.

Telomerase inhibitors and Bcl-2 inhibitors as used in the present invention can be administered at any dose that is therapeutically effective, such as doses comparable to those routinely utilized clinically. Specific dose regimens for known and approved anti-cancer agents (e.g., the recommended effective dose) are known to physicians and are given, for example, in the product descriptions found in the PHYSICIANS' DESK REFERENCE, 2003, 57th Ed., Medical Economics Company, Inc., Oradell, N.J.; Goodman & Gilman's THE PHARMACOLOGICAL BASIS OF THERAPEUTICS" 2001, 10th Edition, McGraw-Hill, New York; and/or are available from the Federal Drug Administration and/or are discussed in the medical literature.

In some aspects, the dose of a telomerase inhibitor, imetelstat sodium, administered to the subject is about 1.0 mg/kg to about 13.0 mg/kg. In other aspects, the dose of a telomerase inhibitor is about 6.5 mg/kg to about 11.7 mg/kg. In some embodiments, the dose of a telomerase inhibitor includes at least about any of 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, or 13 mg/kg.

In some embodiments, the effective amount of a telomerase inhibitor administered to the individual includes at least about any of 1 mg/kg, 2.5 mg/kg, 3.5 mg/kg, 5 mg/kg, 6.5 mg/kg, 7.5 mg/kg, 9.4 mg/kg, 10 mg/kg, 15 mg/kg, or 20 mg/kg. In various embodiments, the effective amount of a telomerase inhibitor administered to the individual includes less than about any of 350 mg/kg, 300 mg/kg, 250 mg/kg, 200 mg/kg, 150 mg/kg, 100 mg/kg, 50 mg/kg, 30 mg/kg, 25 mg/kg, 20 mg/kg, 10 mg/kg, 7.5 mg/kg, 6.5 mg/kg, 5 mg/kg, 3.5 mg/kg, 2.5 mg/kg, 1 mg/kg, or 0.5 mg/kg of a telomerase inhibitor.

Exemplary dosing frequencies for the pharmaceutical compositions (e.g., a pharmaceutical composition including a telomerase inhibitor, and/or a pharmaceutical composition including a Bcl-2 inhibitor) include, but are not limited to, daily; every other day; twice per week; three times per week; weekly without break; weekly, three out of four weeks; once every three weeks; once every two weeks; weekly, two out of three weeks. In some embodiments, the pharmaceutical composition is administered about once every week, once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week, or three times daily, two times daily. In some embodiments, the intervals between each administration are less than about any of 6 months, 3 months, 1 month, 20 days, 15 days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

Telomerase inhibitors such as imetelstat or imetelstat sodium can be administered using any appropriate method. For example, telomerase inhibitors such as imetelstat or imetelstat sodium can be administered intravenously once every 4 weeks over a period of time (e.g., one, two, three, four, or five hours). In one embodiment, imetelstat is administered intravenously once weekly over a period of about 2 hours at 7-10 mg/kg. In another embodiment, imetelstat is administered intravenously once every 3 weeks over a period of about 2 hours at 2.5-7 mg/kg. In yet another embodiment, imetelstat is administered intravenously for a period of about 2 hours once every 4 weeks at 0.5-5 mg/kg. In another embodiment, imetelstat is administered intravenously once every 3 weeks over a period of about 2 hours at about 2.5-10 mg/kg. In yet another embodiment, imetelstat is administered intravenously for a period of about 2 hours once every 4 weeks at about 0.5-9.4 mg/kg.

In such cases, when treating with the Bcl-2 inhibitor, ABT-199, the dose of ABT-199 can be about or less than 400 mg PO qDay. For example, a human identified as having a hematological malignancy can be treated with ABT-199 at a dose that is a) 20 mg PO qday, b) 50 mg PO qDay, c) 100 mg PO qDay, d) 200 mg PO qDay or e) 400 mg PO qDay. In another embodiment, ABT-199 is administered according to a weekly ramp-up schedule over 5 weeks to the recommended daily dose of 400 mg starting at 20 mg PO qDay at week 1, 50 mg PO qDay at week 2, 100 mg PO qDay at week 3, 200 mg PO qDay at week 4 and 400 mg PO qDay at week 5 and beyond. In another embodiment, ABT-199 is administered at 400 mg PO qDay. In another embodiment, dosing is continued until disease progression or unacceptable toxicity.

It will be appreciated that treatment for cancer sometimes involves multiple "rounds" or "cycles" of administration of a drug, where each cycle comprises administration of the drug one or more times according to a specified schedule (e.g., every three weeks for three consecutive days; once per week; etc.). For example, anti-cancer drugs can be administered for from 1 to 8 cycles, or for a longer period. When more than one drug (e.g., two-drugs) is administered to a subject, each can be administered according to its own schedule (e.g., weekly; once every three weeks; etc.). It will be clear that administration of drugs, even those administered with different periodicity, can be coordinated so that both drugs are administered on the same day at least some of the time or, alternatively, so the drugs are administered on consecutive days at least some of the time.

In treatment regimens in which a telomerase inhibitor (e.g., imetelstat or imetelstat sodium) and a Bcl-2 inhibitor (e.g., ABT-199 or Veneteclax) are administered in combination, they can be administered in any order. In certain embodiments, the telomerase inhibitor is administered one day before, one day after, or the same day as, administration of the Bcl-2 inhibitor. It will be understood that other schedules can be used as determined by the physician.

As is understood in the art, treatment with cancer therapeutic drugs can be suspended temporarily if toxicity is observed, or for the convenience of the patient, without departing from the scope of the invention, and then resumed.

G. Administration in Combination

Two or three drugs are administered to a subject "in combination" when the drugs are administered as part of the same course of therapy. A course of therapy refers to administration of combinations of drugs believed by the medical professional to work together additively, complementarity, synergistically, or otherwise to produce a more favorable outcome than that anticipated for administration of a single drug. A course of therapy can be for one or a few days, but more often extends for several weeks.

Thus, an example of administration in combination is administration of imetelstat once every 28 days for 1 to 4 cycles, beginning on day 1, and administration of ABT-199 once every 7 days beginning on day 1 for 4 cycles. In an embodiment administration of ABT-199 begins on day 1, day −1, or day 2 or another day that within the cycle. In an embodiment, administration in combination is administration of imetelstat once every 28 days for 1 to 4 cycles, beginning on day 1, and administration of ABT-199 once every day for 28 days beginning on day 1 for 1 to 4 cycles.

When two drugs are administered in combination, a variety of schedules can be used. In one case, for example and without limitation, Drug 1 is first administered prior to administration of Drug 2, and treatment with Drug 1 is continued throughout the course of administration of Drug 2; alternatively Drug 1 is administered after the initiation or completion of Drug 2 therapy; alternatively, Drug 1 is first administered contemporaneously with the initiation of the other cancer therapy. As used in this context, "contemporaneously" means the two drugs are administered the same day, or on consecutive days.

Although in principle certain drugs can be co-formulated, in general they are administered in separate compositions. Similarly, although certain drugs can be administered simultaneously, more often (especially for drugs administered by infusion) drugs are administered at different times on the same day, on consecutive days, or according to another schedule.

The invention also relates to a combination comprising a telomerase inhibitor and a Bcl-2 inhibitor. In particular, the telomerase inhibitor is imetelstat and the Bcl-2 inhibitor is ABT-199. In particular, the telomerase inhibitor is imetelstat sodium and the Bcl-2 inhibitor is ABT-199.

The invention also relates to a combination comprising a telomerase inhibitor and a Bcl-2 inhibitor for use as a medicament. In particular, the telomerase inhibitor is imetelstat and the Bcl-2 inhibitor is ABT-199. In particular, the telomerase inhibitor is imetelstat sodium and the Bcl-2 inhibitor is ABT-199.

H. Diagnosis

For diagnosis of AML, blood and marrow smears are morphologically examined using a May-Grünwald-Giemsa or a Wright-Giemsa stain. It is recommended that at least 200 leukocytes on blood smears and 500 nucleated cells on marrow smears be counted, with the latter containing spicules. For a diagnosis of AML, a marrow or blood blast count of 20% or more is required, except for AML with t(15;17), t(8;21), inv(16) or t(16;16), and some cases of erythroleukemia. Myeloblasts, monoblasts, and megakaryoblasts are included in the blast count. In AML with monocytic or myelomonocytic differentiation, monoblasts and promonocytes, but not abnormal monocytes, are counted as blast equivalents. Erythroblasts are not counted as blasts except in the rare instance of pure erythroid leukemia.

I. Kits

The present invention also relates to a kit comprising a telomerase inhibitor and a Bcl-2 inhibitor. Also provided is a kit comprising a telomerase inhibitor and a Bcl-2 inhibitor, for use in treating a hematological cancer. Such therapy in some cases comprises administering the Bcl-2 inhibitor to a subject, either preceding, following, or concomitantly with administration of the telomerase inhibitor. In some cases, the telomerase inhibitor is imetelstat.

In a related aspect, the invention provides a kit containing a dose of a telomerase inhibitor in an amount effective to inhibit proliferation of cancer cells in a subject. The kit in some cases includes an insert with instructions for administration of the telomerase inhibitor. The insert may provide a user with one set of instructions for using the inhibitor in combination with a Bcl-2 inhibitor. In some instances, the Bcl-2 inhibitor is ABT-199.

In some instances, the set of instructions for the combination therapy may recommend (i) a lower dose of the telomerase inhibitor, when used in combination with the Bcl-2 inhibitor, (ii) a lower dose of the Bcl-2 inhibitor, when used in combination with the telomerase inhibitor, and/or (iii) a different dosing regimen for one or both inhibitors than would normally be recommended.

It will be clear that in the paragraphs above in some cases, the telomerase inhibitor is imetelstat; in some cases, the telomerase inhibitor is imetelstat sodium; in some cases, the Bcl-2 inhibitor is ABT-199.

J. Exemplary Embodiments

One exemplary embodiment of the invention is a method of treatment comprising administering a telomerase inhibitor and a Bcl-2 inhibitor in combination to a subject in need of treatment for hematological cancer. In certain embodiments, the telomerase inhibitor is imetelstat. In alternate embodiments, the Bcl-2 inhibitor ABT-199, ABT-263 or ABT-737. In yet another embodiment, the Bcl-2 inhibitor is ABT-199. In one embodiment, the telomerase inhibitor is imetelstat and the Bcl-2 inhibitor is ABT-199.

The hematological cancer may be AML, essential thrombocythemia, polycythemia vera, primary myelofibrosis, systemic mastocytosis, chronic myeloid leukemia, chronic neutrophilic leukemia, chronic eosinophilic leukemia, refractory anemia with ringed sideroblasts, refractory cytopenia with multilineage dysplasia, refractory anemia with excess blasts, type 1, refractory anemia with excess blasts, type 2, myelodysplastic syndrome (MDS) with isolated del (5q), MDS unclassifiable, chronic myelomonocytic leukemia (CML), atypical chronic myeloid leukemia, juvenile myelomonocytic leukemia, myeloproliferative/myelodysplastic syndromes—unclassifiable, B lymphoblastic leukemia/lymphoma, T lymphoblastic leukemia/lymphoma, diffuse large B-cell lymphoma, primary central nervous system lymphoma, primary mediastinal B-cell lymphoma, Burkitt lymphoma/leukemia, follicular lymphoma, chronic lymphocytic leukemia (CLL)/small lymphocytic lymphoma, B-cell prolymphocytic leukemia, lymphoplasmacytic lymphoma/Waldenstrim macroglobulinemia, Mantle cell lymphoma, marginal zone lymphomas, post-transplant lymphoproliferative disorders, HIV-associated lymphomas, primary effusion lymphoma, intravascular large B-cell lymphoma, primary cutaneous B-cell lymphoma, hairy cell leukemia, monoclonal gammopathy of unknown significance, smoldering multiple myeloma, and solitary plasmacytomas (solitary bone and extramedullary). In one embodiment, the hematological cancer is AML.

In certain embodiments, the telomerase inhibitor imetelstat is administered for 1, 2, 3, 4, 5, 6, 7, 8 or more than 8 dosage cycles, each cycle comprising: a) intravenous administration of about 7-10 mg/kg imetelstat thereof once every four weeks, b) intravenous administration of about 7-10 mg/kg imetelstat once weekly for four weeks, c) intravenous administration of about 2.5-7 mg/kg imetelstat once every three weeks, or d) intravenous administration of about 0.5-9.4 mg/kg imetelstat once every four weeks. The imetelstat may be imetelstat sodium.

In certain embodiment, ABT-199 is administered at a dose of: a) about 50-400 mg ABT-199 daily; b) about 2 mg ABT-199 on day 1 with daily escalation to a final dose of about 800 mg on day 6 and daily thereafter; or c) 25 mg ABT-199 on day 1 with daily escalation to a final dose of about 400 mg on day 5 and daily thereafter. The administration of ABT-199 may be one day before, one day after, or the same day as, the administration of the telomerase inhibitor.

Another embodiment of the invention is a method of inducing apoptosis in a hematologic cancer cell comprising contacting the cell with a therapeutically effective amount of a telomerase inhibitor and contacting the cell with a therapeutically effective amount of a Bcl-2 inhibitor. The method may be carried out in vitro or in vivo. In one embodiment, the telomerase inhibitor is imetelstat. In another embodiment, the imetelstat is imetelstat sodium. In this method, the Bcl-2 inhibitor is ABT-199. In certain embodiments, hematological cancer cell is may be a cell from the following types of cancer: acute myeloid leukemia (AML); essential thrombocythemia; polycythemia vera; primary myelofibrosis; systemic mastocytosis; chronic myeloid leukemia; chronic neutrophilic leukemia; chronic eosinophilic leukemia; refractory anemia with ringed sideroblasts; refractory cytopenia with multilineage dysplasia; refractory anemia with excess blasts; type 1; refractory anemia with excess blasts; type 2; myelodysplastic syndrome (MDS) with isolated del (5q); MDS unclassifiable; chronic myelomonocytic leukemia (CML); atypical chronic myeloid leukemia; juvenile myelomonocytic leukemia; myeloproliferative/myelodysplastic syndromes—unclassifiable; B lymphoblastic leukemia/lymphoma; T lymphoblastic leukemia/lymphoma; diffuse large B-cell lymphoma; primary central nervous system lymphoma; primary mediastinal B-cell lymphoma; Burkitt lymphoma/leukemia; follicular lymphoma; chronic lymphocytic leukemia (CLL)/small lymphocytic lymphoma; B-cell prolymphocytic leukemia; lymphoplasmacytic lymphoma/Waldenstrim macroglobulinemia; Mantle cell lymphoma; marginal zone lymphomas; post-transplant lymphoproliferative disorders; HIV-associated lymphomas; primary effusion lymphoma; intravascular large B-cell lymphoma; primary cutaneous B-cell lymphoma; hairy cell leukemia; monoclonal gammopathy of unknown significance; smoldering multiple myeloma; and solitary plasmacytomas (solitary bone and extramedullary). In one embodiment, the hematological cancer cell is an acute myeloid leukemia (AML) cell.

The invention also provides for kits for combination therapy. Accordingly, one embodiment of the invention is a kit containing: (a) a dose of a telomerase inhibitor, in an amount effective, when administered, to induce apoptosis in a hematologic cancer cell; and (b) a dose of a Bcl-2 inhibitor, in an amount effective, when administered, to induce apoptosis in a hematologic cancer cell. In one embodiment of this kit, the telomerase inhibitor is imetelstat, and the Bcl-2 inhibitor is ABT-199.

One embodiment of the invention is a pharmaceutical composition comprising a telomerase inhibitor (e.g. imetelstat/imetelstat sodium) and a BCL-2 inhibitor (e.g. ABT-199) for use in treating hematological cancer. In one embodiment, the pharmaceutical composition comprises imetelstat/imetelstat sodium and ABT-199.

Another embodiment of the invention is a telomerase inhibitor for use in a method of treating hematological cancer, the method comprising administering the telomerase inhibitor and a Bcl-2 inhibitor in combination to a subject in need thereof. Yet another embodiment of the invention is a Bcl-2 inhibitor for use in a method of treating hematological cancer, the method comprising administering the Bcl-2 inhibitor and a telomerase inhibitor in combination to a subject in need thereof. An alternate embodiment of the invention is a combination comprising a telomerase inhibitor and a Bcl-2 inhibitor for use in a method of treating hematological cancer, the method comprising administering the combination to a subject in need thereof. In these embodiments, the combination of telomerase inhibitor and Bcl-2 inhibitor induces apoptosis of hematologic cancer cells. In these embodiments, the telomerase inhibitor may be imetelstat. In one embodiment, the imetelstat is imetelstat sodium. Also in these embodiments, the Bcl-2 inhibitor may be ABT-199. The imetelstat may be for administration for 1, 2, 3, 4, 5, 6, 7, 8 or more than 8 dosage cycles, each cycle comprising: a) intravenous administration of about 7-10 mg/kg imetelstat once every four weeks, b) intravenous administration of about 7-10 mg/kg imetelstat once weekly for about four weeks, or c) intravenous administration of about 2.5-7 mg/kg imetelstat once every three weeks, or d) intravenous administration of about 0.5-9.4 mg/kg imetelstat once every four weeks. The ABT-199 may be for administration at a dose of: about a) 50-400 mg ABT-199 daily; b) about 2 mg ABT-199 on day 1 with daily escalation to a final dose of about 800 mg on day 6 and daily thereafter; or c) about 25 mg ABT-199 on day 1 with daily escalation to a final dose of 400 mg on day 5 and daily thereafter. In certain embodiments, the administration of ABT-199 is one day before, one day after, or the same day as, the administration of the telomerase inhibitor.

In embodiments of the telomerase inhibitor, Bcl-2 inhibitor or combination, the hematological cancer may be acute myeloid leukemia (AML), essential thrombocythemia, polycythemia vera, primary myelofibrosis, systemic mastocytosis, chronic myeloid leukemia, chronic neutrophilic leukemia, chronic eosinophilic leukemia, refractory anemia with ringed sideroblasts, refractory cytopenia with multilineage dysplasia, refractory anemia with excess blasts, type 1, refractory anemia with excess blasts, type 2, myelodysplastic syndrome (MDS) with isolated del (5q), MDS unclassifiable, chronic myelomonocytic leukemia (CML), atypical chronic myeloid leukemia, juvenile myelomonocytic leukemia, myeloproliferative/myelodysplastic syndromes—unclassifiable, B lymphoblastic leukemia/lymphoma, T lymphoblastic leukemia/lymphoma, diffuse large B-cell lymphoma, primary central nervous system lymphoma, primary mediastinal B-cell lymphoma, Burkitt lymphoma/leukemia, follicular lymphoma, chronic lymphocytic leukemia (CLL)/small lymphocytic lymphoma, B-cell prolymphocytic leukemia, lymphoplasmacytic lymphoma/Waldenstrim macroglobulinemia, Mantle cell lymphoma, marginal zone lymphomas, post-transplant lymphoproliferative disorders, HIV-associated lymphomas, primary effusion lymphoma, intravascular large B-cell lymphoma, primary cutaneous B-cell lymphoma, hairy cell leukemia, monoclonal gammopathy of unknown significance, smoldering multiple myeloma, and solitary plasmacytomas (solitary bone and extramedullary). In one embodiment, the hematological cancer is acute myeloid leukemia (AML).

An alternate embodiment of the invention is an in vitro method of inducing apoptosis in a hematologic cancer cell comprising: contacting the cell with a therapeutically effective amount of a telomerase inhibitor; and contacting the cell with a therapeutically effective amount of a Bcl-2 inhibitor. In one embodiment, the telomerase inhibitor is imetelstat. The imetelstat may be imetelstat sodium. The Bcl-2 inhibitor may be ABT-199.

In certain embodiments of the in vitro method, the hematological cancer cell is a cell from the following types of cancer: acute myeloid leukemia (AML); essential thrombocythemia; polycythemia vera; primary myelofibrosis; systemic mastocytosis; chronic myeloid leukemia; chronic neutrophilic leukemia; chronic eosinophilic leukemia; refractory anemia with ringed sideroblasts; refractory cytopenia with multilineage dysplasia; refractory anemia with excess blasts; type 1; refractory anemia with excess blasts; type 2; myelodysplastic syndrome (MDS) with isolated del (5q); MDS unclassifiable; chronic myelomonocytic leukemia (CML); atypical chronic myeloid leukemia; juvenile myelomonocytic leukemia; myeloproliferative/myelodysplastic syndromes—unclassifiable; B lymphoblastic leukemia/lymphoma; T lymphoblastic leukemia/lymphoma; diffuse large B-cell lymphoma; primary central nervous system lymphoma; primary mediastinal B-cell lymphoma; Burkitt lymphoma/leukemia; follicular lymphoma; chronic lymphocytic leukemia (CLL)/small lymphocytic lymphoma; B-cell prolymphocytic leukemia; lymphoplasmacytic lymphoma/Waldenstrim macroglobulinemia; Mantle cell lymphoma; marginal zone lymphomas; post-transplant lymphoproliferative disorders; HIV-associated lymphomas; primary effusion lymphoma; intravascular large B-cell lymphoma; primary cutaneous B-cell lymphoma; hairy cell leukemia; monoclonal gammopathy of unknown significance; smoldering multiple myeloma; and solitary plasmacytomas (solitary bone and extramedullary). In one embodiment of the in vitro method, the hematological cancer cell is an acute myeloid leukemia (AML) cell.

Yet another embodiment of the invention is a combination comprising a telomerase inhibitor and a Bcl-2 inhibitor. In one embodiment, the telomerase inhibitor is imetelstat and the Bcl-2 inhibitor is ABT-199. In another embodiment, the telomerase inhibitor is imetelstat sodium and the Bcl-2 inhibitor is ABT-199. The combination may be for use as a medicament.

Another embodiment of the invention is use of imetelstat or imetelstat sodium for treating a hematological cancer in a patient undergoing BCL inhibition therapy. An alternate embodiment is use of ABT-199 for treating a hematological cancer in a patient undergoing telomerase inhibition therapy. Yet another embodiment of the invention is imetelstat sodium for use in a method of treating acute myeloid leukemia (AML), the method comprising administering imetelstat sodium and ABT-199 in combination to a subject in need thereof. An additional embodiment is ABT-199 for use in a method of treating acute myeloid leukemia (AML), the method comprising administering ABT-199 and imetelstat sodium in combination to a subject in need thereof. A further embodiment is a combination comprising imetelstat sodium and ABT-199 for use in a method of treating acute myeloid leukemia (AML), the method comprising administering the combination to a subject in need thereof. As applicable, in these embodiments, the imetelstat sodium may be for administration for 1, 2, 3, 4, 5, 6, 7, 8 or more than 8 dosage cycles, each cycle comprising: a) intravenous administration of about 7-10 mg/kg imetelstat sodium once every four weeks, b) intravenous administration of about 7-10 mg/kg imetelstat sodium once weekly for four weeks, or c) intravenous administration of about 2.5-7 mg/kg imetelstat sodium once every three weeks, or d) intravenous administration of about 0.5-9.4 mg/kg imetelstat sodium once every four weeks. Furthermore, in these embodiments, the ABT-199 maybe for administration at a dose of: a) about 50-400 mg ABT-199 daily; b) about 2 mg ABT-199 on day 1 with daily escalation to a final dose of 800 mg on day 6 and daily thereafter; or c) about 25 mg ABT-199 on day 1 with daily escalation to a final dose of 400 mg on day 5 and daily thereafter. In certain of these embodiments, the administration of ABT-199 is one day before, one day after, or the same day as, the administration of imetelstat sodium.

Yet another embodiment of the invention is an in vitro method of inducing apoptosis in an acute myeloid leukemia (AML) cell comprising: contacting the cell with a therapeutically effective amount of imetelstat sodium; and contacting the cell with a therapeutically effective amount of ABT-199.

In all of the above embodiments, the telomerase inhibitor may be imetelstat and the Bcl-2 inhibitor may be ABT-199. More in particular, in all of the above embodiments, the telomerase inhibitor may be imetelstat sodium and the Bcl-2 inhibitor may be ABT-199.

The present invention is further illustrated, but not limited by, the following examples.

EXAMPLES

Example 1: Telomerase Inhibitor Imetelstat Sodium in Combination with the BCL-2 Inhibitor Venetoclax Enhances Apoptosis in AML Cell Lines In Vitro AML tumor cells KG-1 (ATCC #CCL-246) and MOLM-13 (DSMZ #ACC554) were plated at a density of ~20,000 cells per well on 96-well polystyrene U-bottom tissue culture plates (Corning catalog #353777) in RPMI-1640 (ThermoFisher catalog #11875-085) supplemented with 10% fetal bovine serum (ThermoFisher catalog #16140-089) and 1% penicillin/streptomycin antibiotic cocktail (ThermoFisher catalog 15140-122) and grown in a 37° C. incubator under humidified 5% $CO_2$ atmosphere. Cells were treated immediately with imetelstat sodium (Janssen Biotech, Inc.) prepared in RPMI-1640 supplemented with 10% fetal bovine serum and/or ABT-199 (Selleckchem catalog #S8048) prepared as a 1000× stock in DMSO, diluted 1:100 in phosphate buffered saline (PBS, vehicle; ThermoFisher catalog #20012-027). In 96 hour experiments, a second dose of compound(s) was applied at 48 hours without the addition of fresh media as both ABT-199 and imetelstat sodium have in-vitro half-lives less than 48 hours (Shammas et al., *Leukemia*, 22(7):1410-1418 (2008)). Imetelstat sodium was tested from 0-50 µM and ABT-199 was tested from 0-500 nM. Control Non-complimentary and Mismatch oligonucleotides (U.S. Pat. No. 7,998,938) shown in Table 2 were used at identical concentrations to imetelstat sodium to show that effects are specific to the combination of imetelstat sodium and ABT-199.

TABLE 2 hTR Targeting Sequence

| | | |
|---|---|---|
| Imetelstat sodium[a] | 5'-R-TAGGGTTAGACAA-NH2-3' | SEQ ID NO: 1 |
| Mismatch oligo[b] | 5'-R-TAGGTGTAAGCAA-NH2-3' | SEQ ID NO: 2 |
| Non-complimentary oligo[c] | 5'-AACAGATTGGGAT-R-3' | SEQ ID NO: 3 |

R represents:
[a]Palmitoyl [(CH$_2$)$_{14}$CH$_3$] amide is conjugated through an aminoglycerol linker to the 5'thiophosphate group of an N3' → P5' thiophosphoroamidate (NPS)-linked oligonucleotide.
[b]Palmitoyl [(CH$_2$)$_{14}$CH$_3$] amide is conjugated through an aminoglyercol linker to the 5'thiophosphate group of an N3' → P5' thiophosphoroamidate (NPS)-linked oligonucleotide.
[c]Palmitoyl [(CH$_2$)$_{14}$CH$_3$] amide is conjugated through the terminal 3' amino group of an NPS oligonucleotide.

At 48 and 96 hours, cells were measured for healthy, early apoptotic and apoptotic populations with an Annexin V (interior cell membrane stain) plus Propidium Iodide (PI, DNA binding dye) flow cytometry assay kit (BioLegend catalog 640914). Annexin V detects the externalization of phosphatidylserine in apoptotic cells using recombinant annexin V conjugated to green-fluorescent FITC dye and dead cells using Propidium iodide (PI). Propidium iodide stains necrotic cells with red fluorescence. After treatment with both probes, early apoptotic cells show green fluorescence, apoptotic (dead) cells show red and green fluorescence, and live cells show little or no fluorescence. Briefly, cells were pelleted and washed 2× with PBS before suspension in Annexin V binding buffer containing a 1:2 ratio of anti-Annexin V-FITC and Propidium Iodide, according to the manufacturer's suggested protocol. Cells were stained for 30 minutes at 4° C. in the dark, followed by 3× washes with PBS and suspension in FACs Stain Buffer (BD catalog 554657) prior to interrogation on a BD FACs Canto flow cytometer for forward scatter, side scatter, FITC, and PE channels. Cell populations were analyzed using Cytobank software and compared to untreated (no imetelstat sodium or ABT-199) conditions to establish the boundaries for viable cell (unstained in either channel; i.e. double-negative population) gating. For all experiments, dot plots of flow cytometry data show four quadrants with the percent of live cells in the lower left quadrant, percent of early apoptotic cells (Annexin V+/PI−) in the upper left quadrant, and percent of apoptotic (dead) cells (double labeled Annexin V+/PI+) in the top right quadrant. The percentage of apoptotic cells (double labeled) was used to calculate combination effects using both the Highest Single Agent (HSA) and Bliss additivity models (J Tang et al. *Frontiers in Pharmacology*. 2015; 6 (181)).

Using the HSA model, the cytotoxic effect of the combined condition ("C") was compared to the effect generated by each of the single agent controls ("A" or "B") for the respective dose in the combination:

Excess over HSA=$C-A$ (if $A>B$) or $C-B$ (if $A<B$)

The Bliss model performs a similar comparison, but instead of the highest effect of single agent, the Bliss model subtracts from the combination a value equal to the sum of each single agent minus their product:

Excess over Bliss=$C-[(A+B)-(A*B)]$

These models are able to demonstrate additivity or weak synergy in a combination.

Results of AML Cell Line Treatment

Dot plots of flow cytometry data for KG-1 cells after 48 hour treatment with imetelstat sodium and/or ABT-199 are shown in FIG. 1A with a graph of % apoptotic cells (double label) vs. ABT-199 concentration at various imetelstat sodium concentrations shown in FIG. 1B. KG-1 exhibits minor sensitivity to ABT-199 after 48 hours (~9% and ~14% at 100 nM and 500 nM respectively) and minimal sensitivity to imetelstat sodium. However, when treatment of 50 µM imetelstat sodium is combined with 100 nM or 500 nM ABT-199, a greater effect on cell death is observed at (~27% at 100 nM and ~50% at 500 nM). Tables 3 and 4 show the calculations of a combination effect using the HSA or BLISS models for treatment of KG-1 cells at 48 hours. Negative values do not indicate antagonism in these models, only lack of interaction.

TABLE 3

Excess over Highest Single Agent in KG-1 cells at 48 hours with ABT-199 and imetelstat sodium

| | | ABT-199, nM | | | | | |
|---|---|---|---|---|---|---|---|
| Excess over HSA | | 0 | 1 | 5 | 20 | 100 | 500 |
| Imetelstat sodium, µM | 50 | 0 | 0 | 2 | 9 | 18 | 36 |
| | 25 | 0 | 2 | 3 | 5 | 7 | 9 |
| | 10 | 0 | 1 | 2 | 2 | 4 | 2 |
| | 0 | 0 | 0 | 0 | 0 | 0 | 0 |

TABLE 4

Excess over BLISS in KG-1 cells at 48 hours with ABT-199 and imetelstat sodium

| | | | ABT-199, nM | | | | |
|---|---|---|---|---|---|---|---|
| Excess over BLISS | | 0 | 1 | 5 | 20 | 100 | 500 |
| Imetelstat sodium, μM | 50 | 0 | −5 | −2 | 3 | 11 | 28 |
| | 25 | 0 | −4 | −2 | −1 | 0 | 2 |
| | 10 | 0 | −5 | −3 | −4 | −2 | −3 |
| | 0 | 0 | 0 | 0 | 0 | 0 | 0 |

Figure 2A:
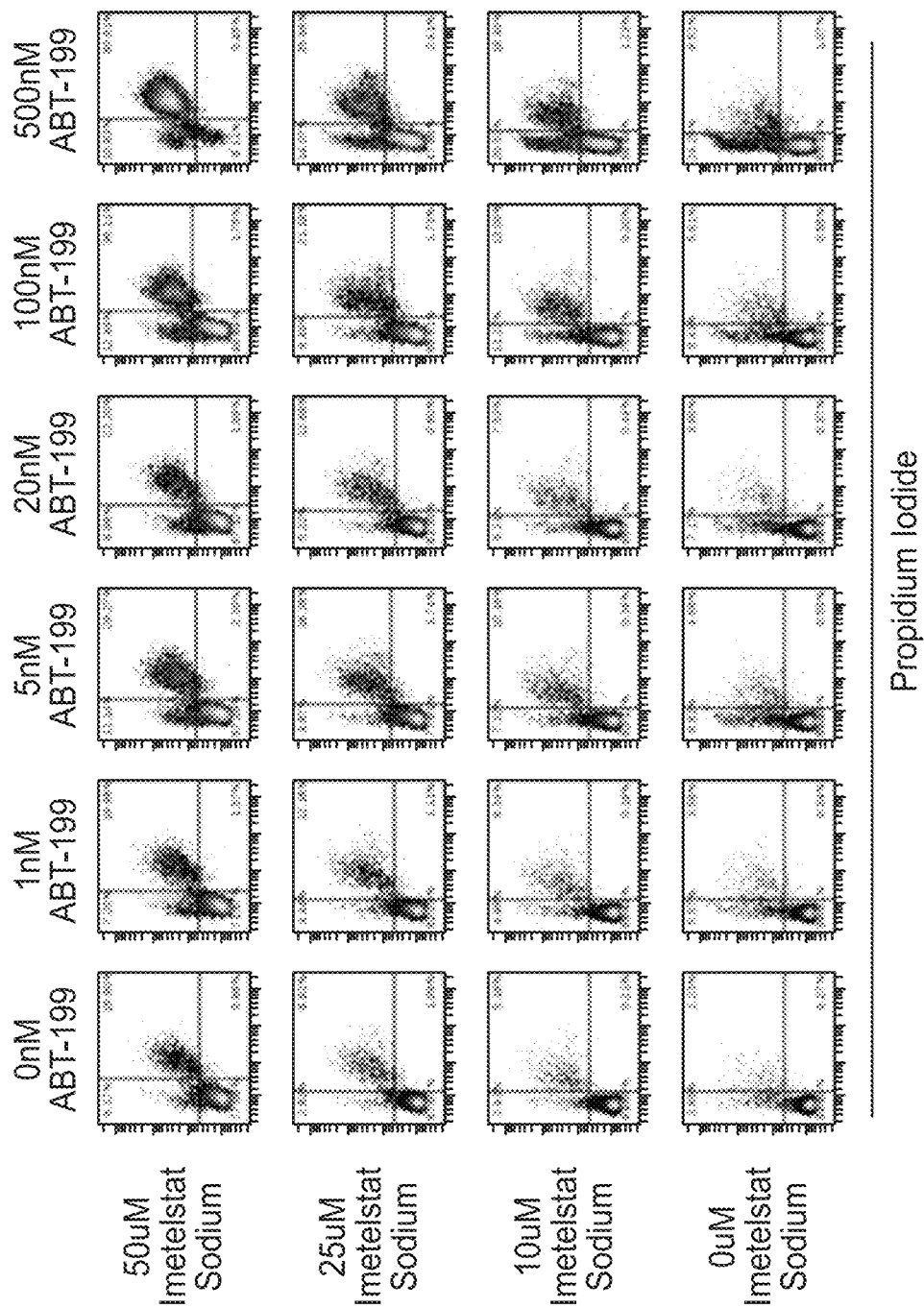

Dot plots of flow cytometry data for KG-1 cells after 96 hour treatment with imetelstat sodium and/or ABT-199 are shown in FIG. 2A with a graph of % apoptotic cells (double label) vs. ABT-199 concentration at various imetelstat sodium concentrations shown in FIG. 2B. KG-1 exhibits minor sensitivity to ABT-199 after 96 hours (~6% and ~10% at 100 nM and 500 nM respectively) and some sensitivity to imetelstat sodium is also observed (5%, 9% and 16% at 10 μM, 20 μM and 50 μM respectively). However, when treatment of 25 or 50 M imetelstat sodium is combined with 20 to 500 nM ABT-199, greater effects on cell death are observed at all concentrations. Tables 5 and 6 show the calculations of a combination effect using the HSA or BLISS models on treatment of KG-1 cells at 96 hours.

TABLE 5

Excess over Highest Single Agent in KG-1 cells at 96 hours with ABT-199 and imetelstat sodium

| | | | ABT-199, nM | | | | |
|---|---|---|---|---|---|---|---|
| Excess over HSA | | 0 | 1 | 5 | 20 | 100 | 500 |
| Imetelstat sodium, μM | 50 | 0 | 4 | 6 | 13 | 20 | 65 |
| | 25 | 0 | 3 | 4 | 7 | 12 | 26 |
| | 10 | 0 | 1 | 2 | 5 | 7 | 10 |
| | 0 | 0 | 0 | 0 | 0 | 0 | 0 |

TABLE 6

Excess over BLISS in KG-1 cells at 48 hours with ABT-199 and imetelstat sodium

| | | | ABT-199, nM | | | | |
|---|---|---|---|---|---|---|---|
| Excess over BLISS | | 0 | 5 | 1 | 20 | 100 | 500 |
| Imetelstat, sodium μM | 50 | 0 | 1 | 3 | 10 | 16 | 57 |
| | 25 | 0 | 0 | 0 | 3 | 7 | 18 |
| | 10 | 0 | −2 | −1 | 1 | 2 | 5 |
| | 0 | 0 | 0 | 0 | 0 | 0 | 0 |

Figure 3B:
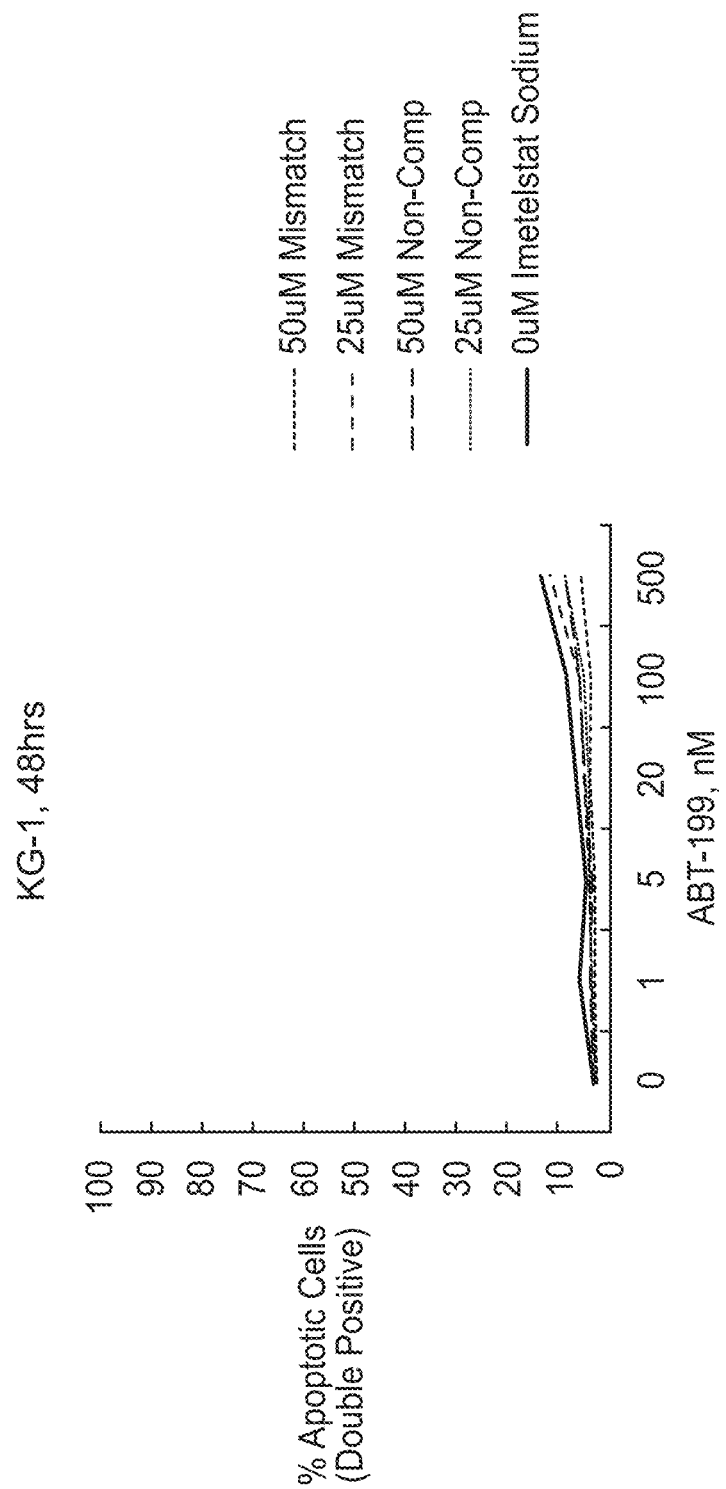
Figure 4A:
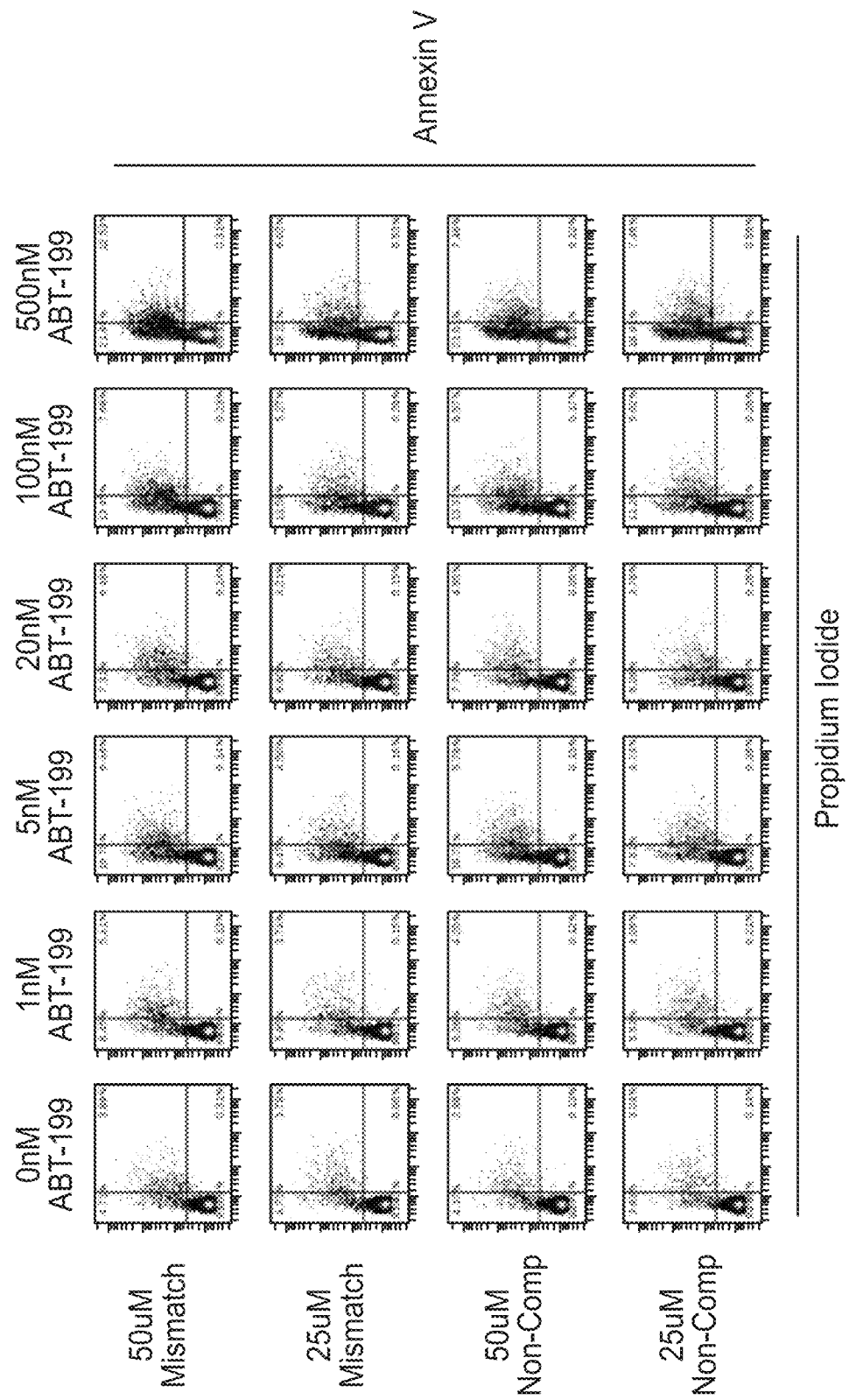
FIGS. 4A and 4B show the effects of treating KG-1 cells with mismatch or non-complimentary oligonucleotides and ABT-199 for 96 hours.
Figure 4B:
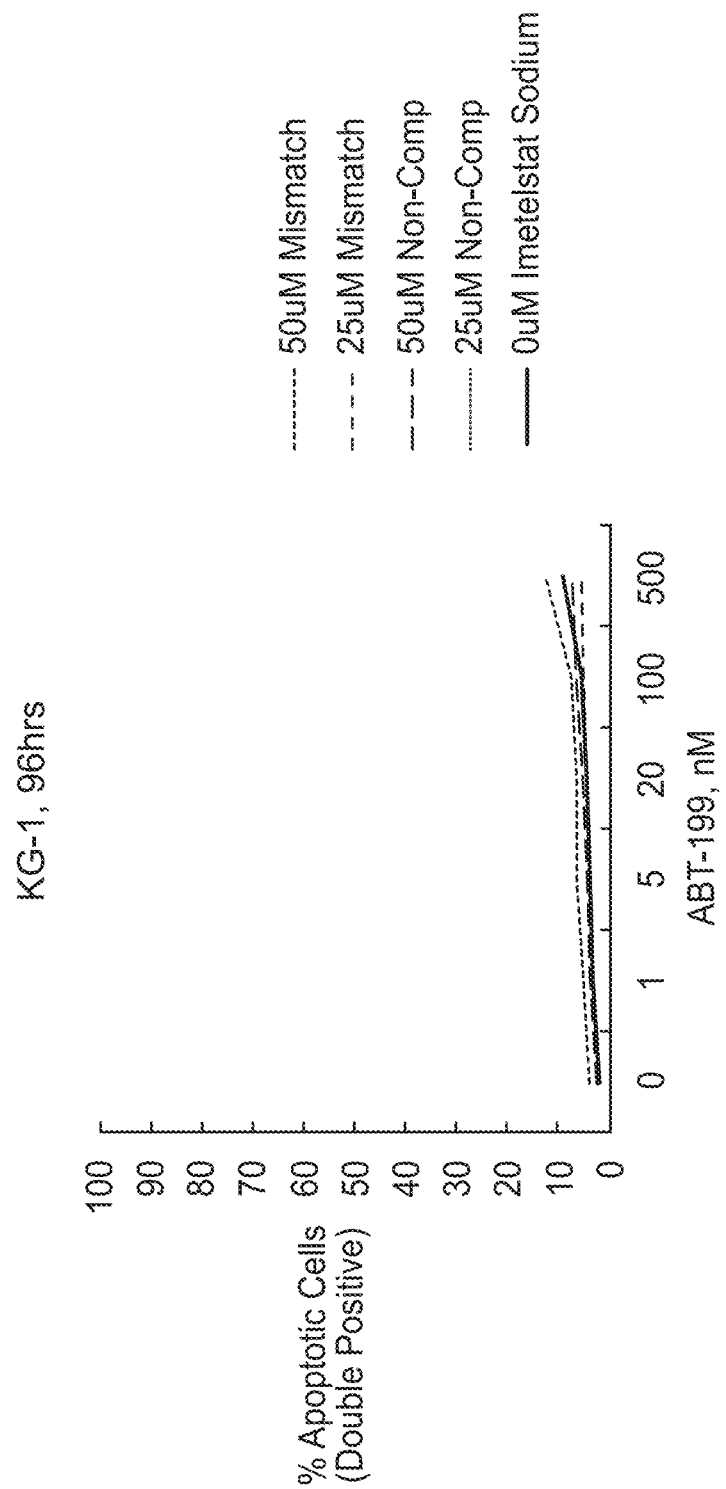

Dot plots of flow cytometry data for KG-1 cells are shown after treatment at 48 hour (FIG. 3A) or 96 hour (FIG. 4A) with mismatch or non-complimentary oligonucleotides and ABT-199. Graphs of % apoptotic cells (double label) vs. ABT-199 concentration at various oligonucleotide concentrations are shown for 48 hour (FIG. 3B) or 96 hours (FIG. 4B). Excess over highest single-agent (Tables 7 and 8) and excess over Bliss (Tables 9 and 10) models confirm no effect with oligonucleotide controls. Negative values do not indicate antagonism in these models, only lack of interaction.

TABLE 7

Excess over HSA in KG-1 cells at 48 hours with non-complimentary or mismatch controls

| | | | ABT-199, nM | | | | |
|---|---|---|---|---|---|---|---|
| Excess over HSA | | 0 | 1 | 5 | 20 | 100 | 500 |
| Mismatch μM | 50 | 0 | −3 | −2 | −3 | −5 | −8 |
| | 25 | 0 | −3 | −2 | −2 | −3 | −5 |
| Non-complimentary, μM | 50 | 0 | −2 | 1 | −1 | −3 | −5 |
| | 25 | 0 | −2 | −1 | −2 | −3 | −3 |

TABLE 8

Excess over HSA in KG-1 cells at 96 hours with non-complimentary or mismatch controls

| | | | ABT-199, nM | | | | |
|---|---|---|---|---|---|---|---|
| Excess over HSA | | 0 | 1 | 5 | 20 | 100 | 500 |
| Mismatch μM | 50 | 0 | 2 | 3 | 2 | 2 | 3 |
| | 25 | 0 | 0 | 0 | 0 | 0 | −3 |
| Non-complimentary, μM | 50 | 0 | 1 | 1 | 1 | 1 | −2 |
| | 25 | 0 | 0 | 0 | 0 | −1 | −2 |

TABLE 9

Excess over BLISS in KG-1 cells at 48 hours with non-complimentary or mismatch controls

| | | | ABT-199, nM | | | | |
|---|---|---|---|---|---|---|---|
| Excess over Bliss | | 0 | 1 | 5 | 20 | 100 | 500 |
| Mismatch, μM | 50 | 0 | −5 | −5 | −6 | −8 | −11 |
| | 25 | 0 | −5 | −4 | −4 | −5 | −7 |
| Non-complimentary, μM | 50 | 0 | −5 | −2 | −4 | −6 | −8 |
| | 25 | 0 | −5 | −4 | −5 | −5 | −5 |

TABLE 10

Excess over BLISS in KG-1 cells at 96 hours with non-complimentary or mismatch controls

| | | | ABT-199, nM | | | | |
|---|---|---|---|---|---|---|---|
| Excess over Bliss | | 0 | 1 | 5 | 20 | 100 | 500 |
| Mismatch, μM | 50 | 0 | −2 | −1 | −2 | −2 | −1 |
| | 25 | 0 | −4 | −3 | −4 | −4 | −7 |
| Non-complimentary, μM | 50 | 0 | −2 | −2 | −2 | −2 | −5 |
| | 25 | 0 | −2 | −3 | −3 | −3 | −5 |

Figure 5A:
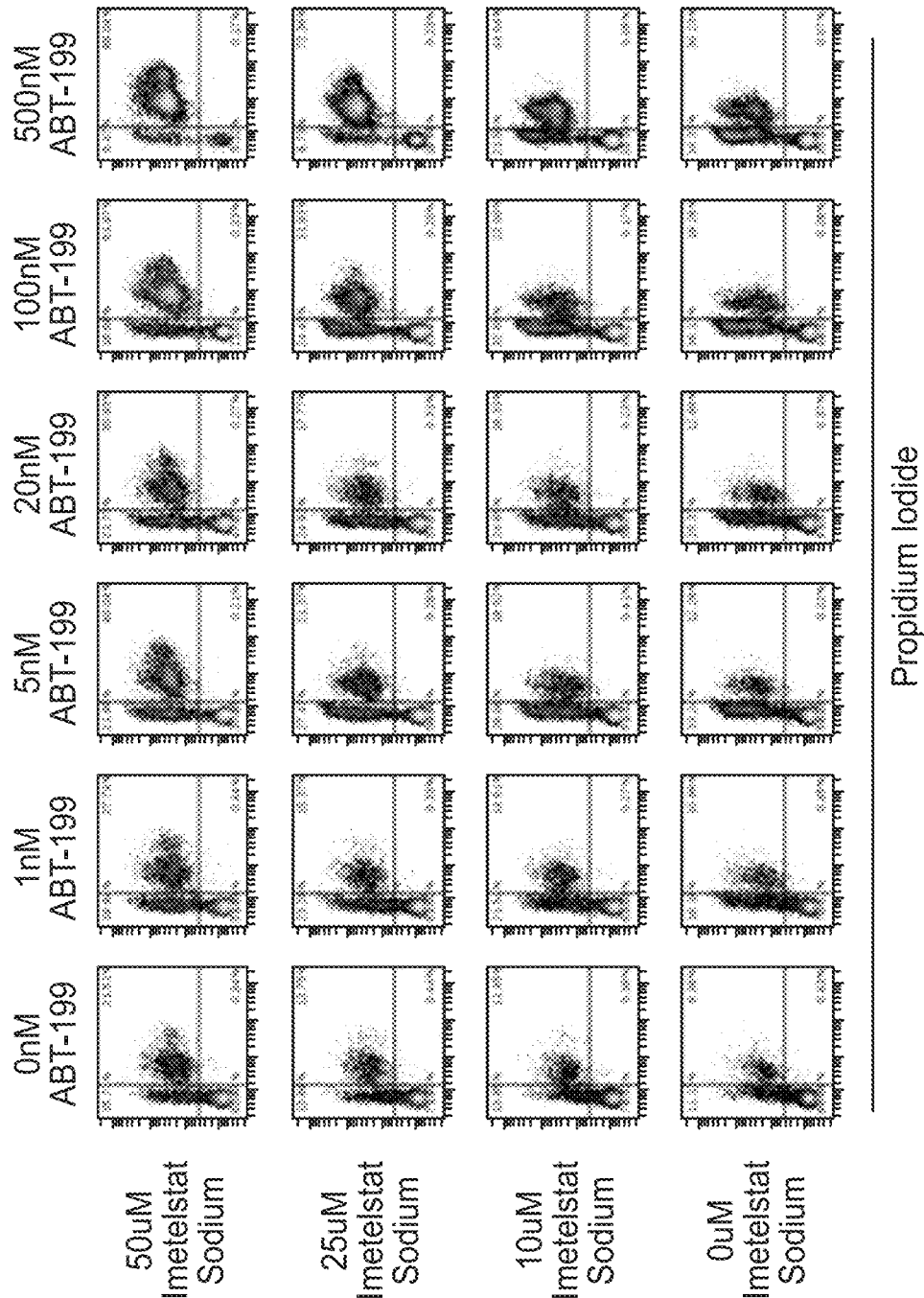
FIGS. 5A and 5B show the effects of treating MOLM-13 cells with imetelstat sodium and/or ABT-199 for 48 hours.
Figure 5B:
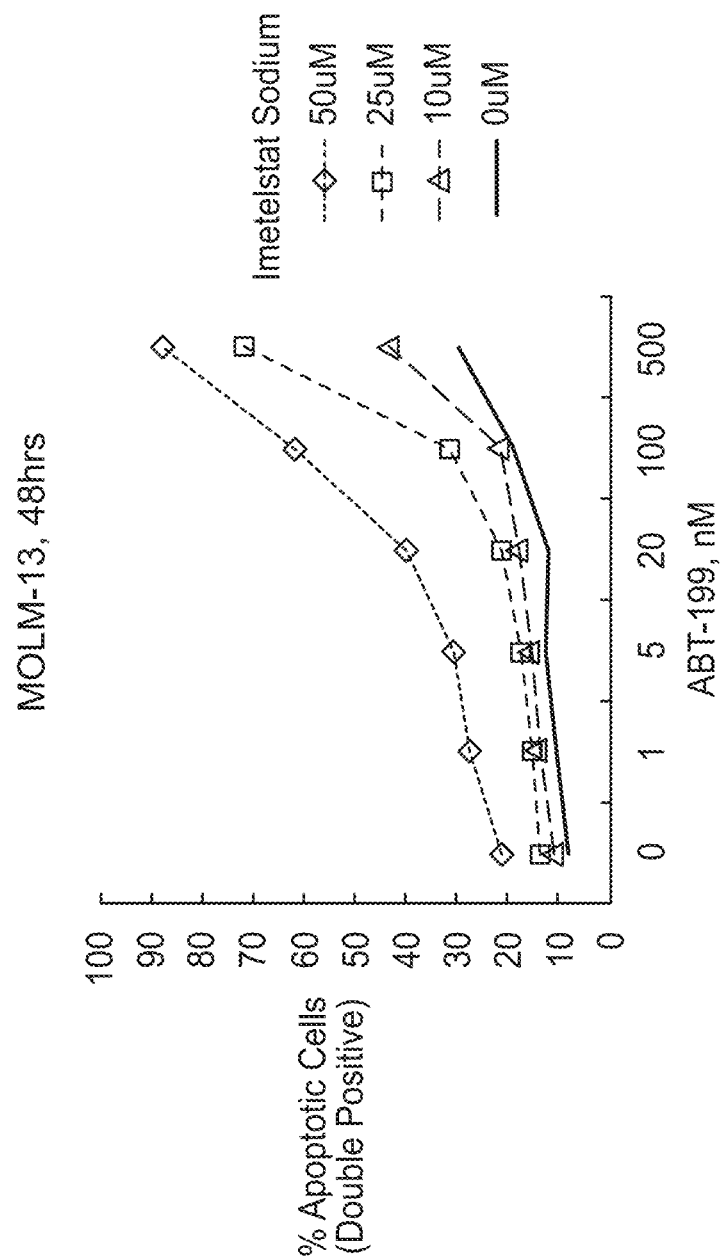

Dot plots of flow cytometry data for MOLM-13 cells after 48 hour treatment with imetelstat sodium and/or ABT-199 are shown in FIG. 5A with a graph of % apoptotic cells (double label) vs. ABT-199 concentration at various imetelstat sodium concentrations shown in FIG. 5B. MOLM-13 exhibits some sensitivity to ABT-199 after 48 hours (~19% and ~30% at 100 nM and 500 nM respectively) and some sensitivity to imetelstat sodium (21.5% at 50 μM). However, when the 25 μM imetelstat sodium was combined with ABT-199, a greater effect on cell death was observed (~32% and ~72% at 100 nM and 500 nM respectively). The greatest effect on cell death was observed with 50 μM imetelstat sodium combined with ABT-199 at 100 nM (62%)

and 500 nM (88%). Surprisingly, in combination with imetelstat sodium at 50 µM, ABT-199 has observed effect on cell killing at lower concentrations of 5 nM and 20 nM. Tables 11 and 12 show the calculations of a combination effect using the HSA or BLISS models for treatment of MOLM-13 cells at 48 hours.

TABLE 11

Excess over Highest Single Agent in MOLM-13 cells at 48 hours with ABT-199 and imetelstat sodium

| | | ABT-199, nM | | | | |
|---|---|---|---|---|---|---|
| Excess over HSA | | 0 | 1 | 5 | 20 | 100 | 500 |
| Imetelstat | 50 | 0 | 6 | 9 | 19 | 40 | 58 |
| sodium, µM | 25 | 0 | 2 | 4 | 8 | 13 | 42 |
| | 10 | 0 | 3 | 3 | 6 | 3 | 14 |
| | 0 | 0 | 0 | 0 | 0 | 0 | 0 |

TABLE 12

Excess over BLISS in MOLM-13 cells at 48 hours with ABT-199 and imetelstat sodium

| | | ABT-199, nM | | | | |
|---|---|---|---|---|---|---|
| Excess over BLISS | | 0 | 1 | 5 | 20 | 100 | 500 |
| Imetelstat | 50 | 0 | −2 | −1 | 9 | 25 | 43 |
| sodium, µM | 25 | 0 | −8 | −7 | −3 | 2 | 33 |
| | 10 | 0 | −6 | −7 | −4 | −7 | 6 |
| | 0 | 0 | 0 | 0 | 0 | 0 | 0 |

Dot plots of flow cytometry data for MOLM-13 cells after 96 hour treatment with imetelstat sodium and/or ABT-199 are shown in FIG. 6A with a graph of % apoptotic cells (double label) vs. ABT-199 concentration at various imetelstat sodium concentrations shown in FIG. 6B. MOLM-13 exhibits sensitivity to ABT-199 after 96 hours (>30% cell death at 5, 20, 100 and 500 nM) and sensitivity to imetelstat sodium (≥30% at 10, 25 and 50 µM). At all concentrations of combined ABT-199 plus imetelstat sodium treatment, there is enhanced cell-killing. Greater that 90% cell death was observed at the lowest concentration of imetelstat sodium (10 µM) when combined with the highest concentration of ABT-199 (500 nM). Greater than 90% cell death was also observed at concentrations of ABT-199 100 nM and 500 nM when combined. At the highest concentration of imetelstat sodium (50 µM) nearly complete cell death was observed at ABT-199 concentrations of 5, 10, 20, 100 and 500 nM. Tables 13 and 14 show the calculations of a combination effect using the HSA or BLISS models for treatment of MOLM-13 cells at 96 hours.

TABLE 13

Excess over Highest Single Agent in MOLM-13 cells at 96 hours with ABT-199 and imetelstat sodium

| | | ABT-199, nM | | | | |
|---|---|---|---|---|---|---|
| Excess over HSA | | 0 | 1 | 5 | 20 | 100 | 500 |
| Imetelstat | 50 | 0 | 26 | 41 | 49 | 49 | 50 |
| sodium, µM | 25 | 0 | 14 | 26 | 33 | 46 | 58 |
| | 10 | 0 | 10 | 11 | 23 | 25 | 56 |
| | 0 | 0 | 0 | 0 | 0 | 0 | 0 |

TABLE 14

Excess over Highest Single Agent in MOLM-13 cells at 96 hours with ABT-199 and imetelstat sodium

| | | ABT-199, nM | | | | |
|---|---|---|---|---|---|---|
| Excess over BLISS | | 0 | 1 | 5 | 20 | 100 | 500 |
| Imetelstat | 50 | 0 | 13 | 23 | 26 | 27 | 32 |
| sodium, µM | 25 | 0 | −1 | 4 | 11 | 23 | 37 |
| | 10 | 0 | −8 | −7 | 7 | 9 | 37 |
| | 0 | 0 | 0 | 0 | 0 | 0 | 0 |

Figure 7A:
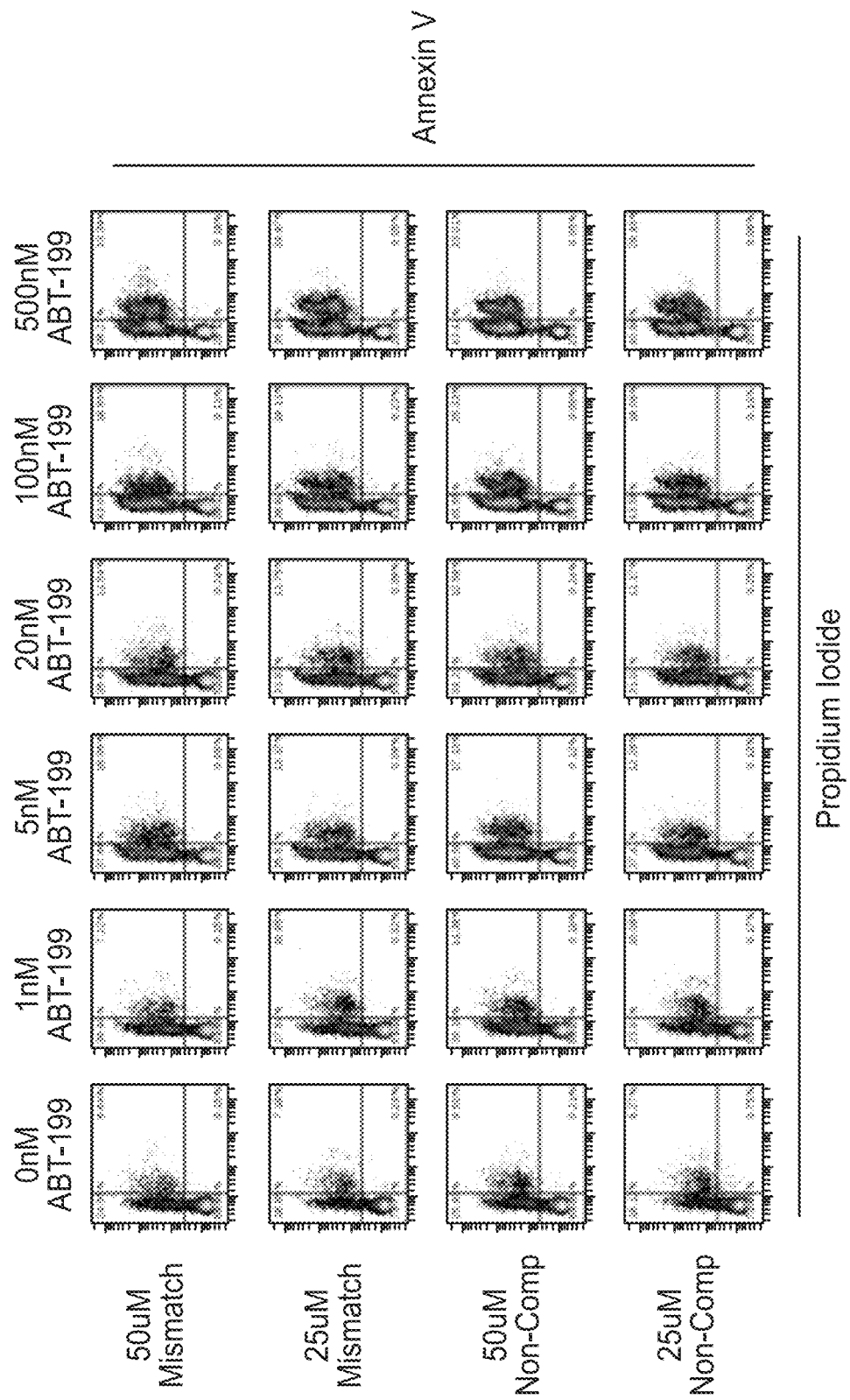
Figure 8A:
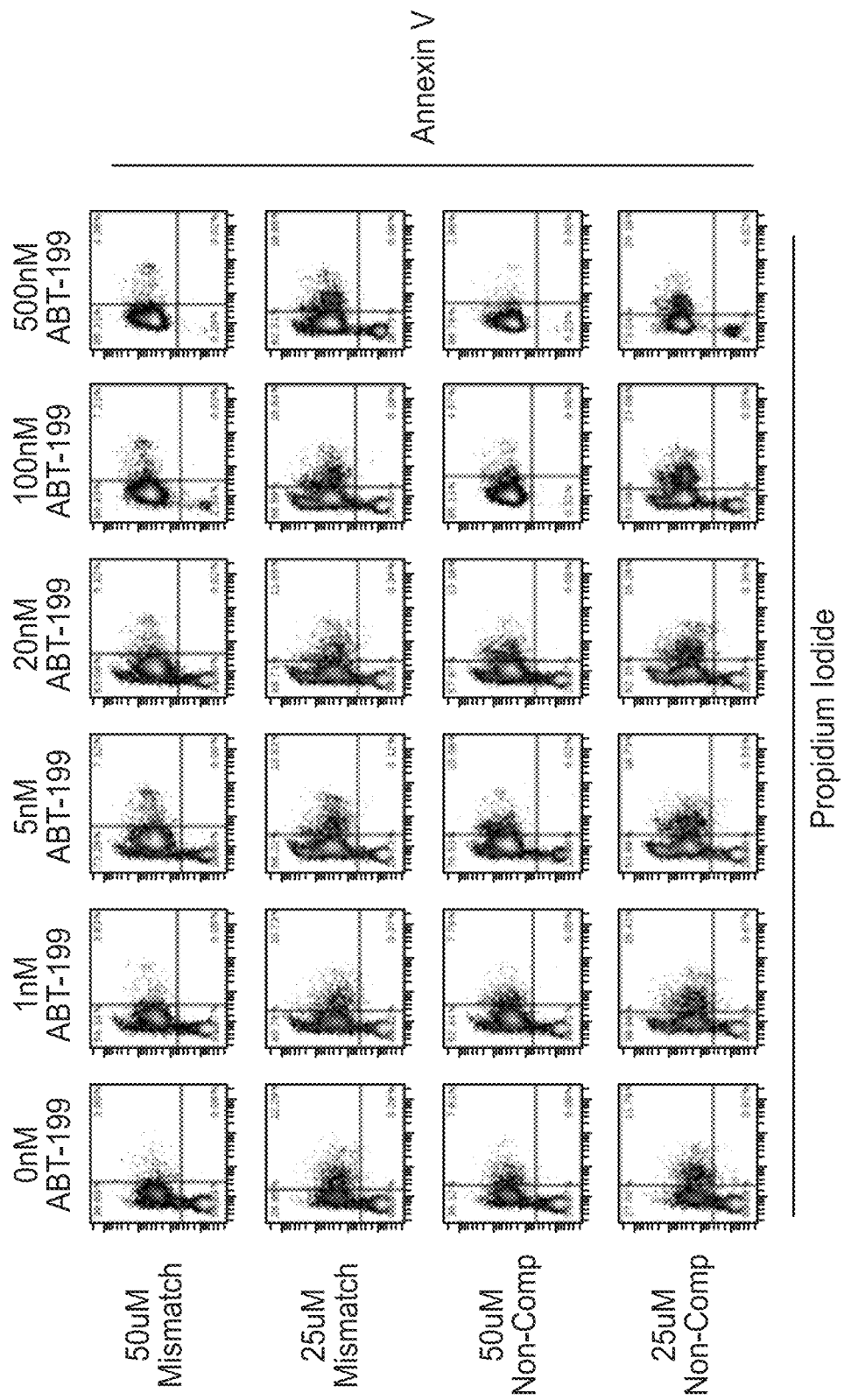

Dot plots of flow cytometry data for MOLM-13 cells are shown after treatment at 48 hour (FIG. 7A) or 96 hour (FIG. 8A) with mismatch or non-complimentary oligonucleotides and ABT-199. Graphs of % apoptotic cells (double label) vs. ABT-199 concentration at various oligonucleotide concentrations are shown for 48 hour (FIG. 7B) or 96 hours (FIG. 8B). Excess over highest single-agent (Tables 15 and 17) and excess over Bliss (Tables 16 and 18) models confirm no effect with oligonucleotide controls. Negative values do not indicate antagonism in these models, only lack of interaction.

TABLE 15

Excess over HSA in MOLM-13 cells at 48 hours with non-complimentary or mismatch controls

| | | ABT-199, nM | | | | |
|---|---|---|---|---|---|---|
| Excess over HSA | | 0 | 1 | 5 | 20 | 100 | 500 |
| Mismatch, µM | 50 | 0 | −4 | −1 | 4 | −1 | 3 |
| | 25 | 0 | 0 | −1 | 1 | 0 | 5 |
| Non-complimentary, µM | 50 | 0 | 1 | 0 | 5 | 6 | 3 |
| | 25 | 0 | −1 | −2 | 0 | −1 | −2 |

TABLE 16

Excess over BLISS in MOLM-13 cells at 48 hours with non-complimentary or mismatch controls

| | | ABT-199, nM | | | | |
|---|---|---|---|---|---|---|
| Excess over Bliss | | 0 | 1 | 5 | 20 | 100 | 500 |
| Mismatch, µM | 50 | 0 | −10 | −7 | −2 | −6 | −1 |
| | 25 | 0 | −6 | −7 | −5 | −6 | 0 |
| Non-complimentary, µM | 50 | 0 | −8 | −9 | −3 | −2 | −4 |
| | 25 | 0 | −8 | −9 | −7 | −8 | −8 |

TABLE 17

Excess over HSA in MOLM-13 cells at 96 hours with non-complimentary or mismatch controls

| | | ABT-199, nM | | | | |
|---|---|---|---|---|---|---|
| Excess over HSA | | 0 | 1 | 5 | 20 | 100 | 500 |
| Mismatch, µM | 50 | 0 | −22 | −32 | −39 | −37 | −32 |
| | 25 | 0 | −15 | −26 | −33 | −29 | −17 |
| Non-complimentary, µM | 50 | 0 | −18 | −24 | −31 | −40 | −33 |
| | 25 | 0 | −10 | −22 | −28 | −21 | −16 |

TABLE 18

Excess over BLISS in MOLM-13 cells at 96 hours with non-complimentary or mismatch controls

| Excess over Bliss | | ABT-199, nM | | | | | |
|---|---|---|---|---|---|---|---|
| | | 0 | 1 | 5 | 20 | 100 | 500 |
| Mismatch, µM | 50 | 0 | −25 | −34 | −41 | −40 | −35 |
| | 25 | 0 | −24 | −33 | −39 | −36 | −25 |
| Non-complimentary, µM | 50 | 0 | −24 | −29 | −35 | −44 | −38 |
| | 25 | 0 | −19 | −29 | −34 | −28 | −24 |

Example 2: Studies on the Mechanism of Interaction Between Imetelstat Sodium and ABT-199 in Treated Cells Mechanistically, imetelstat sodium functions primarily through inhibiting the active site of the telomerase enzyme complex. In so doing, the telomere ends on which the enzyme acts are therefore not elongated. With the rapid and repeated cell division of tumor cells, over time they become vulnerable to progressive telomere shortening. With the process of telomeric renewal blocked, cells progressively approach crisis and ultimately trigger apoptosis (Bruedigam et al., *Cell Stem Cell.*, 15: 775-790 (2014)).

Bcl-2 and its related family members play a role in delivering anti-apoptotic signals to tumor cells. Bcl-2 works by inhibiting Bax, which is a key mediator in signaling the release of apoptotic factors that bring about normal programmed cell death. Under these signals Bax translocates to the mitochondria, triggering cytochrome c and other apoptotic factors that lead to activation of the caspase cascade and culminate in cell death via the intrinsic (i.e., non-receptor mediated—TRAIL, TNFa, etc.) pathway. The presence of Bcl-2 yields interference in these signals as Bcl-2 can directly inhibit Bax. Without Bax, apoptotic factors are not released and cells are freed from the apoptotic signals.

These two pathways converge as the primary protein component of telomerase, hTERT, also plays auxiliary roles in the intrinsic apoptotic pathway that intersect with Bcl-2. In addition, Bcl-2 is known to also increase hTERT expression and subsequent telomerase activity, further reducing apoptosis in tumor cells. hTERT has been shown to be able to intercept Bax prior to it reaching the mitochondria and triggering the cascade of apoptotic signals. In addition, within the mitochondria hTERT can enhance Bcl-2's inhibitory effect on Bax. To further elucidate the mechanism of interaction between imetelstat sodium and ABT-199 in treated cells, hTERT expression was measured by evaluating transcription levels using RT-qPCR and telomerase activity was assessed using protein from lysed cells in a PCR-based TRAP assay.

hTERT Transcript Levels

Samples from cell experiments (and single agent controls) were collected for molecular analyses to assess combination effects contributing to potential mechanisms of action. AML cells were grown in Falcon T25 flasks (Corning catalog 353135) in batches of 8 million cells in 8 mL of media dosed with either 50 µM imetelstat sodium, 20 nM ABT-199, 50 µM imetelstat sodium plus 20 nM ABT-199, or no drug for 48 and 96 hours similar to previous experiments and then collected as cell pellets for lysing and either nucleic acid or protein extraction. Nucleic acids were purified by first lysing cells with 350 µL of RLT Buffer (Qiagen catalog #1030963) supplemented with 2-mercaptoethanol (Sigma catalog #63689-100ML-F). RNA was purified with the AllPrep RNA/DNA Mini Kit (Qiagen catalog #80204) and reverse transcribed to cDNA using a High Capacity cDNA kit (ThermoFisher catalog #4368814) and pre-amplified prior to analysis with TaqMan PreAmp Master Mix (ThermoFisher catalog #4384557B). Products were analyzed using an in-house developed Taq-Man RT-qPCR assay to measure hTERT transcription levels (TaqMan Universal PCR Master Mix—ThermoFisher catalog #4304437; primer and probe sequences below) using a ViiA7 Real-Time PCR system from ThermoFisher:

```
hTERT full length forward:
                            (SEQ ID NO: 4)
5'-TGTACTTTGTCAAGGTGGATGTA-3' hTERT full length reverse:
                            (SEQ ID NO: 5)
5'-GCTGGAGGTCTGTCAAGGTAGAG-3' hTERT FAM probe:
                            (SEQ ID NO: 6)
5'-CGCGTACGACACCAT-3' MGBNFQ
``` where FAM is the fluorescent reporter and MGBNFQ is the quencher.

Figure 9:
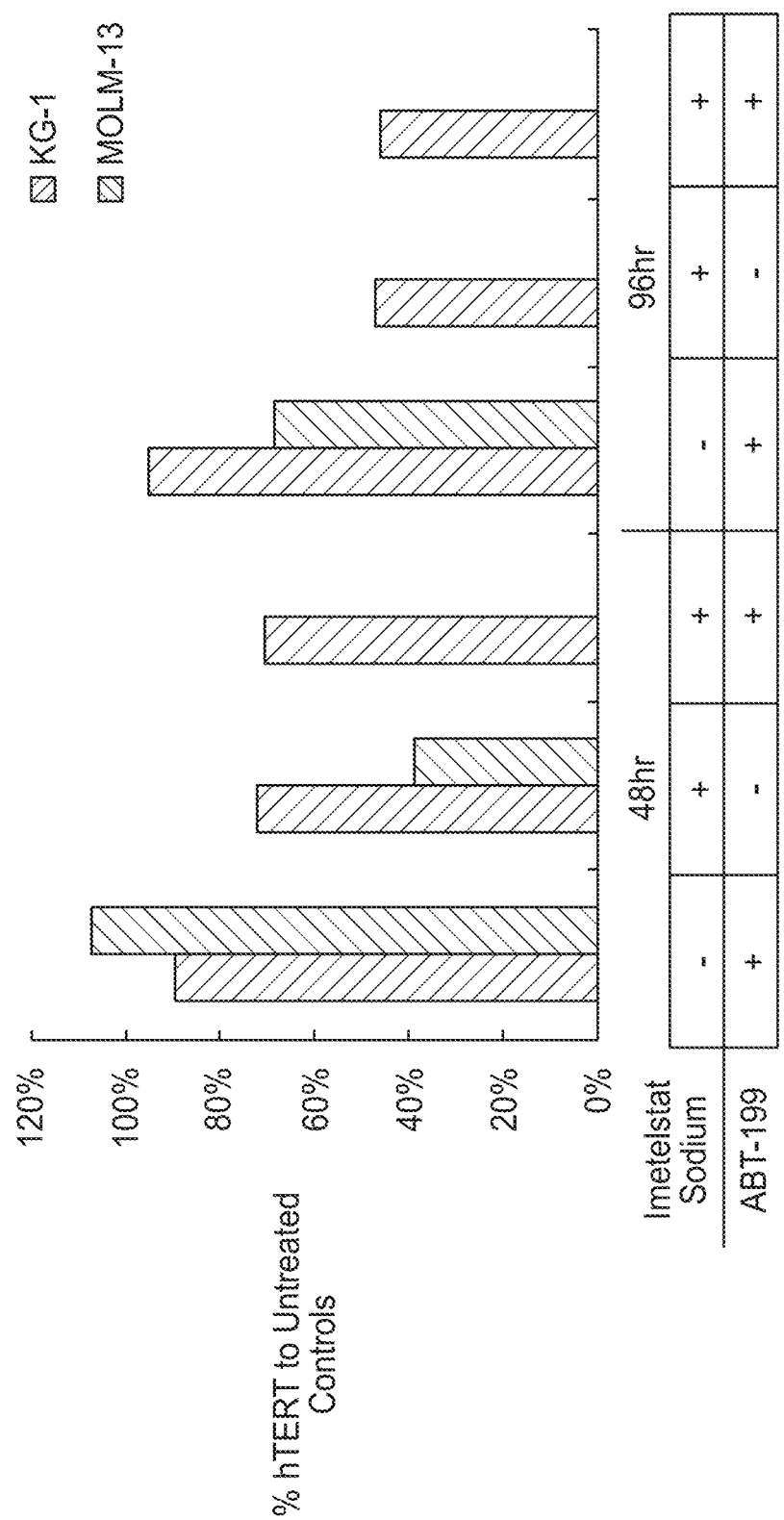
FIG. 9 shows hTERT transcription levels measured by RT-qPCR after treatment with imetelstat sodium, ABT-199, or combination at 48 and 96 hours in KG-1 or MOLM-13 cells.

Bar charts indicating hTERT expression after 48 and 96 hour treatment with imetelstat sodium and/or ABT-199 are shown in FIG. 9. RNA expression levels as measured by RT-qPCR are shown as percentages of untreated controls at the same time of exposure. Results show that KG-1 cells have minimal reduction (90-95% as compared to controls at either time point) in RNA levels of hTERT with ABT-199 treatment and MOLM-13 cells show only a slight reduction in hTERT transcription levels after 96 hours of dosing (~69% as compared to controls). Imetelstat sodium treatment shows a greater reduction in RNA levels for both cell lines, with lower expression at longer treatment times (KG-1 cells from 72% of control at 48 hours and 47% of control at 96 hours; MOLM-13 cells from 39% at 48 hours to undetectable by the assay at 96 hours). For the combination of imetelstat sodium and ABT-199, hTERT expression was unchanged as compared to imetelstat sodium single-agent in KG-1. For MOLM-13 at both time points, hTERT was undetectable.

hTERT Enzymatic Levels

Samples from the previous section for protein analysis were collected as cell pellets by centrifugation at 5 minutes for 1500K for lyses and protein extraction. Protein lysates were analyzed by utilizing a modified method combined from two primary sources (Hou, et al. (2001) 43(3) 519-524 and *Nature Protocols* (2006) 1 (3) 1583-1590). Lysates were generated by adding 80 µL of a 10 mM Tris-EDTA, 1% NP-40, 10% Glycerol, 150 mM NaCl, 1 mM $MgCl_2$, 250 µM Sodium Deoxycholate, 100 µM AEBSF, 5 mM 2-mercaptoethanol buffer and incubating on ice for 30 minutes. Lysates were centrifuged for 15 minutes at max speed and at 4° C. to pellet cellular debris. Protein yield from clarified lysates were quantified using a BCA assay (ThermoFisher catalog 23252) and subjected to a qPCR TRAP-based assay to determine relative telomerase activity (Power SYBR Green PCR Master Mix—ThermoFisher #4367659) using a ViiA7 Real-Time PCR system from ThermoFisher. In this assay, protein lysates are exposed to synthetic oligonucleotides mimicking telomere sequences in the presence of excess dNTPs and SYBR green dye. The greater the activity of telomerase, the greater extension of the synthetic primers, and therefore greater staining of nucleic acid and signal generated by the SYBR dye. This signal is compared to a standard curve of control protein lysate to determine the relative telomerase activity between samples.

```
Forward primer:
                                              (SEQ ID NO: 7)
5'-AATCCGTCGAGCAGAGTT-3'

Reverse primer:
                                              (SEQ ID NO: 8)
5'-GCGCGGCTTACCCTTACCCTTACCCTAACC-3'
```

Results for Molecular Interactions

Figure 10:
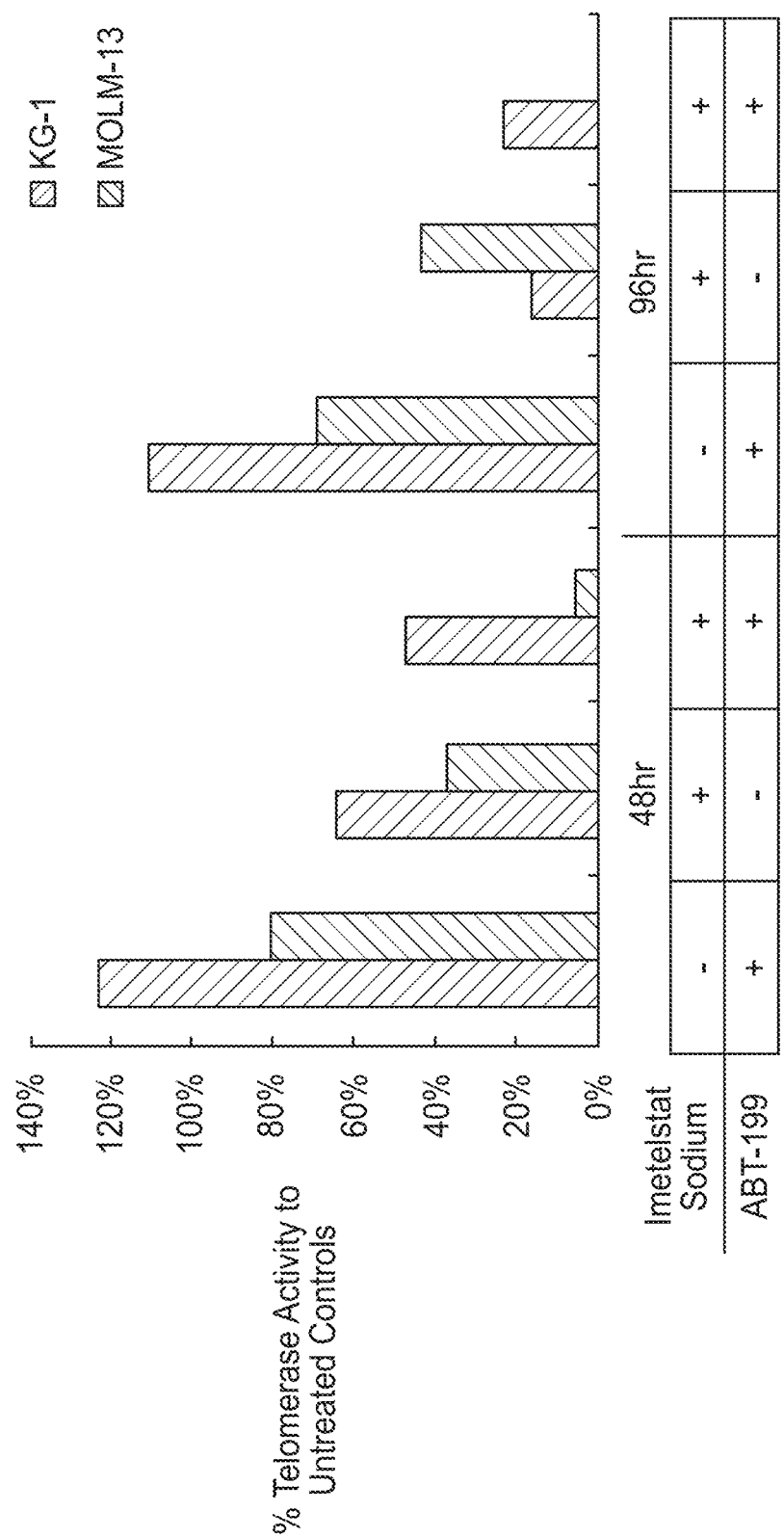
FIG. 10 shows telomerase enzyme activity levels measured by qPCR TRAP after treatment with imetelstat sodium, ABT-199, or combination at 48 and 96 hours in KG-1 or MOLM-13 cells.

Bar charts indicating telomerase activity after 48 and 96 hour treatment with imetelstat sodium and/or ABT-199 are shown in FIG. 10. At 48 hours, ABT-199 shows no effect on telomerase activity in both KG-1 and MOLM-13 cells when used as a single agent. At 96 hours of ABT-199 treatment, activity of telomerase was reduced to ~80% in KG-1 and ~70% indicating that ABT-199 has little effect on telomerase activity. Imetelstat sodium showed reductions in telomerase activity in both KG-1 and MOLM-13 cell lines. In MOLM-13 cells, reductions as compared to control were comparable at both time points (37% for 48 hours, 44% for 96 hours). KG-1 however showed greater reductions of telomerase activity with imetelstat sodium treatment at 96 hours (64% for 48 hours, 16% for 96 hours). With combination treatment, KG-1 showed minimal differences from the imetelstat sodium single-agent whereas in MOLM-13 reduction of telomerase activity was nearly undetectable by the PCR assay.

Example 3: Elucidating Synergy of Combination

Treatment of model AML tumor cell line MOLM-13 was repeated in the experimental format described in Example 1 with the following changes: imetelstat sodium, control mismatch, and control non-complimentary compounds were tested at higher concentrations from 0-75 µM (seven total concentrations) and ABT-199 was tested from 20 pM-1 µM (nine total concentrations). Treated cells were analyzed by Flow cytometry for Annexin V and Propidium Iodide staining as described previously. Events gated in the apoptotic population (Annexin V+/Propidium Iodide+) were used to determine synergy scores for the combination matrix. Combination data analysis was generated by the Horizon Chalice™ Analyzer Software (Horizon Discovery Group, Cambridge, UK). An additional in vitro experiment was performed with MOLM-13 as well as cell line HL-60 to assess the synergy of imetelstat sodium plus ABT-199 upon single exposure to the combination (i.e. no redosing at 48 hours). ABT-199 dose ranges were altered slightly (500 pM-100 nM, five total concentrations) and compared to the equivalent data points in the experiment described above where cells were dosed a second time at 48 hours. Mismatch and non-complimentary controls were not utilized in this experiment.

To statistically qualify the effects observed in treated MOLM-13 cells, dosing combinations were evaluated with the web application of Horizon's Chalice™ Analyzer Software which summarizes the raw data from isobolar analysis fixed ratio dosing according to the method of Chou and Talalay (Chou T C, Talalay P., *Adv Enzyme Regul* 1984; 22:27-55). Combination conditions undergo isobolar analysis to generate a combination index and graphically represent the behavior of a combination with synergistic pairs falling below the isobologram and antagonistic falling above it (additive combinations would be expected to fall on the line). The Horizon Chalice™ Analyzer Software additionally provides a synergy score, with values greater than 1 indicating synergy.

Figure 11:
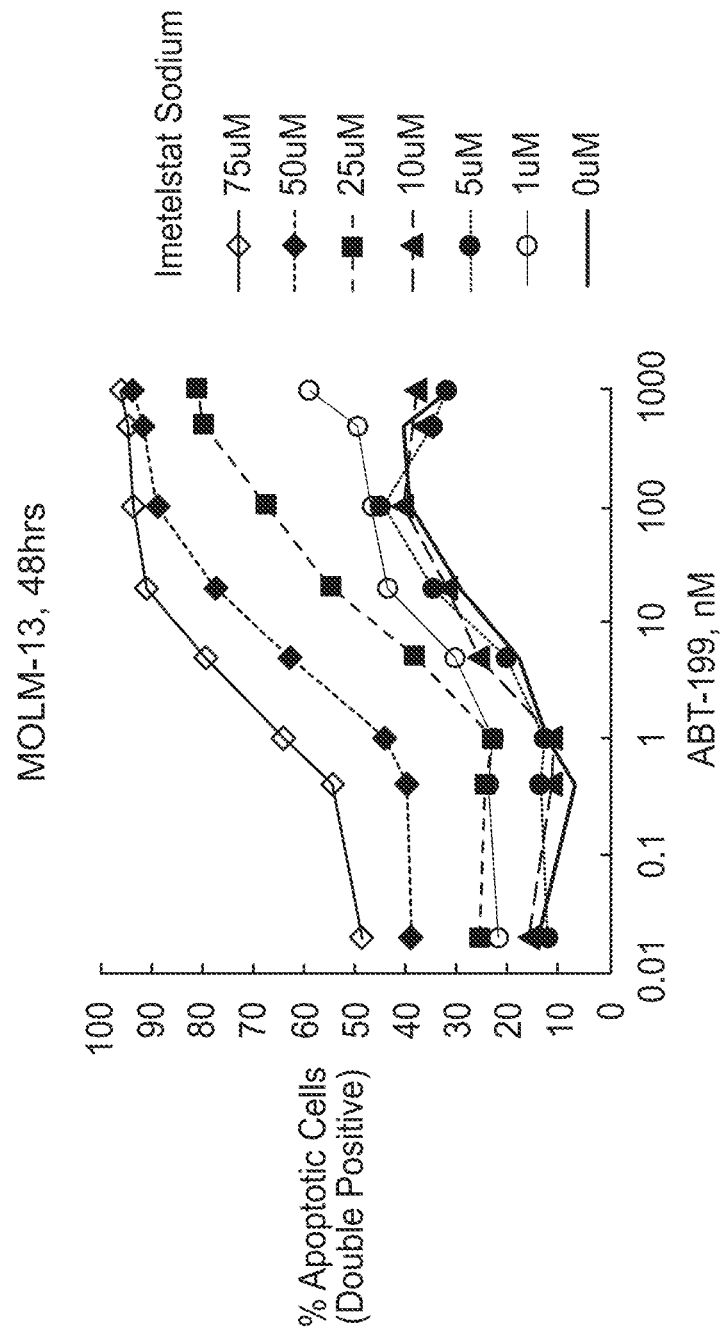
FIG. 11 shows a graph of % apoptotic cells as a concentration of compound for 48 hour treatment of MOLM-13 cells with various concentrations of ABT-199 and/or imetelstat sodium. Apoptotic cells are double labeled with Annexin V and Propidium iodide.
Figure 12A:
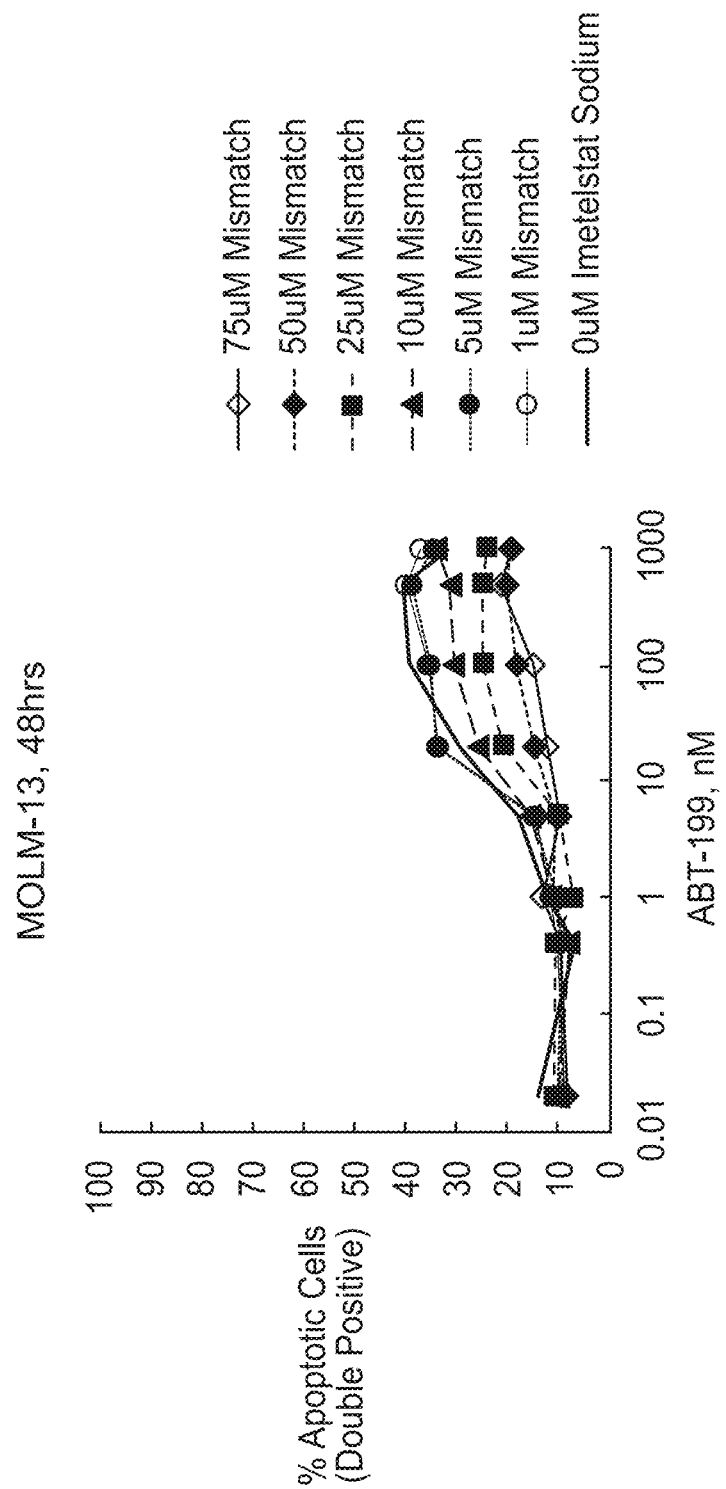
FIGS. 12A and 12B show the % apoptotic cells as a concentration of compound for 48 hour treatment of MOLM-13 cells with various concentrations of ABT-199, control Mismatch oligonucleotide and Non-complimentary oligonucleotide.
Figure 12B:
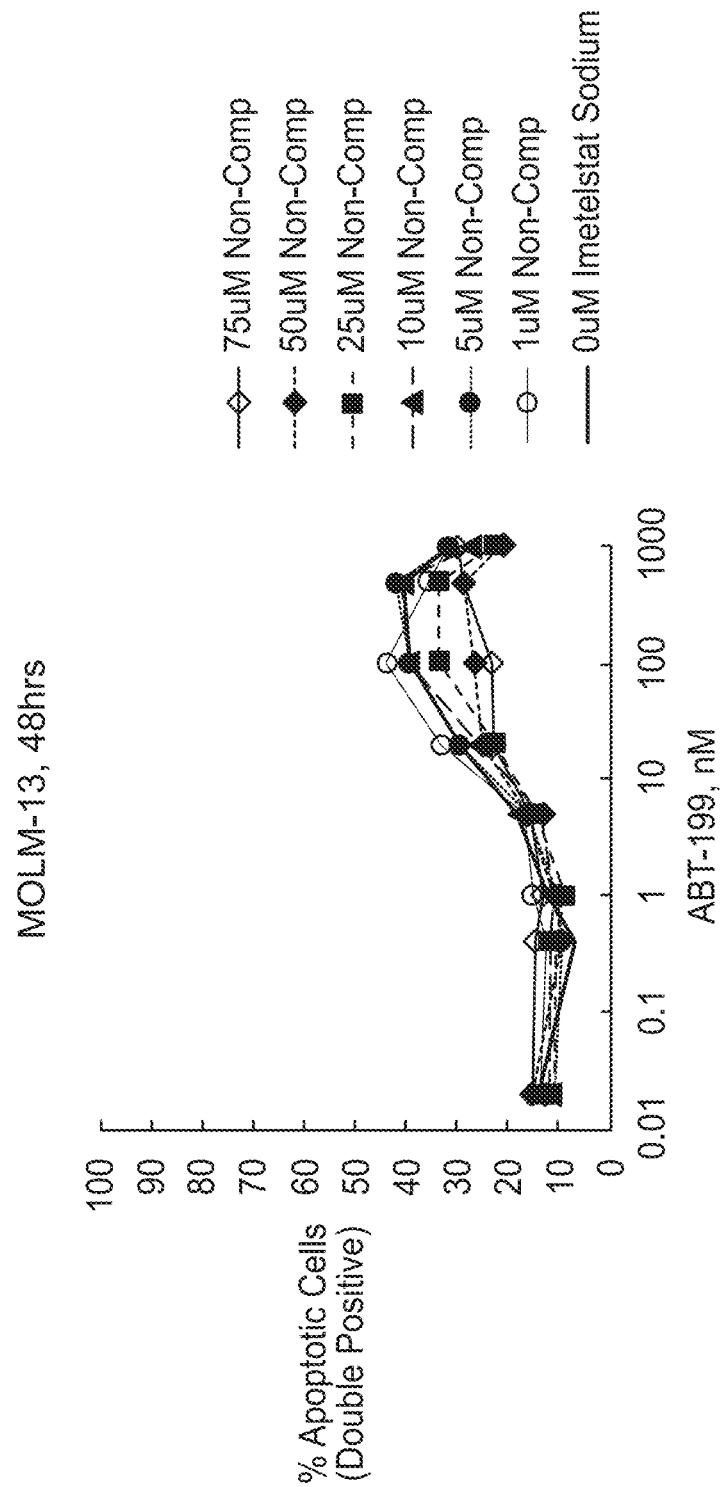

A graph of % apoptotic cells (double label) vs. ABT-199 concentration at various imetelstat sodium concentrations for 48 hour treatment is shown in FIG. 11. Table 19 shows the calculations in excess of additivity (Loewe Model) at each combination for MOLM-13 cells after 48 hour treatment. Values greater than zero are found in the upper right quadrant of the Table 19, where concentrations of ABT-199 are greater than or equal to 20 nM and concentrations of imetelstat sodium are greater than or equal to 25 µM. The Horizon Chalice™ Analyzer Software additionally provides a synergy score, with values greater than 1 indicating synergy. For cells treated with imetelstat sodium, after 48 hours the synergy score was determined to be 5.12. This compares to scores of 0.22 and 0.41 for the mismatch and non-complimentary controls (Table 20 and 21), respectively. A graph of % apoptotic cells (double label) vs. ABT-199 concentration at various imetelstat sodium concentrations for 48 hour treatment is shown in FIG. 12A and FIG. 12B for mismatch and non-complimentary controls respectively.

TABLE 19

Calculations in Excess of Additivity (Loewe Model) for 48 hour treatment with imetelstat sodium

| Loewe Excess; | Imetelstat sodium, µM | | | | | | |
|---|---|---|---|---|---|---|---|
| Synergy Score = 5.12 | 0 | 1 | 5 | 10 | 25 | 50 | 75 |
| ABT-199, nM  1000 | −4 | −2 | −3 | 3 | 45 | 56 | 56 |
| 500 | 5 | 10 | 1 | 2 | 44 | 54 | 54 |
| 100 | 5 | 9 | 12 | 6 | 33 | 51 | 54 |
| 20 | 0 | 1 | 4 | 1 | 22 | 40 | 51 |
| 5 | −4 | −1 | −4 | 0 | 7 | 25 | 39 |
| 1 | 1 | 0 | −1 | −5 | −4 | 6 | 24 |
| 0.2 | 3 | 5 | 7 | 1 | −1 | 2 | 14 |
| 0.04 | 13 | 10 | 10 | 9 | 0 | 1 | 8 |
| 0 | | 9 | 7 | 1 | −4 | 4 | 2 |

TABLE 20

Calculation in Excess of Additivity (Loewe Model) for 48 hour treatment with Mismatch control

| Loewe Excess; | Mismatch, µM | | | | | | |
|---|---|---|---|---|---|---|---|
| Synergy Score = 0.22 | 0 | 1 | 5 | 10 | 25 | 50 | 75 |
| ABT-199, nM  1000 | −4 | 1 | −1 | −1 | −11 | −16 | −16 |
| 500 | 5 | 4 | 3 | −4 | −10 | −15 | −14 |
| 100 | 5 | 1 | 2 | −3 | −9 | −16 | −19 |
| 20 | 0 | 2 | 3 | −4 | −9 | −16 | −18 |
| 5 | −4 | −8 | −9 | −7 | −13 | −12 | −13 |
| 1 | 1 | 0 | −2 | −3 | −4 | 0 | 2 |
| 0.2 | 3 | 5 | 2 | 1 | 2 | 0 | 0 |
| 0.04 | 13 | 7 | 4 | 3 | 2 | 2 | 0 |
| 0 | | 4 | 2 | −1 | 1 | 0 | 0 |

TABLE 21

Calculation in Excess of Additivity (Loewe Model) for 48 hour treatment with Non-complimentary control

| Loewe Excess; | Non-Complimentary, µM | | | | | | |
|---|---|---|---|---|---|---|---|
| Synergy Score = 0.41 | 0 | 1 | 5 | 10 | 25 | 50 | 75 |
| ABT-199, nM  1000 | −4 | −4 | −4 | −7 | −12 | −15 | −6 |
| 500 | 5 | 0 | 7 | 6 | −1 | −7 | −7 |

TABLE 21-continued

Calculation in Excess of Additivity (Loewe Model) for 48 hour treatment with Non-complimentary control

| Loewe Excess; | Non-Complimentary, µM | | | | | | |
|---|---|---|---|---|---|---|---|
| Synergy Score = 0.41 | 0 | 1 | 5 | 10 | 25 | 50 | 75 |
| 100 | 5 | 9 | 6 | 6 | 0 | −8 | −11 |
| 20 | 0 | 3 | −1 | −5 | −7 | −5 | −8 |
| 5 | −4 | −7 | −6 | −6 | −8 | −10 | −6 |
| 1 | 1 | 3 | 0 | −1 | −3 | −2 | −3 |
| 0.2 | 3 | 6 | 3 | 0 | 0 | −1 | 2 |
| 0.04 | 13 | 8 | 6 | 2 | 2 | −1 | 2 |
| 0 | | 6 | −1 | −2 | −1 | −2 | 1 |

Figure 13:
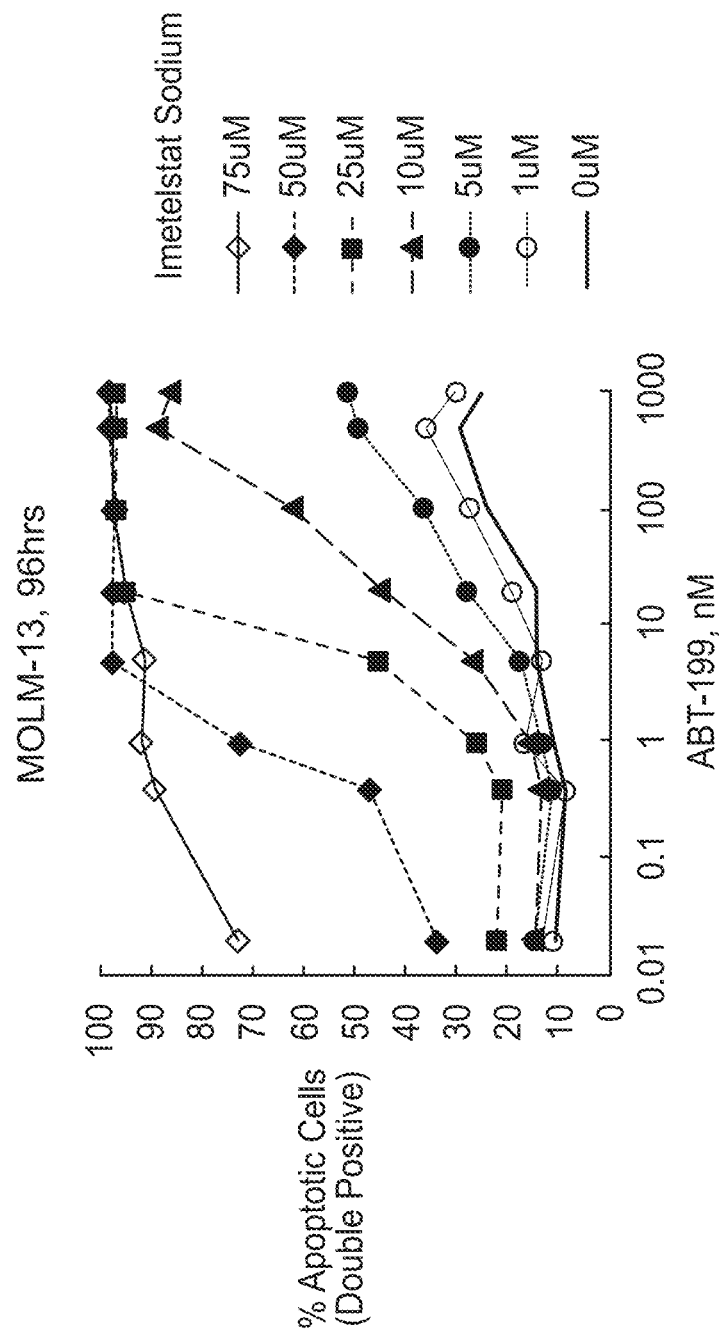
FIG. 13 shows a graph of % apoptotic cells as a concentration of compound for 96 hour treatment of MOLM-13 cells with various concentrations of ABT-199 and/or imetelstat sodium. Apoptotic cells are double labeled with Annexin V and Propidium iodide.
Figure 14B:
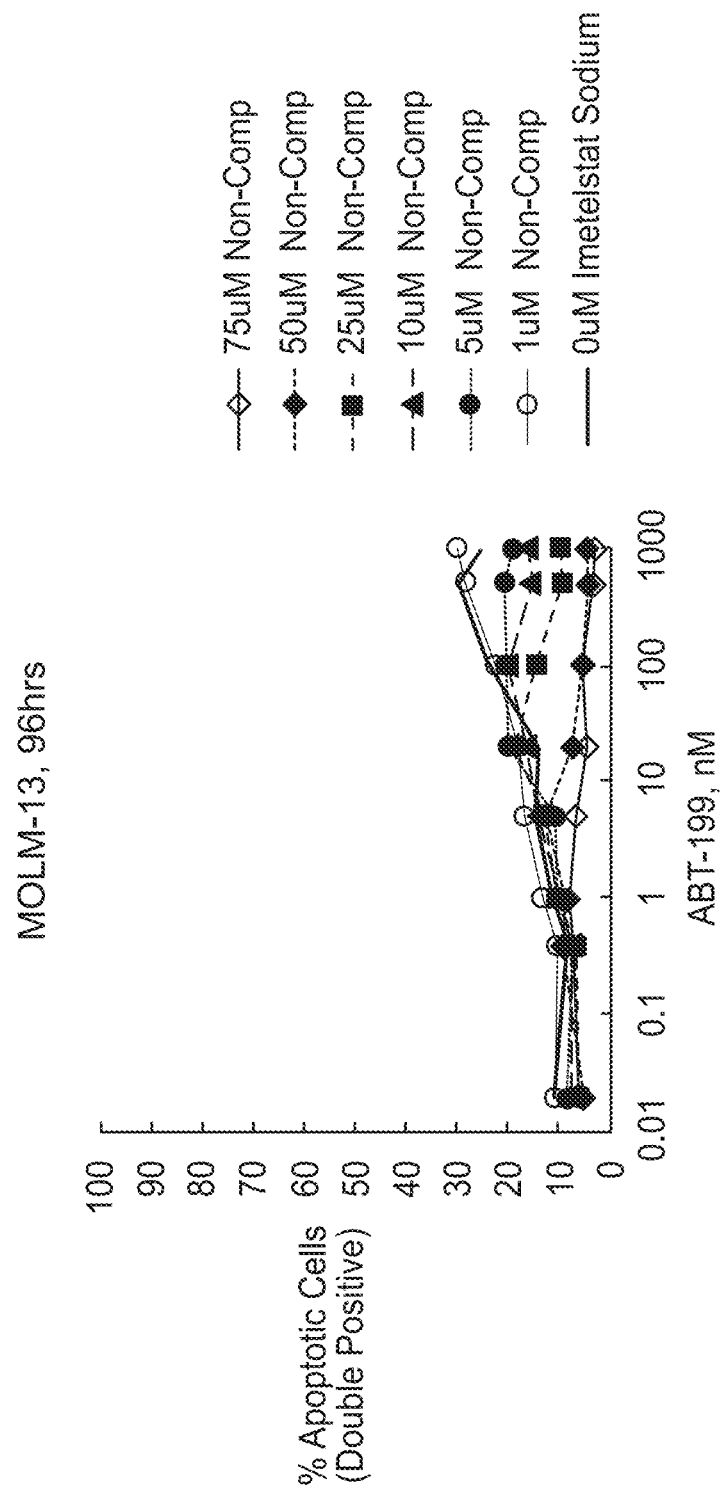

A graph of % apoptotic cells (double label) vs. ABT-199 concentration at various imetelstat sodium concentrations for 96 hour treatment is shown in FIG. 13. Table 22 shows the calculations in excess of additivity (Loewe Model) at each combination for MOLM-13 cells after 96 hour treatment. Values greater than zero are found in the upper right diagonal of Table 19. Surprisingly, even the lowest concentrations of ABT-199 (0.04 nM and 0.2 nM) show synergy with imetelstat sodium at 50 µM and 75 µM imetelstat sodium respectively and the lowest concentrations of imetelstat sodium (1 µM and 5 µM) show synergy with ABT-199 at 500 nM and 100 nM respectively. The Horizon Chalice™ Analyzer Software additionally provides a synergy score, with values greater than 1 indicating synergy. For cells treated with imetelstat sodium, after 96 hours the synergy score was determined to be 11.33. This compares to scores of 0.03 and 0.06 for the mismatch and non-complimentary controls (Table 23 and 24), respectively. A graph of % apoptotic cells (double label) vs. ABT-199 concentration at various imetelstat sodium concentrations for 96 hour treatment is shown in FIG. 14A and FIG. 14B for mismatch and non-complimentary controls respectively.

TABLE 22

Calculations in Excess of Additivity (Loewe Model) for 96 hour treatment with imetelstat sodium

| Loewe Excess; | Imetelstat sodium, µM | | | | | | |
|---|---|---|---|---|---|---|---|
| Synergy Score = 11.33 | 0 | 1 | 5 | 10 | 25 | 50 | 75 |
| ABT-199, nM 1000 | −1 | 5 | 26 | 61 | 71 | 65 | 61 |
| 500 | 4 | 10 | 24 | 63 | 70 | 65 | 61 |
| 100 | 0 | 3 | 12 | 38 | 70 | 64 | 61 |
| 20 | −7 | −2 | 6 | 22 | 69 | 64 | 59 |
| 5 | −2 | −3 | −1 | 6 | 19 | 64 | 55 |
| 1 | 1 | 6 | 0 | −1 | −1 | 38 | 56 |
| 0.2 | 4 | 4 | 1 | −2 | −5 | 13 | 53 |
| 0.04 | 9 | 9 | 6 | 0 | −5 | 0 | 36 |
| 0 | | 6 | 3 | −1 | −5 | −2 | 5 |

TABLE 23

Calculation in Excess of Additivity (Loewe Model) for 96 hour treatment with Mismatch control

| Loewe Excess; | Mismatch, µM | | | | | | |
|---|---|---|---|---|---|---|---|
| Synergy Score = 0.03 | 0 | 1 | 5 | 10 | 25 | 50 | 75 |
| ABT-199, nM 1000 | −1 | −2 | −3 | −6 | −13 | −12 | −14 |
| 500 | 4 | −4 | 0 | −5 | −14 | −12 | −10 |
| 100 | 0 | −2 | 0 | −3 | −19 | −9 | −13 |
| 20 | −7 | −3 | −4 | −4 | −5 | −7 | −5 |
| 5 | −2 | −6 | −5 | −6 | −8 | −6 | 1 |

TABLE 23-continued

Calculation in Excess of Additivity (Loewe Model) for 96 hour treatment with Mismatch control

| Loewe Excess; | Mismatch, µM | | | | | | |
|---|---|---|---|---|---|---|---|
| Synergy Score = 0.03 | 0 | 1 | 5 | 10 | 25 | 50 | 75 |
| 1 | 1 | −1 | −1 | −3 | −5 | −2 | 2 |
| 0.2 | 4 | 2 | 2 | 2 | −1 | 1 | 3 |
| 0.04 | 9 | 3 | 2 | 1 | −1 | −2 | 0 |
| 0 | | 1 | 0 | −1 | −2 | −1 | 1 |

TABLE 24

Calculation in Excess of Additivity (Loewe Model) for 96 hour treatment with Non-complimentary control

| Loewe Excess; | Non-Complimentary, µM | | | | | | |
|---|---|---|---|---|---|---|---|
| Synergy Score = 0.06 | 0 | 1 | 5 | 10 | 25 | 50 | 75 |
| ABT-199, nM 1000 | −1 | 4 | −7 | −9 | −16 | −21 | −23 |
| 500 | 4 | 3 | −5 | −10 | −16 | −21 | −22 |
| 100 | 0 | −2 | −4 | −5 | −10 | −19 | −19 |
| 20 | −7 | −4 | −2 | −5 | −3 | −14 | −17 |
| 5 | −2 | 0 | −6 | −4 | −5 | −5 | −10 |
| 1 | 1 | 3 | 0 | −1 | 0 | −2 | −2 |
| 0.2 | 4 | 1 | 0 | −1 | −2 | −3 | −1 |
| 0.04 | 9 | 1 | −1 | 1 | 1 | −1 | −4 |
| 0 | | 1 | 0 | −1 | −1 | −1 | 1 |

Figure 17A:
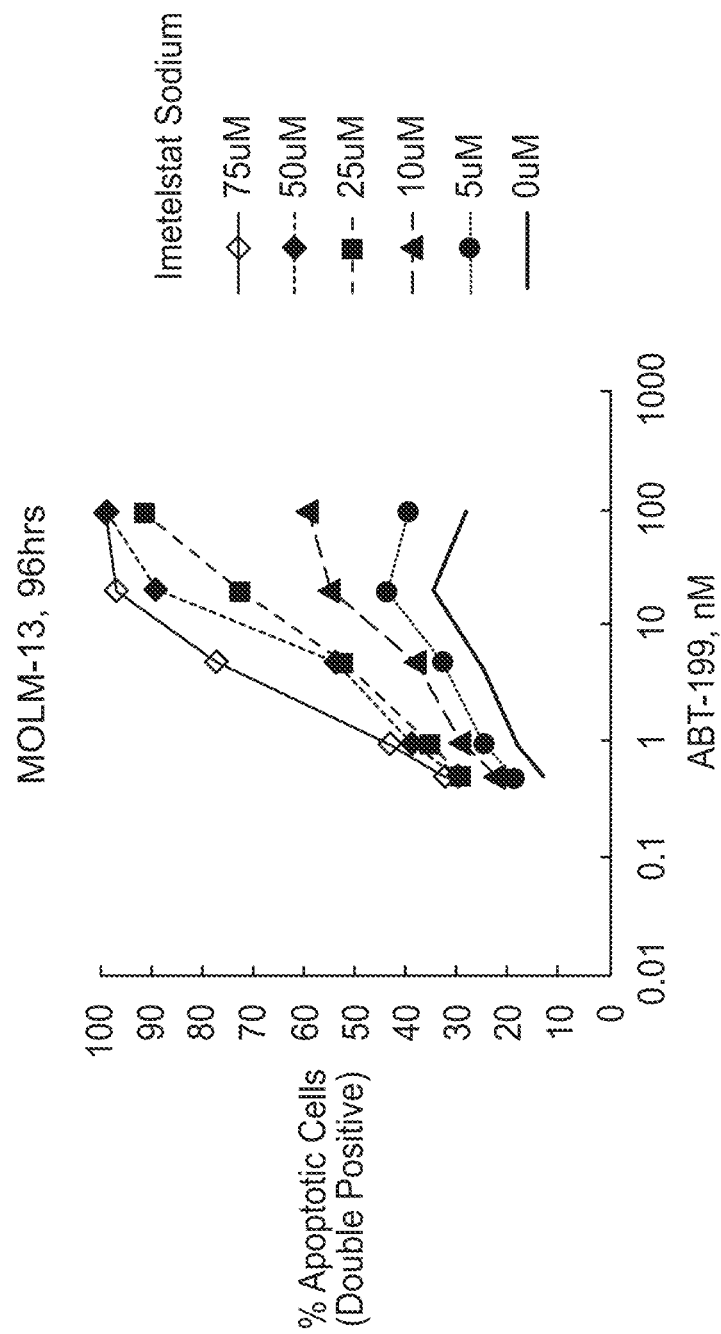
FIGS. 17A and 17B show the apoptotic populations at 96 hours after single dose treatment with imetelstat sodium for MOLM-13 and HL-60 cells.
Figure 17B:
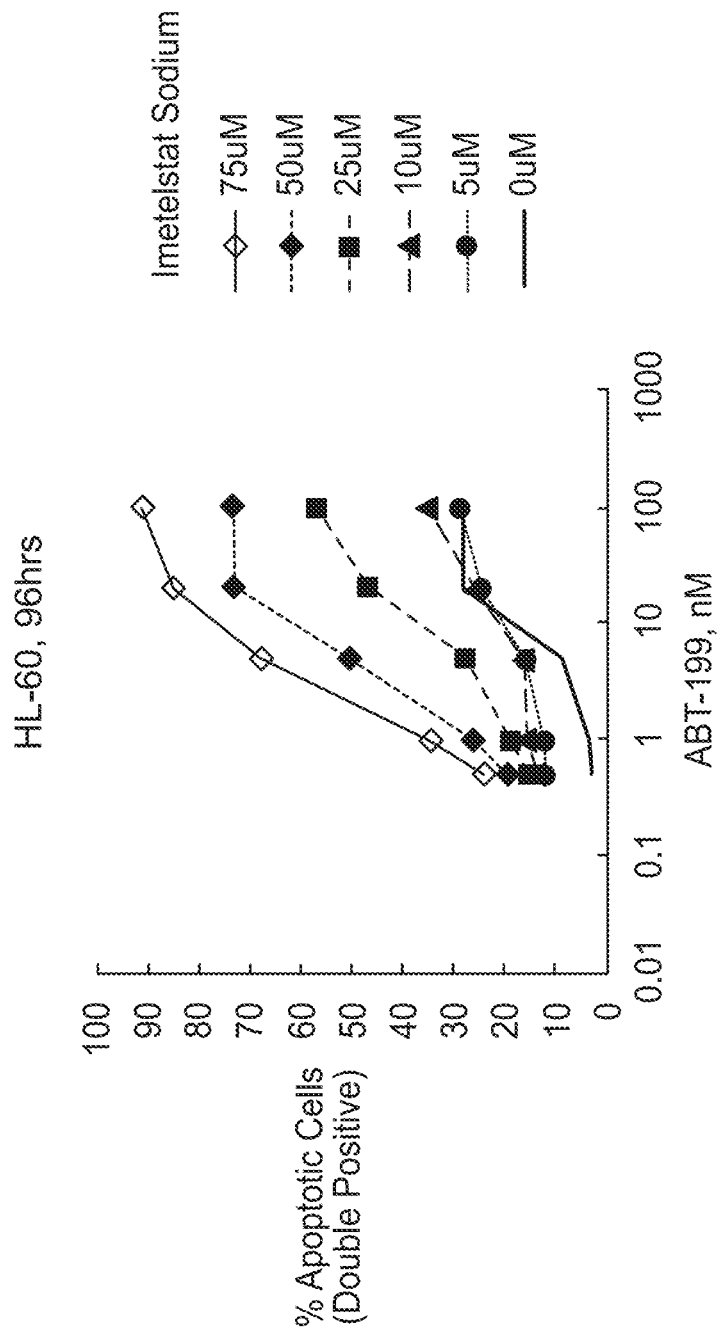

The apoptotic population (double label) at 96 hours after single dose of treatment is shown for MOLM-13 (FIG. 17A) and AML cell line HL-60 (FIG. 17B). A smaller dose range of ABT-199 was used in this experiment to assess the efficacy of imetelstat sodium co-treatment. Table 25 displays the calculations in excess of additivity (Loewe Model) as calculated by the Horizon Chalice™ Analyzer Software for each MOLM-13 combination while Table 26 shows that for HL-60. Though synergistic in both lines, greater synergy is observed in MOLM-13, as evidence by both the greater score as well as the enhanced effect on apoptosis at lower (5 and 10 µM) imetelstat sodium concentrations. The combination with imetelstat sodium shows promise with ABT-199 concentrations down to 1-5 nM doses.

TABLE 25

Calculations in Excess of Additivity (Loewe Model) for 96 hour treatment, single dosing with imetelstat sodium in MOLM-13

| Loewe Excess; | Imetelstat sodium, µM | | | | | |
|---|---|---|---|---|---|---|
| Synergy Score = 3.24 | 0 | 5 | 10 | 25 | 50 | 75 |
| ABT-199, nM 100 | −1 | 10 | 30 | 62 | 69 | 69 |
| 20 | 5 | 14 | 25 | 43 | 60 | 67 |
| 5 | −3 | 4 | 9 | 24 | 26 | 48 |
| 1 | 0 | 3 | 5 | 9 | 12 | 15 |
| 0.5 | 0 | −1 | 0 | 3 | 2 | 5 |
| 0 | 13 | 1 | −2 | 1 | 1 | 0 |

TABLE 26

Calculations in Excess of Additivity (Loewe Model) for 96 hour treatment, single dosing with imetelstat sodium in HL-60

| Loewe Excess; | | Imetelstat sodium, µM | | | | |
|---|---|---|---|---|---|---|
| Synergy Score = 1.77 | | 0 | 5 | 10 | 25 | 50 | 75 |
| ABT-199, nM | 100 | 0 | 1 | 7 | 29 | 46 | 63 |
| | 20 | 1 | −4 | −2 | 19 | 45 | 57 |
| | 5 | 0 | −1 | −2 | 9 | 33 | 49 |
| | 1 | 3 | 2 | 4 | 4 | 9 | 17 |
| | 0.5 | 3 | 2 | 2 | 0 | 2 | 7 |
| | 0 | 2 | 1 | 0 | −3 | −1 | 2 |

For comparison, data plotted in FIG. 13 and used to generate Table 22 were reanalyzed with the Horizon Chalice™ Analyzer Software only at the doses used in FIG. 17A and Table 25. As indicated in Table 27, the synergy score is nearly halved (11.33 to 6.06) from removing the upper levels of the ABT-199 titration curve. This score is roughly double (6.06 versus 3.24) that obtained from the 96 hour, single dose condition (Table 25), suggesting that greater synergy of combining ABT-199 with imetelstat sodium is induced with continual exposure.

TABLE 27

Calculations in Excess of Additivity (Loewe Model) for 96 hour treatment, redosed at 48 hours in MOLM-13 (recreated from FIG. 13)

| Loewe Excess; | | Imetelstat sodium, µM | | | | |
|---|---|---|---|---|---|---|
| Synergy Score = 6.06 | | 0 | 5 | 10 | 25 | 50 | 75 |
| ABT-199, nM | 100 | 2 | 14 | 40 | 69 | 63 | 60 |
| | 20 | −4 | 8 | 25 | 67 | 63 | 58 |
| | 5 | 0 | 1 | 8 | 18 | 63 | 53 |
| | 1 | 4 | 2 | 0 | −2 | 37 | 54 |
| | 0 | | 4 | 0 | −6 | −1 | 4 |

Example 4: Telomerase Inhibitor Imetelstat Sodium in Combination with the BCL-2 Inhibitor Venetoclax Enhances Apoptosis Ex Vivo in AML Patient Samples Acute myeloid leukemia (AML) is an aggressive cancer with limited treatment options outside of chemotherapy, and thus curative agents are needed to fill this unmet need. Both hTERT, the catalytic subunit of telomerase, and BCL-2, an apoptotic regulator, are overexpressed in AML, correlating with disease severity and poor prognosis respectively. Imetelstat sodium is a first-in-class competitive inhibitor of telomerase with clinical activity in hematologic malignancies. Venetoclax (ABT-199), an approved BCL-2 inhibitor for CLL patients who have a 17p deletion and have received at least one prior therapy, has shown promising clinical benefit in AML patients. The study in this example investigated the effect of imetelstat sodium or venetoclax alone, or in combination on AML cells in vitro.

AML cell lines (see Example 1) and AML patient peripheral blood mononuclear cell ("PBMC") samples, which were obtained from AML patient whole blood after Ficoll purification, were treated with imetelstat sodium or venetoclax alone, or in combination, and viable and apoptotic populations of cells were evaluated by flow cytometry. Telomerase activity, hTERT expression and mitochondrial dysfunction were investigated for mechanism of action. AML Patient PBMCs were dosed with imetelstat sodium (0 µM, 25 µM and 50 µM), venetoclax (ABT-199) (0 nM, 20 nM and 100 nM) or the combination for either 16 hours or 40 hours. Apoptosis was measured via flow cytometry staining for Annexin V and propidium iodide. Unstained (i.e. double negative) cells constitute viable cells remaining after treatment.

Specifically, whole blood from AML patients (n=4) was purified using Ficoll-Paque Plus (GE Healthcare catalog #17-1440-03) to purify PBMCs. Ficoll was loaded into 50 mL SepMate centrifuge tubes (StemCell Technologies catalog #85450) and patient blood was pre-diluted with phosphate buffered saline (PBS; ThermoFisher catalog #20012-027) supplemented to 2% fetal bovine serum (FBS) with HyClone FBS (ThermoFisher catalog #SH30070.02) 1:1 before loading atop the Ficoll. Blood was centrifuged to separate PBMCs from red blood cells, granulocytes, etc., and remaining PBMCs washed twice with PBS+2% FBS. Cells were plated at a density of ~300,000 cells per well on 96-well polystyrene U-bottom tissue culture plates (Corning catalog #353777) in RPMI-1640 (ThermoFisher catalog #11875-085) supplemented with 10% HyClone FBS mentioned above and grown in a 37° C. incubator under humidified 5% $CO_2$. No antibiotics were used with ex vivo PBMCs. Cells were treated immediately with imetelstat sodium (Janssen Biotech, Inc.) prepared in RPMI-1640 supplemented with 10% FBS and/or ABT-199 (Selleckchem catalog #S8048) prepared as a 1000× stock in DMSO, diluted 1:100 in PBS (vehicle). Imetelstat sodium was tested from 0-50 µM and venetoclax (ABT-199) was tested from 0-100 nM.

After 16- and 40-hours of treatment, cells were measured for healthy, early apoptotic and apoptotic populations with an Annexin V (interior cell membrane stain) plus propidium iodide (PI, DNA binding dye) flow cytometry assay kit (BioLegend catalog #640914) as described in the Example 1. Additionally, PBMCs were stained for the following differentiation markers: CD45 (V500 conjugated; BD catalog #560777), and CD34 (Pacific Blue conjugated; Biolegend catalog #343512). Events were gated first for CD45 positivity and then for CD34 before Annexin V/propidium iodide assessment as described in Example 1 above. Means and standard deviations were determined for the four patients for CD45$^+$ (leukocytes) and CD45$^+$/CD34$^+$ (leukemic stem cells) populations.

Results of the Ex Vivo Treatments

FIGS. 15A to 15D illustrate the mean response of four AML patient PBMC samples exposed ex vivo to imetelstat sodium and/or venetoclax (ABT-199). Graphs of % viable cells post-treatment for 16 hours of treatment of AML patient CD45$^+$ leukocytes and CD45$^+$/CD34$^+$ leukemic stem cells with various concentrations of venetoclax (ABT-199) and/or imetelstat sodium are shown in FIGS. 15A (CD45$^+$ leukocytes) and 15B (CD45$^+$/CD34$^+$ leukemic stem cells). Graphs of % viable cells post-treatment for 40 hours of treatment of AML patient CD45$^+$ leukocytes and CD45$^+$/CD34$^+$ leukemic stem cells with various concentrations of venetoclax (ABT-199) and/or imetelstat sodium are shown in FIGS. 15C (CD45$^+$ leukocytes) and 15D (CD45$^+$/CD34$^+$ leukemic stem cells). In general, viability of CD45$^+$ leukocytes derived from AML patients was not affected by imetelstat sodium treatment alone and only moderately impacted by venetoclax as single agent after 16-hour and 40-hour exposure. However, reduced cell viability was observed when imetelstat sodium was used in combination with venetoclax. Similar results were observed for the CD45$^+$/CD34$^+$ leukemic stem cell population; a dose-dependent activity in reducing cell viability was noticed when imetelstat sodium was used in combination with venetoclax at both time points, and was most drastic at 40 hours.

Dose-dependent synergistic activity in inducing apoptosis was observed in multiple AML cell lines when combining imetelstat sodium with venetoclax (see Example 1). For example, in the MOLM-13 cell line, single-agent imetelstat sodium and venetoclax had modest apoptotic activity after 48 hours (22% and 30% respectively), but the combination achieved 88% at 48 hours and nearly 100% at 96 hours. Similar enhanced apoptotic activity was also observed in 4 AML patient samples. Molecular analyses showed combining imetelstat sodium with venetoclax reduced hTERT expression and telomerase activity more strongly than either agent alone. This example demonstrates that the combination of imetelstat sodium with venetoclax in AML has a synergistic effect on induction of apoptosis in cell lines and patient samples in vitro.

Example 5: Telomerase Inhibitor Imetelstat Sodium in Combination with the BCL-2 Inhibitor Venetoclax Enhances Survival In Vivo in Acute Myeloid Leukemia As discussed in Example 4, acute myeloid leukemia (AML) is an aggressive cancer with limited treatment options outside of chemotherapy, and thus curative agents are needed. In Example 4, it was demonstrated that the telomerase inhibitor imetelstat sodium in combination with the BCL-2 inhibitor venetoclax enhances apoptosis in vitro. The study in this example investigated the effect of imetelstat sodium or venetoclax alone, or in combination in an in vivo model of acute myeloid leukemia.

Methods

An in vivo study in the MOLM-13 AML disseminated mouse model was conducted to assess efficacy and survival. Specifically, on day 0 of the study, MOLM-13 AML tumor cells were implanted into mice. Mice received 31 days of treatment: (i) Vehicles (MM+PEG400/Phosal50/ETOH); (ii) imetelstat sodium (30 mg/kg); (iii) venetoclax (ABT-199) (100 mg/kg); (iv) MM (mismatched oligonucleotide control) (30 mg/kg) and ABT-199 (100 mg/kg); and (v) imetelstat sodium (30 mg/kg) and ABT-199 (100 mg/kg). The percent survival of the mice was assessed as a function of time (days post tumor cell implantation). The study lasted for a total of 108 days (77 days after stopping treatment).

Fifty female SCID-beige mice (6-week-old, Jackson Laboratory) were intravenously injected with 1 million MOLM-13 cells and randomly divided into five groups. On day one post-injection, the mice were treated with either of five conditions as listed in Table 28.

TABLE 28

Treatment conditions for SCID-beige mice inoculated with the MOLM-13 disseminated AML model.

| Group | Drug | Dosage | n | Route | Schedule |
|---|---|---|---|---|---|
| 1 | Vehicles: MM PEG400, Phosal50, ETOH | 30 mg/kg — | 10 | ip po | TIW × 4 weeks qd (7x) × 4 weeks |
| 2 | imetelstat sodium | 30 mg/kg | 10 | ip | TIW × 4 weeks |
| 3 | venetoclax (ABT-199) | 100 mg/kg | 10 | po | qd (7x) × 4 weeks |
| 4 | MM venetoclax (ABT-199) | 30 mg/kg 100 mg/kg | 10 | ip po | TIW × 4 weeks qd (7x) × 4 weeks |
| 5 | imetelstat sodium venetoclax (ABT-199) | 30 mg/kg 100 mg/kg | 10 | ip po | TIW × 4 weeks qd (7x) × 4 weeks |

Abbreviations:
ip, intraperitoneal;
po, by mouth;
TIW, three times a week;
qd, once daily;
mg/kg, milograms drug per kilogram animal Mice were observed daily and body weights were measured twice a week. The survival of mice in each group was followed. The study was terminated on day 108, which was 77 days post last treatment. The increased life span ("ILS") was evaluated for each group, and the % ILS versus the vehicle control was calculated as:

% ILS=100×(T−C)/C where T is the median survival of the treatment group and C is the median survival of the control group.

Results of the In Vivo Study

Figure 16:
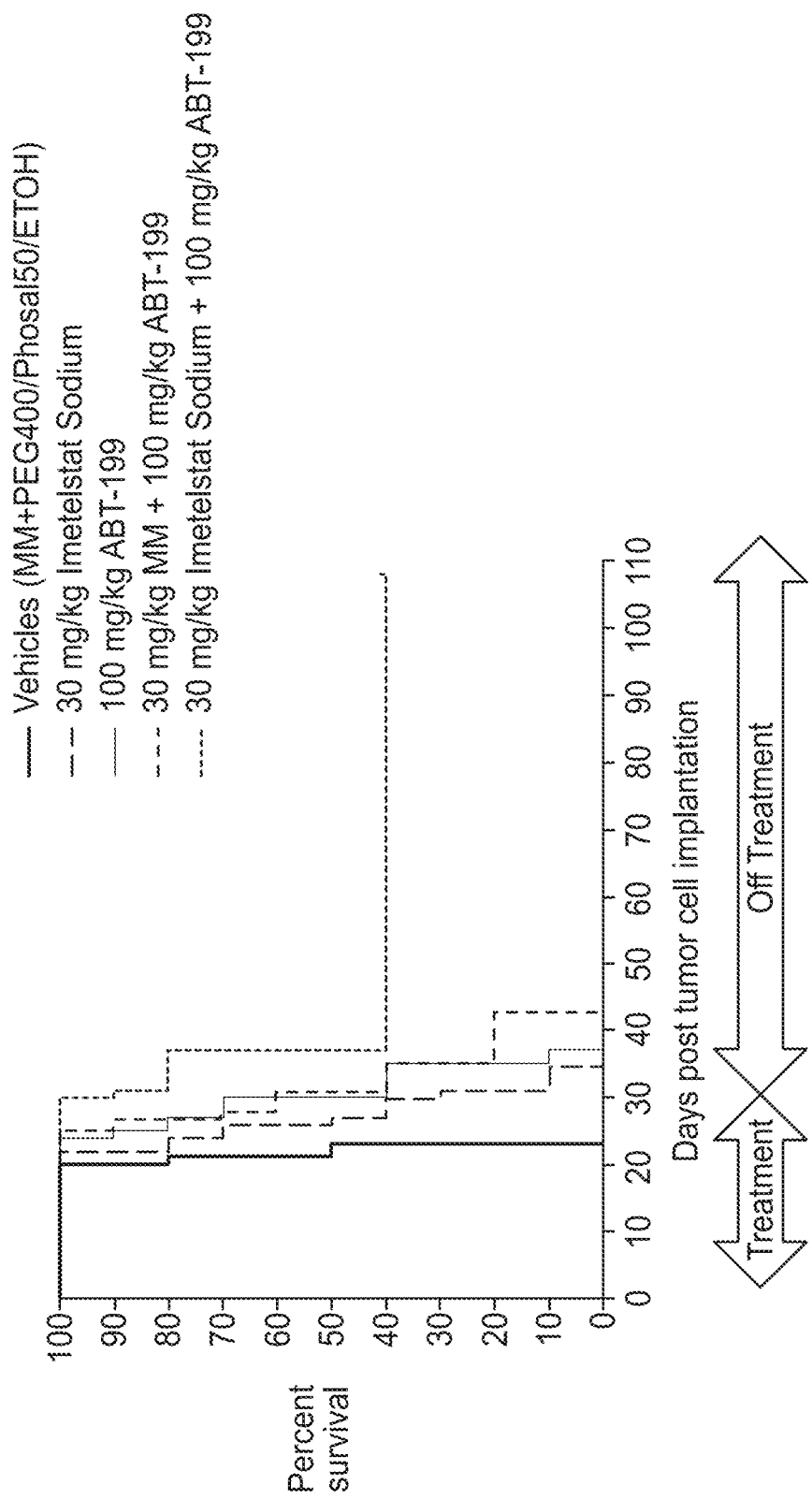
FIG. 16 shows the in vivo antitumor efficacy and survival benefit of imetelstat sodium or ABT-1 as monotherapy or both agents in combination in a mouse model. Mice were inoculated with the MOLM-13 cells (disseminated model) and treated with: vehicle, imetelstat sodium and/or ABT-199, or mismatched oligonucleotide control plus ABT-199. Mice were monitored for survival (n=10 mice/group at onset) post-treatment. Specifically.

A Kaplan-Meier Survival Plot for the AML disseminated model MOLM-13 on day 108 is shown in FIG. 16. In particular, FIG. 16 shows the percent survival of mice as a function of days post-tumor cell implantation. The median survival and % increased life span ("ILS") calculated for the various treatment groups are shown in Table 29. The results show that the median survival time for the imetelstat sodium single agent treated mice was 26.5 days which translated to 20.4% ILS (p=0.0009) compared to vehicle. Treatment with venetoclax (ABT-199) single agent resulted in a median survival time of 30 days and 36.3% ILS (p≤0.0001). Combined with the mismatched (MM) oligo control, ABT-199 gave similar effects of ABT-199 alone: median survival time of 31 days and of 40.9% ILS (p≤0.0001). The combination of imetelstat sodium with ABT-199 resulted in the best outcome with a median survival time of 37 days and significant efficacy of 68.1% ILS (p≤0.0001). Moreover, four mice (40%) from this combination treatment group were long lived and survived beyond 108 days, demonstrating enhanced survival benefit.

TABLE 29

Median survival time and percent increased life span (% ILS; as compared to control) of MOLM-13 implanted mice treated with imetelstat sodium and/or venetoclax (ABT-199), or MM (mismatch oligonucleotide control).

| Group | Median Survival (days) | % ILS | p |
|---|---|---|---|
| Vehicles: MM | 22 | — | — |
| imetelstat sodium | 26.5 | 20.4 | 0.0009 |
| ABT-199 | 30 | 36.3 | 0.0001 |
| MM + ABT-199 | 31 | 40.9 | 0.0001 |
| imetelstat sodium + ABT-199 | 37 | 68.1 | 0.0001 |

All mice tolerated the combination of imetelstat sodium with venetoclax, and an increased life span was observed when compared to imetelstat sodium (39.6%, p=0.0011) or to venetoclax (23.3%, p=0.0001) alone. In the combination group, 40% of treated mice were alive 77-days after treatment discontinued, demonstrating significant survival benefit with potential cure. The results in this Example, as well as Example 4, demonstrate that the combination of imetelstat sodium with venetoclax in AML has a synergistic effect on induction of apoptosis in cell lines and patient samples in vitro, which translates into prolonged survival and a potential cure in xenograft models.

EQUIVALENTS AND INCORPORATION BY REFERENCE

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

What is claimed is:

1. A method of treating acute myeloid leukemia comprising administering imetelstat and ABT-199 to a subject having acute myeloid leukemia, wherein the administration of ABT-199 is one day before, one day after, or the same day as, the administration of imetelstat
    wherein imetelstat is administered for 1, 2, 3, 4, 5, 6, 7, 8 or more than 8 dosage cycles, each cycle comprising:
        (a) intravenous administration of about 7-10 mg/kg imetelstat once every four weeks;
        (b) intravenous administration of about 7-10 mg/kg imetelstat once weekly for four weeks;
        (c) intravenous administration of about 2.5-10 mg/kg imetelstat once every three weeks; or
        (d) intravenous administration of about 0.5-9.4 mg/kg imetelstat once every four weeks, and
    wherein ABT-199 is administered at a dose of:
        (a) about 50-400 mg ABT-199 daily;
        (b) about 2 mg ABT-199 on day 1 with daily escalation to a final dose of about 800 mg on day 6 and daily thereafter; or
        (c) about 25 mg ABT-199 on day 1 with daily escalation to a final dose of about 400 mg on day 5 and daily thereafter.

2. An in vitro method of inducing apoptosis in an acute myeloid leukemia (AML) cell comprising:
    contacting the cell with imetelstat sodium at a concentration of 10-75 μM; and
    contacting the cell with ABT-199 at a concentration of 5-1000 nM.

3. The method of claim 1, wherein imetelstat is imetelstat sodium.

4. A method of inducing apoptosis in an acute myeloid leukemia cell comprising contacting the cell with a therapeutically effective amount of imetelstat and contacting the cell with a therapeutically effective amount of ABT-199, wherein the contacting with ABT-199 is one day before, one day after, or the same day as, the contacting with imetelstat
    wherein the contacting with imetelstat comprises administration for 1, 2, 3, 4, 5, 6, 7, 8 or more than 8 dosage cycles, each cycle comprising:
        (a) intravenous administration of about 7-10 mg/kg imetelstat once every four weeks;
        (b) intravenous administration of about 7-10 mg/kg imetelstat once weekly for four weeks;
        (c) intravenous administration of about 2.5-10 mg/kg imetelstat once every three weeks; or
        (d) intravenous administration of about 0.5-9.4 mg/kg imetelstat once every four weeks, and
    wherein the contacting with ABT-199 comprises administration at a dose of:
        (a) about 50-400 mg ABT-199 daily;
        (b) about 2 mg ABT-199 on day 1 with daily escalation to a final dose of about 800 mg on day 6 and daily thereafter; or (c) about 25 mg ABT-199 on day 1 with daily escalation to a final dose of about 400 mg on day 5 and daily thereafter.

5. The method of claim 4, wherein imetelstat is imetelstat sodium.

\* \* \* \* \*

UNITED STATES PATENT AND TRADEMARK OFFICE
CERTIFICATE OF CORRECTION

PATENT NO. : 11,278,561 B2
APPLICATION NO. : 15/662706
DATED : March 22, 2022
INVENTOR(S) : Fei Huang et al.

It is certified that error appears in the above-identified patent and that said Letters Patent is hereby corrected as shown below:

In the Specification

In Column 6, Line 18, please replace "leukemiallymphoma" with --- leukemia/lymphoma ---;

In Column 6, Line 19, please replace "leukemiallymphoma" with --- leukemia/lymphoma ---;

In Column 6, Line 25, please replace "lymphoma/Waldenstrim" with --- lymphoma/Waldenström ---;

In Column 7, Line 19, please replace "Waldenstrim" with --- Waldenström ---;

In Column 8, Line 18, please replace "lymphoma/Waldenstrim" with --- lymphoma/Waldenström ---;

In Column 14, Line 50, please replace "lymphoma/Waldenstrim" with --- lymphoma/Waldenström ---;

In Column 25, Lines 6 and 62, please replace "lymphoma/Waldenstrim" with --- lymphoma/Waldenström ---;

In Column 27, Lines 7 and 45, please replace "lymphoma/Waldenstrim" with --- lymphoma/Waldenström ---; and In Column 31, Line 26, please replace "50 M" with --- 50 µM ---.

Signed and Sealed this
Twenty-fourth Day of May, 2022

Katherine Kelly Vidal
*Director of the United States Patent and Trademark Office*

SEQUENCE LISTING

```
<160> NUMBER OF SEQ ID NOS: 8

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tagggttaga caa                                                          13

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taggtgtaag caa                                                          13

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aacagattgg gat                                                          13

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtactttgt caaggtggat gtga                                              24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
gctggaggtc tgtcaaggta gag                                          23

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cgcgtacgac accat                                                   15

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatccgtcga gcagagtt                                                18

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcgcggctta cccttaccct taccctaacc                                   30
```